United States Patent
Lopez

(10) Patent No.: US 7,932,284 B2
(45) Date of Patent: Apr. 26, 2011

(54) INDOLE SULFONAMIDE MODULATORS OF PROGESTERONE RECEPTORS

(75) Inventor: Jose Eduardo Lopez, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 358 days.

(21) Appl. No.: 12/160,460

(22) PCT Filed: Jan. 17, 2007

(86) PCT No.: PCT/US2007/060626
§ 371 (c)(1),
(2), (4) Date: Jul. 10, 2008

(87) PCT Pub. No.: WO2007/087488
PCT Pub. Date: Aug. 2, 2007

(65) Prior Publication Data
US 2009/0069400 A1 Mar. 12, 2009

Related U.S. Application Data

(60) Provisional application No. 60/761,637, filed on Jan. 24, 2006.

(51) Int. Cl.
*A61K 31/404* (2006.01)
*C07D 209/04* (2006.01)

(52) U.S. Cl. ......... 514/415; 548/469; 548/509; 514/412

(58) Field of Classification Search .................. 548/469, 548/509; 514/412, 415
See application file for complete search history.

(56) References Cited

U.S. PATENT DOCUMENTS

| | | | |
|---|---|---|---|
| 5,744,488 A | 4/1998 | Cross et al. | |
| 6,015,822 A | 1/2000 | Brendel et al. | |
| 7,105,515 B2 | 9/2006 | Merce-Vidal et al. | |
| 7,449,478 B2 | 11/2008 | Hsieh et al. | |
| 2003/0191124 A1 | 10/2003 | Merce-Vidal et al. | |
| 2003/0195244 A1 | 10/2003 | Hsieh-Pang et al. | |
| 2003/0199689 A1 | 10/2003 | Nazare et al. | |
| 2005/0065202 A1 | 3/2005 | Vidal et al. | |
| 2005/0222201 A1 | 10/2005 | Birkinshaw et al. | |
| 2005/0245485 A1 | 11/2005 | Lanter et al. | |
| 2006/0111427 A1 | 5/2006 | Jiang et al. | |
| 2007/0185161 A1 | 8/2007 | Gavardinas et al. | |

FOREIGN PATENT DOCUMENTS

| | | |
|---|---|---|
| WO | WO 99/43654 | 9/1999 |
| WO | WO 00/66554 | 11/2000 |
| WO | WO 03/027094 | 4/2003 |
| WO | WO 03/101981 | 12/2003 |
| WO | 2004/019935 | 3/2004 |
| WO | WO 2005/013976 | 2/2005 |
| WO | WO 2005/014543 | 2/2005 |
| WO | WO 2005/092854 | 10/2005 |
| WO | WO 2006/049889 | 5/2006 |

OTHER PUBLICATIONS

Dai, et al., "Chemistry of aminophenols. Part 2: A general and efficient synthesis of indoles possessing a nitrogen substituent at the C4, C5, C6 and C7 positions," Tetrahedron Letters, vol. 43, pp. 7699-7702 (2002).
Liou, et al., "Concise Synthesis and Structure-Activity Relationships of Combretastatin A-4 Analogues, 1-Aroylindoles and 3-Aroylindoles, as Novel Classes of Potent Antitubulin Agents," J.Med. Chem., 2004, 47, 4247-4257.
Beevers, et al., "Novel indole inhibitors of IMPDH from fragments: Synthesis and initial structure-activity relationships," Bioorganic & Medicinal Chemistry Letters, 2006, vol. 16, 2539-2542.
Williams, et al., "The effects of the selective progesterone receptor modulator asoprisnil on the morphology of uterine tissues after 3 months treatments in patients with symptomatic uterine leiomyomata," Human Reproduction, 2007, 1-9.
Sptiz, et al., "Progesterone receptor antagonists and selective progesterone receptor modulators: proven and potential clinical applications." Expert Rev. Obstet. Gynecol. 2(2), 2007.
Mutter, et al., "The spectrum of endometrial pathology induced by progesterone receptor modulators." Modern Pathology (2008) 21, 591-598.

*Primary Examiner* — Golam M Shameem
(74) *Attorney, Agent, or Firm* — James B. Myers

(57) ABSTRACT

Compounds of Formula (I), wherein n is 1 or 2, and R1, R2, R3, R4, R5, R6, R7, and R8 are as defined herein, their preparation, pharmaceutical compositions, and methods of use are disclosed.

5 Claims, No Drawings

INDOLE SULFONAMIDE MODULATORS OF PROGESTERONE RECEPTORS

REFERENCE TO RELATED APPLICATION

This application is submitted as a United States national phase entry, pursuant to 35 U.S.C. §371, of PCT/US2007/060626, filed on 17 Jan. 2007, which claims the benefit of U.S. provisional patent application Ser. No. 60/761,637, filed 24 Jan. 2006, each of which is incorporated by reference herein.

FIELD OF THE INVENTION

The current invention relates to the fields of medicinal organic chemistry, pharmacology, and medicine. Further, the current invention relates to novel compounds and methods useful for the treatment of tumors, gynecological disorders, and related symptoms and sequelae.

BACKGROUND OF THE INVENTION

Leiomyomas are the most common non-cancerous tumor in women of childbearing age. Uterine leiomyomas (or fibroids) are considered to be benign tumors of muscle and connective tissue that develop within or are attached to, the uterine wall. It is estimated from ultrasound examination that over 70% of women will develop fibroids by the time they reach menopause. (Baird et al., *Am J. Obstet. Gynecol.* 2005; 188: 100-107; and Cramer et al. *Am. J. Clin Pathol.* 1990; 90: 435-438.) While not all women are symptomatic to warrant therapy, a significant number of women experience moderate to severe symptoms including abnormal uterine bleeding, pelvic pressure and pain, and reproductive dysfunction.

Current treatment therapies include surgical intervention, such as, hysterectomies and myomectomies. Less invasive procedures include: uterine artery embolization and thermoablative coagulation. Medical therapies include hormone treatment. Currently the only FDA approved hormone treatment is the use of a GnRH (gonadotropin-releasing hormone) agonist preoperatively with iron. (Walker and Stewart, *Science*, 2005; 308; 1589-1592.) The GnRH agonist therapy is often limited to 1-3 months because of measurable bone loss which leads to osteoporosis with long term use. Further, the GnRH agonist treated myomas often return to pre-treatment size within weeks of therapy cessation. Consequently, this treatment is often used to reduce the size of the myoma and allow the woman to prepare for its eventual surgical removal. (Stewart, *Lancet,* 2001; 357; 293-298.)

These options have undesirable consequences for women who wish to conceive at a later time. Obviously, a hysterectomy would prohibit subsequent conception, and the other surgical options also present risks, including uterine rupture and recurrent fibroids. Medical treatment can also cause significant side effects. For example, GnRH agonists produce an environment in the body that is very similar to that of menopause, with associated side effects like hot Rashes, vaginal dryness, and, as noted above, loss of bone density. These and other problems highlight the continuing need to treat and ameliorate the gynecological disorders such as myomas in general, more specifically but not exclusively, leiomyomas, and endometriosis, and their attendant symptoms.

As further background, the following references describe indole or indoline structures and their therapeutic use.

Merce et al. in WO 2005/013976 disclose indole-6 sulfonamide derivatives of the following formula substituted as described therein:

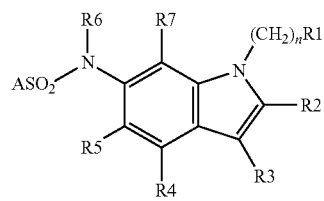

which are stated to be useful as 5-HT-6 modulators.

Hsieh et al. in U.S. Pat. No. 6,933,316 disclose indole compounds of the formula below and substituted as described therein:

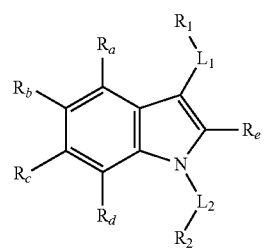

which are stated to exhibit anti-cancer activities and function by targeting microtubule polymerization/depolymerization.

The above references either do not described efficacious treatment of abnormal tissue growth or compounds useful as progesterone receptor ligands. Further, the described compounds exhibit one or more undesirable characteristics including low bioavailability, low progesterone binding affinity, non specific binding to hormone receptors in general, i.e., absence of progesterone receptor (PR) specific binding, and no or low efficacious treatment of tumors, in general, and more specifically no or low efficacious treatment of myomas, leiomyomas, and endometriosis. Consequently, a significant need remains for effective compounds and treatment method(s) for tumors, gynecological disorders, and related sequelae. The present invention addresses these needs.

SUMMARY OF THE INVENTION

Unless specified to the contrary, the following numbering system for the indole core illustrated below will be used in the present application:

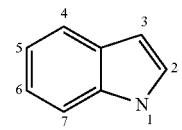

The present invention provides a compound of Formula I:

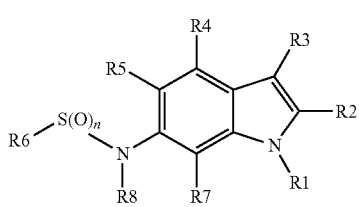

where n is 1 or 2 and R1-R8 are herein described. For selected applications, preferred compounds of the present invention are selective progesterone receptor modulators (SPRMs).

In another form, the present invention also provides a pharmaceutical composition comprising a compound according to Formula I as defined above and one or more of the following: a carrier, a diluent, and an excipient.

The present invention also provides a method of preparing a compound of Formula I above. In one form the method includes combining a compound of Formula II

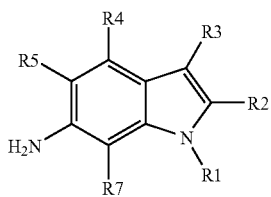

with a base and R6SO$_2$Cl. This method can also include reducing the nitro group on a compound of Formula IIA below to the amine.

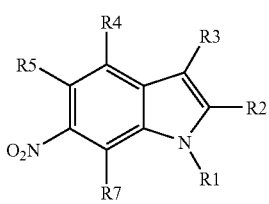

In another form the method includes replacing the halogen (X) in the indole 3 position on Formula III below

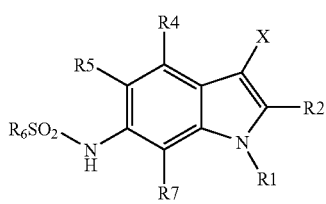

with an optionally substituted aryl, optionally substituted heteroaryl or optionally substituted bicyclic aryl or bicyclic heteteroaryl group. This method can include first replacing the halogen with a more reactive leaving group such as the dioxaborolane group formed from bis(pinacolato)diboron, for example.

In another form, the present invention provides a method of modulating progesterone receptor activity and/or treating diseases mediated by modulation of the progesterone receptor activity in a mammal including non-human and human (more specifically female). The method comprises administering a therapeutically effective composition comprising a compound of Formula I, or a pharmaceutically acceptable salt, solvate, enantiomer, racemate, diastereomer or mixture of diastereomers thereof to a patient. In a preferred embodiment, the method comprises administrating a compound of Formula I or a pharmaceutically acceptable salt, solvate, enantiomer, racemate, diastereomer or mixture of diastereomers thereof exhibiting a high degree of progesterone receptor (PR) binding selectivity. In a more preferred embodiment, the administered compounds exhibit a progesterone receptor binding selectivity greater than or equal to about 5 times that for the androgen receptor (AR), glucocorticoid receptor (GR), and mineralocorticoid receptor (MR), as determined by comparing the individual IC$_{50}$ values or the K$_i$ values from the respective binding assays. In another preferred embodiment, the method comprises administering a compound of Formula I or a pharmaceutically acceptable salt, solvate, enantiomer, racemate, diastereomer or mixture of diastereomers thereof capable of or selected to elicit a PR agonist affect, a PR antagonist affect, a partial PR agonist affect, or a partial PR antagonist affect or a mixture of these affects.

In yet another form, the present invention provides a method of treating or ameliorating the effects of one or more of: tumors; neoplasms; myomas (myomata); leiomyomas (uterine fibroids); endometriosis (adenomyosis); postoperative peritoneal adhesions; endometrial hyperplasia; polycystic ovary syndrome; carcinomas and adenocarcinomas of the uterus, ovary, breast, colon, and prostate; infertility; fertility control; female sexual function; other gynecological or menstrual syndromes, such as, abnormal or dysfunctional bleeding, amenorrhea, menorrhagia, hypermenorrhoea, and dysmenorrheal; or pathological sequelae due to the above disorders/syndromes in a mammal including non-human and human (more specifically female).

In yet another form, the present invention provides a method of treating endometriosis or symptoms and pathological sequelae due to endometriosis.

In another form, the present invention provides a method of treating or ameliorating the effects of gynecological or menstrual disorders in a mammal by administering a therapeutically effective dose of a compound of Formula I or pharmaceutically acceptable salt, solvate, enantiomer, racemate, diastereomer, or mixture of diastereomers to said mammal.

In still yet another form, the present invention provides use of a compound for the manufacture of a medicament for treating or ameliorating the effects of one or more of: leiomyomas, endometriosis, and dysfunctional bleeding.

The present invention also provides a combination therapy, administered either as a concurrent, sequential, or intermittent treatment regime, involving a compound of Formula I and one or more of: selective estrogen receptor modulators (SERMs), estrogen, ER agonists, ER antagonists, selective androgen receptor modulators (SARMs), gonadotropin-releasing hormone (GnRH) agonists, antagonists, progestrone (P$_4$), progestins, and other PR agonists and modulators.

DETAILED DESCRIPTION OF THE INVENTION

In one form the present invention provides novel compounds of Formula I

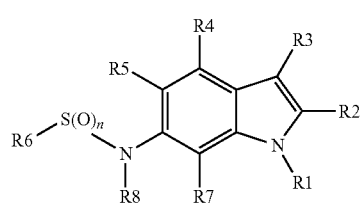

wherein:

n is 1 or 2;

R1 is selected from: $C_1$-$C_8$ alkyl, $C_2$-$C_6$ alkenyl, $C_2$-$C_6$ alkynyl, $C_1$-$C_6$ hydroxyalkyl, $C_1$-$C_6$ haloalkyl, $C_1$-$C_6$ cyanoalkyl, $C_1$-$C_6$ alkylaryl, $C_1$-$C_6$ alkylheteroaryl, $C_3$-$C_8$ cycloalkyl, $C_1$-$C_6$ alkylcycloalkyl, $C_1$-$C_6$ alkyldicycloalkyl, $C_1$-$C_6$ alkylheterocyclyl, heterocyclyl, aryl, heteroaryl, $C_1$-$C_6$ alkyl-O—R9, $C_0$-$C_6$ alkyl C(S)R9, $C_1$-$C_6$ alkylCO$_2$R9, —SO$_n$R11, wherein each of the cycloalkyl, heterocyclyl, aryl, and heteroaryl listed either singularly or in combination with an alkyl moiety are optionally substituted, with from one to three groups individually selected from: halo, —CN, —OH, oxo, $C_1$-$C_3$ alkyl, $C_1$-$C_3$ haloalkyl, $C_1$-$C_3$ cyanoalkyl, $C_2$-$C_5$ alkenyl, $C_0$-$C_3$ alkylNO$_2$, —OC$_1$-$C_3$ alkyl, $C_1$-$C_3$ hydroxyalkyl, $C_0$-$C_3$ alkylNR12R13, $C_0$-$C_3$ alkylC(O)R12, $C_0$-$C_3$ alkylC(O)OR12, C(O)NR12R13, C(S)NR12R13, CH$_2$OR12, —SR12, S(O)$_n$R12, —S(O)$_n$NR12R13, —N(R9)C(O)NR12R13, —N(R12)C(O)OR13, —N(R12)S(O)$_n$R13, —N(R12)S(O)$_n$NR12R13, —C=N—OR10, and -cyclo CN$_4$R9; provided that aryl and heteroaryl are not solely di, or tri substituted with alkoxy substituents;

R2 is selected from H, halo, —CN, $C_1$-$C_6$ alkyl, $C_1$-$C_6$ haloalkyl, $C_3$-$C_6$ cycloalkyl, $C_2$-$C_4$ alkenyl, $C_2$-$C_4$ alkynyl;

R3 is selected from an optionally substituted aryl, an optionally substituted heteroaryl, or an optionally substituted bicyclic heteroaryl; wherein the substituted aryl, substituted heteroaryl, and bicyclic heteroaryl are substituted with from one to three groups individually selected from: halo, —CN, —OH, oxo, $C_1$-$C_3$ alkyl, $C_1$-$C_3$ haloalkyl, $C_1$-$C_3$ cyanoalkyl, $C_2$-$C_5$ alkenyl, $C_2$-$C_6$ alkynyl, $C_0$-$C_3$ alkylNO$_2$, —OC$_1$-$C_3$ alkyl, —OC$_1$-$C_3$ haloalkyl, $C_1$-$C_3$ hydroxyalkyl, $C_0$-$C_3$ alkylNR12R13, $C_0$-$C_3$ alkylC(O)R12, $C_0$-$C_3$ alkylC(O)OR12, —C(O)NR12R13, —C(S)NR12R13, —CH$_2$OR12, —SR12, —S(O)$_n$R12, —S(O)$_n$NR12R13, —N(R9)C(O)NR12R13, —N(R12)C(O)OR13, —N(R12)S(O)$_n$R13, —N(R12)S(O)$_n$NR12R13, —C=N—OR10 and -cyclo CN$_4$R9;

R4, R5, and R7 are each independently selected from: H, halo, —OH, —CN, $C_1$-$C_6$ alkyl, $C_1$-$C_6$ haloalkyl, $C_2$-$C_4$ alkenyl, $C_2$-$C_4$ alkynyl, —OC$_1$-$C_4$ alkyl, —OC$_1$-$C_4$ haloalkyl;

R6 is selected from: $C_1$-$C_6$ alkyl, $C_1$-$C_6$ haloalkyl, $C_2$-$C_6$ alkenyl, $C_3$-$C_8$ cycloalkyl, $C_1$-$C_6$ alkylcycloalkyl, heterocyclyl, $C_1$-$C_3$ alkylheterocyclyl, phenyl, $C_1$-$C_3$ alkylheteroaryl, $C_0$-$C_3$ alkylNR9R10, and —N(H)C(O)R9, wherein each of the cycloalkyl, heterocyclyl, phenyl, and heteroaryl listed either singularly or in combination with an alkyl moiety are optionally substituted with from one to three groups individually selected from halo, —CN, —OH, oxo, $C_1$-$C_3$ alkyl, $C_1$-$C_3$ haloalkyl, $C_1$-$C_3$ cyanoalkyl, $C_2$-$C_5$ alkenyl, $C_0$-$C_3$ alkylNO$_2$, —OC$_1$-$C_3$ alkyl, and $C_1$-$C_3$ hydroxyalkyl;

R8 is selected from: H, $C_1$-$C_4$ alkyl;

R9 is individually selected from: H, $C_1$-$C_6$ alkyl, $C_1$-$C_6$ haloalkyl, $C_0$-$C_6$ alkylheterocyclyl, $C_1$-$C_6$ alkylcycloalkyl; $C_1$-$C_6$ alkylaryl, $C_0$-$C_6$ alkylheteroaryl, $C_1$-$C_6$ hydroxyalkyl, $C_2$-$C_6$ alkenyl, $C_3$-$C_8$ cycloalkyl;

R10 is selected from H, $C_1$-$C_6$ alkyl, and $C_3$-$C_8$ cycloalkyl;

R11 is selected from: $C_1$-$C_6$ alkyl, —NR9R9, $C_0$-$C_6$ alkylcycloalkyl, aryl, heteroaryl, wherein the aryl and heteroaryl groups are optionally substituted with from 1 to 3 groups individually selected from halo, —CN, and —OC$_1$-$C_3$ alkyl;

R12 and R13 are individually selected from: H, $C_1$-$C_6$ alkyl, $C_1$-$C_6$ haloalkyl, $C_1$-$C_6$ alkylcycloalkyl; $C_1$-$C_6$ alkylaryl, $C_0$-$C_6$ alkylheteroaryl, $C_1$-$C_6$ hydroxyalkyl, $C_2$-$C_6$ alkenyl, and $C_3$-$C_8$ cycloalkyl;

or a pharmaceutically acceptable salt thereof.

In one form, More preferred groups for R1 include: $C_1$-$C_6$ alkyl, $C_1$-$C_6$ alkenyl, $C_1$-$C_6$ alkynyl, $C_1$-$C_6$ haloalkyl, $C_3$-$C_8$ cycloalkyl, $C_1$-$C_6$ alkylcycloalkyl, aryl, $C_1$-$C_6$ alkylaryl, heteroaryl, $C_1$-$C_6$ alkyl heteroaryl, $C_1$-$C_6$ alkylheterocyclyl, —SO$_n$R11, and $C_1$-$C_6$alkyl-S—R9, wherein each of the cycloalkyl, heterocyclyl, aryl, and heteroaryl, listed either singularly or in combination with an alkyl moiety is optionally substituted with from 1 to 3 groups individually selected from halo, —CN, OH, —NO$_2$, $C_1$-$C_3$ alkyl, $C_1$-$C_3$ haloalkyl, and $C_1$-$C_3$ hydroxyalkyl.

In another form, preferred R1 groups include: heterocyclyl, $C_1$-$C_6$ alkylheterocyclyl, aryl, $C_1$-$C_6$ alkylaryl, heteroaryl, and $C_1$-$C_6$ alkylheteroaryl, wherein each is optionally substituted with from 1 to 3 groups individually selected from halo, —CN, —OH, —NO$_2$, $C_1$-$C_3$ alkyl, $C_1$-$C_3$ haloalkyl, and $C_1$-$C_3$ hydroxyalkyl.

More Preferred groups for R3 include: benzo[1,3]dioxole, benzofuranyl, benzo[1,2,5]thiadiazolyl, benzothiophenyl, chromen-2-onyl, 2,3-dihydro-benzo[1,4]dioxinyl, 2,3-dihydro-benzofuranyl, 2,3-dihydro-1H-indolyl, 1,3-dihydro-benzoimidazol-2-onyl, 1,3,-dihydro-indol-2-onyl, furanyl, indan-1-onyl, indazolyl, isobenzofuran-1-onyl, isoxazolyl, napthalenyl, phenyl, pyrazolyl, pyridinyl, pyrimidyl, pyrrolyl, quinolinyl, 1,2,3,4-tetrahydro-quinolinyl, thiophenyl, thiazolyl, tetrahydrofuranyl, and tetrahydropyranyl, each optionally substituted with from 1 to 3 groups individually selected from: halo, —CN, —OH, —NO$_2$, $C_1$-$C_3$ alkyl, $C_1$-$C_3$ haloalkyl, $C_1$-$C_3$ hydroxyalkyl, —O $C_1$-$C_3$ alkyl, —C(S)NR9R9, —C=N—OH, —C=N—OR11, and C(O)R11.

More preferred R6 groups include: $C_1$-$C_6$ alkyl, $C_1$-$C_6$ haloalkyl, $C_1$-$C_6$ alkylheterocyclyl, $C_3$-$C_8$ cycloalkyl, $C_1$-$C_6$ alkylcycloalkyl, $C_2$-$C_6$ alkenyl, heterocyclyl, and $C_0$-$C_6$ alkylNR9R10. Still more, R6 groups include $C_1$-$C_6$ alkyl, $C_1$-$C_6$ alkylcycloalkyl, and heterocyclyl.

The present invention also contemplates within its scope the treatment and amelioration of non-malignant conditions such as myomas, leiomyomas (uterine fibroids), endometriosis (adenomyosis), postoperative peritoneal adhesions, and endometrial hyperplasia or pathological sequelae due to the above conditions.

The present invention also includes the treatment and/or amelioration of infertility; control of fertility; female sexual dysfunction; and gynecological or menstrual disorders or syndromes; such as, abnormal or dysfunctional bleeding, amenorrhea, menorrhagia, hypermenorrhoea, and dysmenorrhea or pathological sequelae due to the above diseases, disorders and/or syndromes.

The present invention also includes the treatment and/or amelioration of malignant conditions such as carcinomas and adenocarcinomas of the uterous, ovary, breast, colon, and prostate or pathological sequelae due to the above diseases, disorders and/or syndromes.

The term "modulation" would include, but not be limited to, up-regulation, down-regulation, inhibition, agonism, antagonism of the receptor as appropriate to achieve gene expression and the resulting biological sequelae from such intervention.

The phrase "diseases related to receptor-modulation" or "diseases mediated by receptor activity" refers to any physiological disorder of any origin, response to administration of a receptor modulator either as an agonist, antagonist, partial agonist or partial antagonist, and mixtures thereof.

In the structures illustrated herein the following indicates the atom or point of attachment of the illustrated group to the remaining portion of the molecule:

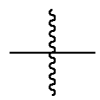

General chemical terms used in the description of compounds herein described bear their usual meanings. For example, the term "$C_{1-6}$ alkyl," or "($C_1$-$C_6$) alkyl" or "$C_1$-$C_6$ alkyl" refers to a straight or branched aliphatic chain of 1 to 6 carbon atoms. Unless otherwise stated, the term "alkyl" means $C_1$-$C_6$ alkyl. Unless specifically denoted to the contrary, the carbon atom of alkyl groups are attached to the rest of the referenced molecule. When used in conjunction with a substituent, the alkyl group can be an alkylene group linking the substituent to the rest of the referenced molecule. The term "$C_0$-$C_6$ alkyl" implies an alkyl group as indicated above, however when the term $C_0$ applies, the alkyl group is not present. In this embodiment, the remaining group(s) attach directly to the rest of the referenced molecule without the intermediacy of the linking, alkylene group.

The terms alkenyl and alkynyl, for example, a $C_2$-$C_6$ alkenyl group (or a $C_2$-$C_6$ alkynyl group) as used herein mean that the respective groups can include 1, 2, or 3 double bonds (or triple bonds). If more than one double or triple bond is present in the group, the double and triple bonds can be conjugated or non-conjugated.

The invention also contemplates that the terms "$C_1$-$C_6$ alkyl", "$C_2$-$C_6$ alkenyl" and similar terms also encompass the specified alkyl or alkenyl or similar moiety, which may be chiral, regio or steroisomeric. Such chiral or regio or stereoisomeric moieties as substituents are also included within the scope of the present invention.

The term "cycloalkyl" as used herein refers to a cyclic $C_3$-$C_8$ moiety having only carbon atoms as ring members and that each carbon atom ring member includes an appropriate number of hydrogen atoms or is optionally substituted with one or more substituents as described herein. It will be understood that the term also contemplates that that the ring can include one or more carbon-carbon double bonds.

The term "heterocycle", "heterocyclyl", or "heterocyclic" refers to a 5-10 membered mono or fused bicyclic ring, which may be saturated or partially unsaturated, and can contain 1-5 heteroatoms. The term "heteroatom" as used herein means an atom selected from N, S, or O. The heterocycle, heterocyclyl, or heterocyclic rings can optionally be substituted at the ring carbon, nitrogen, or sulfur atom(s) unless otherwise specified with one or more of the substituents listed below. The heterocyclic ring is attached to the referenced compound or substructure. In one form, mono heterocyclic rings are preferred. In another form, preferred heterocyclic groups include benzothiophene, dioxarane, hexamethyleneimmino, indolyl, isoquinolyl, morpholino, piperidinyl, pyridinyl, pyrrolidinyl, quinolyl, tetrazolyl, and thiomorpholino. As a corollary, the term "alkylheterocyclic" or "alkylheterocycle" is understood to mean that the alkyl group is attached to the heterocycle and the point of attachment to the rest of the referenced molecule or substructure is the alkyl group (or alkylene group).

The term "haloalkyl" as used herein refers to an alkyl group (as noted above) substituted with one or more halo atoms selected from F, Br, Cl, and I. In selected forms of the present invention, difluoroalkyls for example, difluoromethyl groups, —$CHF_2$, are preferred.

The term "hydroxyalkyl" as used herein refers to an alkyl group substituted with one or more hydroxyl groups where a carbon atom of the alkyl group is attached to the referenced molecule or portion thereof.

The term "alkoxy" or "—$OC_1$-$C_6$ alkyl" as used herein refers to an alkyl group attached to the referenced molecule or portion thereof via an oxygen atom.

The term "aryl" or "optionally substituted aryl" refers to a cyclic aromatic moiety. Illustrative aryl moieties include monocylic or bicyclic fused rings, such as but not limited to: phenyl, napthylene, phenanthrene, anthracene, and the like. When substituted, the aryl moiety can be substituted with one or more substituents listed below.

The term "phenyl" or "optionally substituted phenyl" refers to an aromatic moiety having 6 ring carbons with an appropriate number of hydrogen atoms. An optionally substituted phenyl moiety can have one or more substituents as listed below attached to the ring carbons.

The term alkylaryl refers to an alkyl moiety substituted by an aryl group (as described above). For example, $C_1$-$C_6$ alkylaryl indicates that an aryl group is attached to a $C_1$-$C_6$ alkyl moiety (or alkylene group) and that the resulting $C_1$-$C_6$ alkylaryl is attached to the rest of the referenced molecule via the alkyl moiety (or alkylene group). Benzyl is a preferred alkylaryl moiety.

The term "heteroaryl," or "heteroaromatic" refers to substituted or unsubstituted 5 to 10 membered ring(s) that is/are considered to exhibit aromatic character and have from 1 to 4 heteroatoms as ring members. Heteroaryl, or heteroaromatic rings as used herein include monocylic or bicyclic fused rings. As used in the present invention, for bicyclic heteroaryl or heteroaromatic fused rings, both rings do not have to be aromatic. For example, benzofused bicyclic rings are included within the terms heteroaryl and heteroaromatic rings. Unless specified to the contrary, the aromatic ring is directly attached to the referenced indole compound or substructure. Examples of heteroatoms include: O, S, and N. Illustrative examples of heteroaryls include but are not limited to: benzodioxolyl, benzimidazolyl, benzofuryl, benzothienyl, furyl, imidazolyl, imidazolidinone-yl, imidazolone-yl, imidazopyridinyl, indazolyl, indolyl, isothiazolyl, isobenzofuranyl, isoxazolyl, morpholinyl, oxadiazolyl, oxazolyl, quinyl, pyranyl, pyrazinyl, pyrazolyl, pyridazinyl, pyridyl, pyrimidinyl, pyrrolidinyl, pyrrolyl, tetrahydrofuranyl, tetrahydroquinolyl, tetrazolyl, thiadiazolyl, thiazolyl, triazinyl, 1,2,3-trazolyl, 1,2,4-triazolyl, triazolone-yl, thienyl, and isomers thereof. Unless specified to the contrary, the heteroaryl or heteroaromatic moiety, including the heteroatoms, can be substituted with one or more of the substitutents listed below.

Unless specifically noted to the contrary, the term "optionally substituted" or "substituted" when used with groups such as, aryl, heteroaryl, cycloalkyl, and/or heterocyclyl is intended to refer to the groups whether they are used individually or in conjunction with another group or moiety and means that the group is substituted with one or more substituents listed herein—typically, but exclusively by replacing one or more hydrogens. The substituents include: halo, —CN, —OH, oxo (=O), $C_1$-$C_3$ alkyl, $C_1$-$C_3$ haloalkyl, $C_1$-$C_3$ cyanoalkyl, $C_2$-$C_5$ alkenyl, $C_0$-$C_3$ alkyl$NO_2$, —$OC_1$-$C_3$ alkyl (or $C_1$-$C_3$ alkoxy), $C_1$-$C_3$ hydroxyalkyl $C_0$-$C_3$ alkylNR12R13, $C_0$-$C_3$ alkylC(O)R12, $C_0$-$C_3$ alkylC(O)OR12, —C(O)NR12R13, —C(S)NR12R13, —$CH_2$OR12, —SR12, —S(O)$_n$R12, —S(O)$_n$NR12R13, —N(R9)C(O)NR12R13, —N(R12)C(O)OR13, —N(R12)S(O)$_n$R13, —N(R12)S(O)$_n$NR12R13, —C=N—OR12, -cyclo$CN_4$R12 (optionally substituted tetrazole), where n=1 or 2 and where R12, and R13 are individually selected from: H, $C_1$-$C_6$ alkyl, $C_1$-$C_6$ haloalkyl, $C_1$-$C_6$ alkylcycloalkyl; $C_1$-$C_6$ alkylaryl, $C_0$-$C_6$ alkylheteroaryl, $C_1$-$C_6$ hydroxyalkyl, $C_2$-$C_6$ alkenyl, and $C_3$-$C_8$ cycloalkyl. Preferred substituents are selected from the group consisting of: F, Cl, —CN, —NO₂, CH₃, $C_1$-$C_3$ alkyl, —CF₃, —CHF₂, —CH₂CN, $C_2$-$C_4$ alkenyl, —C(O)R12, —C(O)OR12, —C(O)NR12R13, —C(O)H, —CH₂OR12, —OR12, —SR12, —NR12R13, and —C═N—OR12.

The term "Prodrugs" describes derivatives of the compounds of the invention that have chemically or metabolically cleavable groups and become by solvolysis or under physiological conditions the compounds of the invention, which are pharmaceutically active, in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy. In some cases it is desirable to prepare double ester type prodrugs such as (acyloxy) alkyl esters or ((alkoxycarbonyl)oxy)alkyl esters.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including but not limited to —OH, —NH, and COOH. Suitable protecting groups are known to one of skill in the art and are described in Protecting groups in Organic Synthesis, 3$^{rd}$ edition, Greene, T. W.; Wuts, P. G. M. Eds., John Wiley and Sons, New York, 1999.

As used herein, the term "solvate" refers to a crystal (or crystals) of a compound of the invention formed to include a stoichiometric or non-stoichiometric amount of the compound of Formula I and a solvent molecule. Typical solvating solvents include for example, water, methanol, ether, ethanol, ethyl acetate, acetone, acetonitrile, and dimethylformamide. When the solvent is water, the term hydrate for a stoichiometric or non-stoichiometric amount of compound and water (or hemi-hydrate for half the stoichiometric amount of water) may optionally be used.

In those instances where a compound of the invention possesses acidic or basic functional groups, various salts may be formed which are more water soluble and/or more physiologically suitable than the parent compound. Salts are conveniently prepared by methods known in the art for example, by treating an acidic compound with a base or by exposing the acidic compound to an ion-exchange resin. Included within the definition of pharmaceutically acceptable salts are the relatively non-toxic, inorganic and organic base or acid addition salts of compounds of the present invention (see, for example salts described in, S. M. Berge, et al., "Pharmaceutical Salts," *J. Phar. Sci.*, 66: 1-19 (1977) and "A Handbook of Pharmaceutical Salts Properties, Selection, and Use", Wermuth, C. G. and Stahl, P. H. (eds.) Verlag Helvtica Chimica Acta, 2002, which are incorporated herein). Common base addition salts include, for example, salts formed from: arginine, benethamine, benzathine, diethanolamine, diethylamine, ethylenediamine, meglumine, lysine, magnesium, piperazine, calcium, potassium, sodium, tromethamine, and zinc, as well as salts of ammonium, quaternary ammonium, and amine cations, derived from nitrogenous bases of sufficient basicity to form salts with the compounds of this invention. Moreover, the basic group(s) of the compound of the invention may be reacted with suitable organic or inorganic acids to form salts. Common acid addition salts include, for example: acetate, adipate, benzenesulfonate, benzoate, citrate, ethanesulfonate, fumarate, D-gluconate, bromide, chloride, lactate, lactobionate, maleate, methanesulfonic, napthalene-2-sulfonic, phosphoric, succinic, sulfuric, tartaric, and p-toluenesulfonic acid.

A compound as illustrated by Formula I may occur as any one of its stereochemical isomers, positional isomers, or regio-isomers, all of which are within the scope of the present invention of the invention. Certain compounds of the invention may possess one or more chiral centers, and thus, may exist in optically active forms. Additional asymmetric carbon atoms can be present in a substituent group such as an alkyl group. The R- and S-isomers and mixtures thereof, including racemic mixtures as well as mixtures of enantiomers or cis- and trans-isomers, are contemplated by this invention. Likewise, when the compounds contain an alkenyl, alkenylene, oximes, and O-alkylated oxime group, there exist the possibility of cis and trans isomeric forms of the compounds. All such isomers as well as the mixtures thereof are intended to be included in the invention. If a particular stereoisomer is desired, it can be prepared by methods well known in the art by using stereo-specific reactions with starting materials that contain the asymmetric centers and are already resolved. Alternatively desired stereoisomers may be prepared by methods that lead to mixtures of the stereoisomers and subsequent resolution by known methods. For example, a racemic mixture may be reacted with a single enantiomer of some other compound i.e. a chiral resolving agent.

Reference will now be made to preferred compounds of the present invention, which are illustrated by Formula I

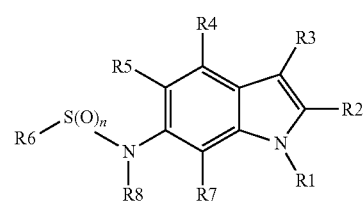

where
n is 1 or 2 and R1-R8 are as described herein, and pharmaceutically acceptable salts of Formula I.

The compounds of the present invention that are specifically exemplified and/or described herein are named and numbered using the "AUTONOM" for ISIS/Draw version 2.5 SP1 or CHEMDRAW ULTRA AUTONOM versions 7.0.1. Preferred compounds of the invention are listed in the following Tables included herein and can also include pharmaceutically acceptable salts solvates, enantiomer, racemates, diastereomers and mixtures of diastereomers thereof.

The geometric isomers associated with the double bonds and the optical isomers associated with asymmetric carbon atoms of compounds of Formula I are also contemplated to be within the scope of the current invention as useful for the treatment of diseases related to PR receptor modulation.

General Synthesis of Indole Intermediates for Use in the Present Invention

The compounds of the instant invention can be synthesized as exemplified in the following Schemes, Examples, and general procedures. However, the following discussion is not intended to limit the scope of the present invention in any way because one of skill in the art is able to extrapolate without undue experimentation from the Schemes and examples herein to other specific compounds within the scope of the invention. Many of the reagents and starting materials can be readily obtained from commercial suppliers or are readily available to one of ordinary skill in the art. Other necessary reagents and starting materials may be made by procedures which are selected from standard techniques of organic and heterocyclic chemistry, techniques which are analogous to the syntheses of known similar reagents or starting materials, and the procedures described in the preparations and examples below, including any novel procedures. The R1, R1, R2, R3, R4, R5, R6, etc, designations used within immediately following section are for the purpose of illustrating the various methods of synthesizing compounds of the invention and/or illustrating variability of substituents at the pendent position and are not necessarily synonymous in scope or meaning with similar groups used in the generic structure for compounds of Formula I. However, groups in final compounds of the schemes occupying similar positions are co-extensive in scope and meaning compared to groups occupying similar positions as defined for the generic structure of compounds of Formula I. Specific examples of each of the Methods listed in the Schemes 1-5 are described. It will be understood that the conditions i.e., specific temperature (ranges), solvents, reaction times, and the like, can be modified by those skilled in the art to provide all of the specific compounds as described herein. Consequently the Methods and examples provide general procedures that can be used to prepare compounds of the present invention.

The following terms and abbreviations are used as herein defined.

| DAST | diethylaminosulfur trifluoride |
| DEAD | diethyl azodicarboxylate |
| DIAD | diisopropyl azodicarboxylate |
| DPDB | (diphenylphosphino)-2'-(N,N-dimethylamino)biphenyl |
| DMF | N,N-dimethylformamide |
| DMSO | dimethylsulfoxide |
| DMAP | N',N'-dimethylaminopyridine |
| $Pd_2(dba)_3$ | Tris(dibenzylidineacetone)dipalladium |
| $PdCl_2(dppf)_2$ | palladium chloride bis(diphenylphosphino ferrocene) |
| EtOAc | ethyl acetate |
| $Et_2O$ | diethyl ether |
| FC-1032 resin | polystyrene anchored-$(PPh_2)Pd[P(t-Bu)_3]Cl_2$ a Pd catalyst from Johnson Mathey Catalysis and Chrial Technologies |
| H NMR | means that the observed H NMR is consistent with the illustrated structure |
| HMDS | hexamethyldisilazane |
| KOAc | potassium acetate |
| LRMS | low resolution mass spectrum |
| LiHMDS | lithium hexamethyldisilazide |
| NaHMDS | sodium hexamethyldisilazide |
| NBS | N-bromosuccinamide |
| RT | room temperature |
| THF | tetrahydrofuran |
| TBAF | tetrabutylammonium fluoride |
| $PCy_3$ | tricyclohexyl phosphine |
| Ts | tosylate (p-toluenesulfonyl) |
| TsCl | p-toluenesulfonyl chloride |
| X | as used herein refer to halides, i.e., I, Br, Cl, or F |

Scheme 1 below, illustrates general synthetic strategies for preparing certain indole intermediates, which can be used to synthesis 6 sulfonamide compounds in accordance with the present invention. Examples of preparations of specific compounds are provided below both in the written examples and Tables. The "Methods" listed in bold text used (in addition with the reagents) in the Schemes are described in more detail in the written examples. The procedures described for these "Methods" can be used as general procedures to prepare the compounds exemplified herein.

Scheme 1

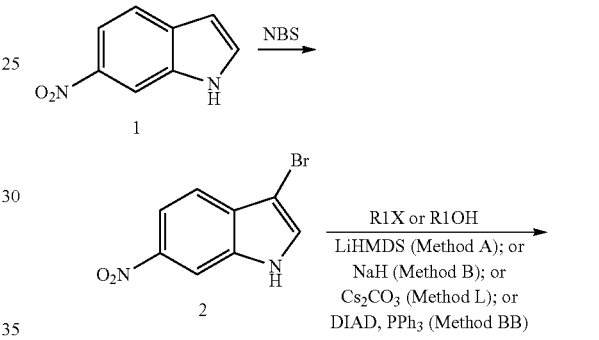

X = Cl, Br or I

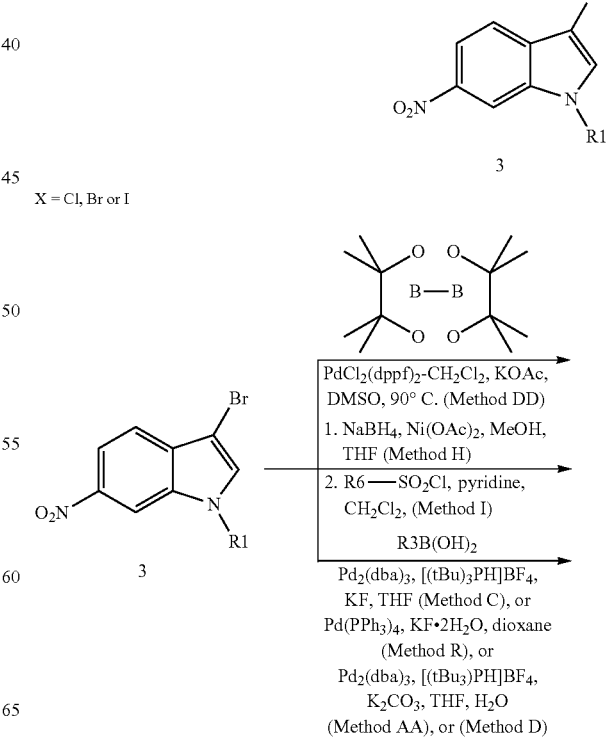

-continued

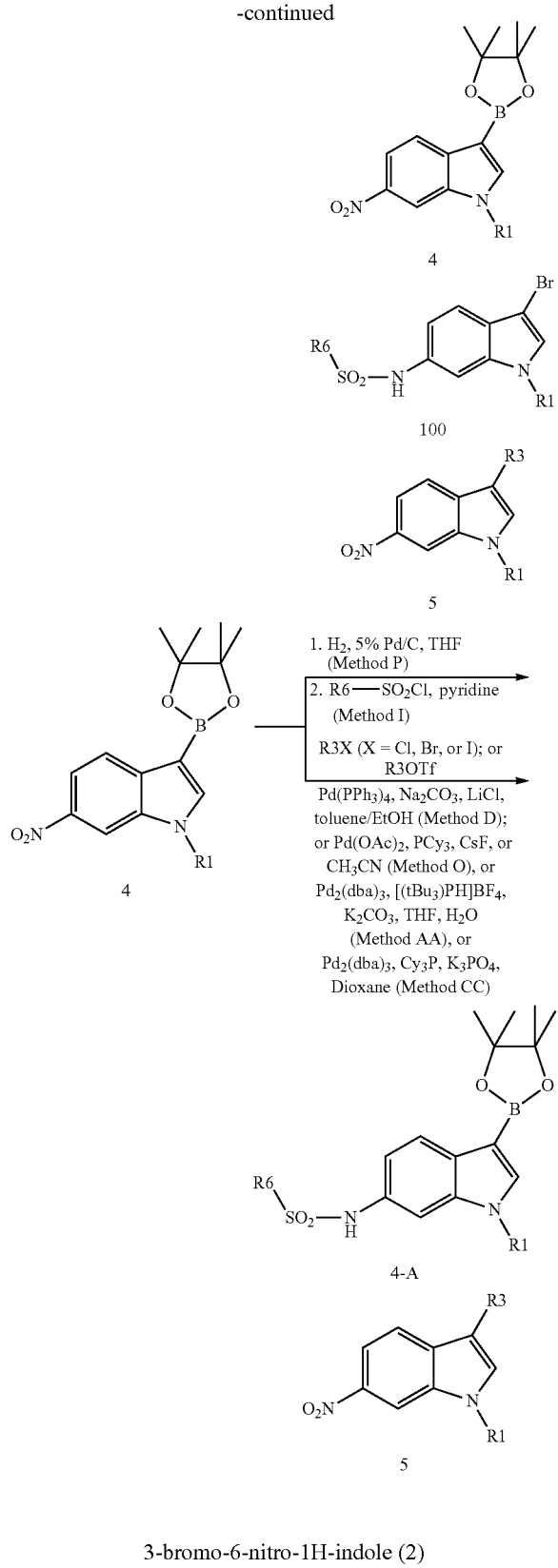

3-bromo-6-nitro-1H-indole (2)

Add N-bromosuccinamide (NBS) to 6-nitroindole 1 (22.72 g, 140.12 mmol) dissolved in tetrahydrofuran (600 mL) and allow the resulting mixture to stir for 18 hours. Quench the reaction mixture with saturated aqueous sodium thiosulfate solution (600 mL), dilute with ethyl acetate (EtOAc) (600 mL), and separate the layers. Sequentially, wash the organic layer with saturated aqueous sodium bisulfate (100 mL), saturated aqueous sodium bicarbonate (100 mL), water (100 mL), and brine (100 mL). Dry the resulting organic layer over $Na_2SO_4$ and filter. Concentrate the filtrate to give a yellow solid. Recrystallize the solid from dichloromethane and hexane to give 29.21 g of the title compound (86%). LRMS (API ES+)=263.0 (M+Na).

3-bromo-1-methyl-6-nitro-1H-indole (3, R1=Me)

Method A Add 1M lithium hexamethyldisilazide in tetrahydrofuran (31.2 mL, 31.17 mmol) and methyl iodide (2.6 mL, 41.56 mmol) to a solution of 3-bromo-6-nitro-1H-indole 2 (5.01 g, 20.78 mmol) in N,N-dimethylformamide (100 mL) at 0° C. Warm the reaction mixture to room temperature and allow it to stir for 5 hr. Quench with saturated aqueous ammonium chloride (100 mL), dilute with ethyl acetate (200 mL), and separate the layers. Sequentially, wash the organic layer with 10% aqueous lithium chloride (75 mL), saturated aqueous sodium bicarbonate (75 mL), water (75 mL×2), and brine (75 mL). Dry the resulting organic layer over $Na_2SO_4$ and filter. Concentrate the filtrate to provide a residue. Adsorb the residue with the crude product onto silica gel. Chromatograph the residue on a silica gel column eluting with dichloromethane in hexane (5-50 v/v %) to give 4.13 g of the title compound (78%). LRMS (API ES+)=255.0 (M+H).

3-bromo-1-isopropyl-6-nitro-1H-indole (3', R1=i-Pr)

Follow the procedure above (Method A), for 3-bromo-1-methyl-6-nitro-1H-indole, 3, with the following modifications: Use isopropyl iodide instead of methyl iodide and allow the reaction mixture to stir at room temperature for 18 hours. Thereafter add 1M lithium hexamethyldisilazide in tetrahydrofuran (15.5 mL, 15.5 mmol) and isopropyl iodide (2.1 mL, 20.74 mmol). Warm the resulting mixture to 40° C. and allow it to stir for 6 hours. Cool the mixture to room temperature and purify the product as above to give 4.37 g of the title compound (74%). LRMS (API ES+)=285.0 (M+H).

3-bromo-1-isobutyl-6-nitro-1H-indole (3", R1=i-Bu)

Method B Add NaH (1.2 eq) to a solution of 3-bromo-6-nitroindole 2 (15 g, 62 mmol) in 250 mL DMF. Allow the reaction mixture to stir for 1 hr and then add isobutyl iodide (17.2 mL, 149 mmol, 2.4 eq). Allow this solution to stir at ambient temperature. When the red color associated with the anion turns to brown, add more NaH and isobutyl iodide until most of the starting material is consumed. Add 600 mL of 5 M NaOH and extract 2×200 mL of ether ($Et_2O$). This provides a three-layer solution with the product in the $Et_2O$ layer and the starting material in the middle, aqueous/DMF layer. Combine the $Et_2O$ extracts and wash with 5 M NaOH, water (2×) and brine. Dry the organic layers over $Na_2SO_4$ filter, and concentrate. Recrystallize from $CH_2Cl_2$/hexanes to yield 15.73 g, 52.9 mmol, 85% of the title compound. $^1H$ NMR ($CDCl_3$) δ 8.28 (d, 1H, J=2.2 Hz), 8.04 (dd, 1H, J=1.8, 8.8 Hz), 7.59 (d, 1H, J=8.8 Hz), 7.35 (s, 1H), 3.96 (d, 2H, J=8.8 Hz), 2.18 (m, 1H), 0.93 (d, 6H, J=6.6 Hz).

Alternatively the R1 substituent can be attached to the indole N1 position using Method L described below for 4-[1-(3-Methyl-butyl)-6-nitro-1H-indol-3-yl]-benzonitrile (11, R1=i-Pr).

The following two methods illustrate yet alternative synthetic procedures to provide intermediate indole 3.

3-Bromo-1-[(S)-sec-butyl]-6-nitro-1H-indole (3''', R1=(S)-sec-Bu)

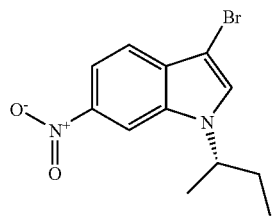

Method BB Add triphenylphosphine (19.04 g, 72.60 mmoles) and (R)-2-butanol (6.14 mL, 66.38 mmoles) to a dichloromethane (400 mL) solution containing 3-bromo-6-nitro-1H-indole (10.00 g, 41.49 mmoles). Cool this mixture to 0° C., and while stirring add diisopropyl azodicarboxylate (13.98 mL, 70.53 mmoles) as a solution in dichloromethane (50 mL) over a period of 45 min. After the addition is complete remove the ice bath and allow the reaction to stir for 3.5-4 hr at ambient temperature. Concentrate the crude reaction mixture in vacuo and purify the resulting oil via flash chromatography (silica gel, load 30% $CH_2Cl_2$/Hexane; run 15%-35% $CH_2Cl_2$ gradient in hexane). To obtain 8.83 g (72%) of product as a yellow crystalline solid. $^1$H NMR ($CDCl_3$) δ 8.34 (d, 1H, J=2.0 Hz), 8.04 (dd, 1H, J=8.8, 2.0 Hz), 7.59 (d, 1H, J=8.8 Hz), 7.45 (s, 1H), 4.47 (sextet, 1H, J=6.9 Hz), 1.89 (quintet, 2H, J=6.9 Hz), 1.53 (d, 3H, J=6.9 Hz), 0.84 (t, 3H, J=7.5 Hz); MS (API ES+) m/e 297 (M+1, $^{79}$Br), 299 (M+1, $^{81}$Br).

3-Bromo-1-[(R)-sec-butyl]-6-nitro-1H-indole (3$^{iv}$, R1=(R)-sec-Bu);

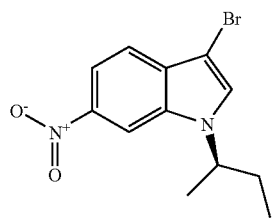

Method BB Add triphenylphosphine (20.64 g, 78.69 mmoles and (S)-2-butanol (6.11 mL, 66.52 mmoles) to a dichloromethane (400 mL) solution containing 3-Bromo-6-nitro-1H-indole (10.02 g, 41.57 mmoles). Cool this mixture to 0° C., and while stirring add diisopropyl azodicarboxylate (10.71 mL, 54.02 mmoles) as a solution in dichloromethane (20 mL) over a period of 15 min. After the addition is complete remove the ice bath and allow the reaction to stir for 3.5-4 hr at ambient temperature. Concentrate the crude reaction mixture in vacuo and then purify the resulting oil via flash chromatography (silica gel, load 30% $H_2Cl_2$/Hexane; ran 15%-35% $CH_2Cl_2$ gradient in hexane) to obtained 8.46 g (68%) of product as a yellow crystalline solid. $^1$H NMR ($CDCl_3$) δ 8.34 (d, 1H, J=2.0 Hz), 8.04 (dd, 1H, J=8.8, 2.0 Hz), 7.59 (d, 1H, J=8.8 Hz), 7.45 (s, 1H), 4.47 (sextet, 1H, J=6.9 Hz), 1.89 (quintet, 2H, J=6.9 Hz), 1.53 (d, 3H, J=6.9 Hz), 0.84 (t, 3H, J=7.5 Hz); MS (API ES+) m/e 297 (M+1, $^{79}$Br), 299 (M+1, $^{81}$Br).

1-Isopropyl-6-nitro-3-(4,4,5,5-tetramethyl-[4,3,2] dioxaborolan-2-yl)-R-indole (4, R1=i Pr)

Method DD Charge a 500 mL flask with vacuum dried potassium acetate (37.50 g, 382.00 mmol), 3-bromo-1-isopropyl-6-nitro-1H-indole, 3' (32.40 g, 114.50 mmol), bis(pinacolato)diboron (40.71 g, 160.00 mmol), $PdCl_2(dppf)_2.CH_2Cl_2$ (12.75 g, 15.64 mmol), and anhydrous dimethyl sulfoxide (430 mL). Warm this mixture with an oil bath to 85° C. and allow the mixture to stir overnight. Cool the dark colored reaction mixture to ambient temperature, quench with ample water and extract the resulting aqueous mixture with dichloromethane. Wash the combined extracts with water and brine. Dry the resulting organic layer over sodium sulfate, filter and concentrate the filtrate in vacuo. The resulting impure oil is purified by flash chromatography (silica gel; load 30% $CH_2Cl_2$/Hexane; run 2.5% to 20% ethyl acetate gradient in hexanes). The material from this column can be repurified by flash chromatography (silica gel, 30%-60% $CH_2Cl_2$ gradient in hexane) to provide the product (22.7 g, 60%) as a yellow crystalline solid. $^1$H NMR ($CDCl_3$) δ 8.32 (app. s, 1H), 8.03-8.04 (m, 2H), 7.90 (s, 13), 4.69-4.79 (m, 1H), 1.56 (d, 6H, J=6.7 Hz), 1.35 (br s, 12H); MS (API ES+) m/e 331 (M+1)

5-(1-isopropyl-6-nitro-1H-indol-3-yl)-pyridine-2-carbonitrile (5, R1=i-Pr, R3=2-cyanopyridine)

This compound was prepared from 1-isopropyl-6-nitro-3-(4,4,5,5-tetramethyl-[1,3,2]dioxaborolan-2-yl)-1H-indole (4, R1=i-Pr) and 5-bromo-2-cyanopyridine using Method D described below. LRMS (API ES+)=307.0 (M+H).

Alternatively the nitro group can be converted to the sulfonamide on the indole core to provide intermediates having the structure as compound 100 in Scheme 1 above using either Method H and Method I for 6-amino-1-isopropyl-3-(3,4,5-trifluoro-phenyl)-1H-indole and N-[1-Isopropyl-3-(3,4,5-trifluoro-phenyl)-1H-indol-6-yl]-methanesulfonamide (6, R1=i-Pr, R3=3,4,5-trifluoro-phenyl, R6=Me), respectively, described below.

4-(1-isopropyl-6-nitro-1H-indol-3-yl)-benzonitrile (5, R1=i-Pr, R3=4-benzonitrile)

Method C Combine 3-bromo-1-isopropyl-6-nitro-1H-indole, 3', (350 mg, 1.24 mmol), tris-(dibenzylideneacetone) di-palladium (0) (110 mg, 0.12 mmol), tri-t-butyl phosphonium tetrafluoroborate (70 mg, 0.24), 4-cyanophenylboronic acid (364 mg, 2.48 mmol), potassium fluoride (216 mg, 3.72 mmol) and tetrahydrofuran (6 mL) under a nitrogen atmosphere in a 50 mL flask. Heat the reaction mixture to 40° C. for 18 hours. Cool the reaction mixture to room temperature and filter through a celite pad. Wash the celite pad with ethyl acetate (200 mL). Then collect and concentrate the filtrates. Purify by precipitating or crystallizing from ethyl acetate to give 260.2 mg of the title compound (69%). LRMS (API ES+)=306.0 (M+H).

Method R: Add $Pd(PPh_3)_4$ (58 mg, 0.05 mmol) to a suspension of 3-bromo-1-isopropyl-6-nitro-1H-indole (3', R1=i-Pr) (194.5 mg, 0.5 mmol), arylboronic acid (0.75 mmol) and $KF.2H_2O$ (141 mg, 1.5 mmol) in 5 mL of [1,4]dioxane under $N_2$. Heat the reaction mixture to 80° C. and stir it at that temperature overnight. Evaporate the solvent vacuum. Dissolve the residue in ethyl acetate (10 mL), then wash with water (5 mL). Concentration the organic layer and purify using column chromatography give desired compounds (50-80%).

2-Fluoro-4-(6-nitro-1H-indol-3-yl)-benzonitrile (9F)

A. Dissolve 2-Fluoro-4-bromobenzonitrile (200 g, 990 mmol, 1.00 eq.) and triisopropyl borate (228 g, 1188 mmol, 1.2 eq.) in 700 mL of THF and 1400 mL of toluene. Cool the mixture with a dry ice/acetone bath to an internal temperature of −75° C. Slowly add n-BuLi (396 mL of a 2.5 M solution in hexanes) over a period of 2 hours. After addition is complete, a light-red, thin slurry occurs. Let the solution stir at −74° C. for 15 minutes, allow the solution to warm to −20° C. and then quench with 1500 mL of 2.5 M HCl. Let the solution warm to RT. Separate layers, extract the aqueous layer with EtOAc, dry the combined organic phases with $Na_2SO_4$, filter and concentrate in vacuo to yield a light-brown solid. Triturate the solid with hexane and transfer to a scintered glass funnel. Rinse with hexane one more time to obtain a pale-yellow filtrate. Stir the light-brown solid with cold $CH_2Cl_2$ and filter. Rinse with a small volume of $CH_2Cl_2$ to yield an off-white solid and a brown filtrate. Dry the solid in a vacuum oven at 40° C. and dried to yield 112 g (679 mmol, 69%) of 3-fluoro-4-cyanophenylboronic acid as an off-white solid.

B. 4-(1-Benzenesulfonyl-6-nitro-1H-indol-3-yl)-2-fluorobenzonitrile from 1-benzenesulfonyl-3-bromo-6-nitro-1H-indole, 7, and 3-fluoro-4-cyanophenylboronic acid using Method AA: $Pd_2(dba)_3$, [(t-$Bu_3$)PH]$BF_4$, $K_2CO_3$, THF, $H_2O$. Purify by precipitation from EtOAc/hexanes. Remove the benzenesulfonyl protecting group using TBAF and THF as described for 4-(6-nitro-1H-indol-3-yl)-benzonitrile (9) below. LRMS (API ES−)=280.0 (M−1).

1-Isopropyl-3-(4,4,5,5-tetramethyl-[1,3,2]dioxaborolan-2-yl)-1H-indol-6-ylamine Method P Add a solution of 1-isopropyl-6-nitro-3-(4,4,5,5-tetramethyl-[1,3,2]dioxaborolan-2-yl)-1H-indole, (4, R1=i-Pr) (14.48 g, 43.88 mmol) in ethanol to a suspension of 5% palladium on carbon (1.44 g) and ethanol in a Parr reaction bottle. Place the contents of the reaction bottle under a hydrogen atmosphere (60 psi) and shake on a Parr shaker at room temperature for 18 hr. After 18 hr, filter the contents of the reaction vessel through a pad of Celite, and concentrate the resulting filtrate in vacuo. The resulting crude, light-pink, crystalline material (11.84 g, 90%) can be used without further purification. $^1$H NMR (DSMO-$d_6$) δ 7.39 (s, 1H), 7.39 (d, 1H, J=8.3 Hz), 6.54 (d, 1H, J=1.8 Hz), 6.41 (dd, 1H, J=8.3 Hz, 1.8 Hz), 4.73 (br s, 2H), 4.37 (septet, 1H, J=6.8 Hz), 1.37 (d, 6H, J=6.8 Hz), 1.23 (br s, 12H); MS (API ES+) m/e 301 (M+1).

N-[1-Isopropyl-3-(4,4,5,5-tetramethyl-[1,3,2]dioxaborolan-2-yl)-1H-indol-6-yl]-methanesulfonamide (4-A, R1=i Pr, R6=Me)

Method I Charge a round bottom flask with 1-isopropyl-3-(4,4,5,5-tetramethyl-[1,3,2]dioxaborolan-2-yl)-1H-indol-6-ylamine (11.83 g, 39.43 mmol), dichloromethane (400 mL) and pyridine (6.40 mL, 78.87 mmol). Cool the resulting solution to 0° C., while stirring slowly add methanesulfonyl chloride (12.20 mL, 157.73 mmol). Allow the reaction to stir overnight and reach ambient temperature. Quench the reaction with saturated aqueous sodium bicarbonate. Extract the resulting aqueous layer with dichloromethane. Combine the combined extracts and wash the combined extracts with saturated aqueous sodium bicarbonate, water and brine, dry over sodium sulfate and concentrate in vacuo. Purify the resulting solid on a by flash chromotography (silica gel; 65%-100% dichloromethane gradient in hexane then gradient to 2.5% ethyl acetate in dichloromethane) to provide 12.0 g (80%) of the product as a light pink solid foam. $^1$H NMR (CDCl$_3$) δ7.96 (d, 1H, J=8.4 Hz), 7.69 (s, 1H), 7.39 (d, 1H, J=1.9 Hz), 6.88 (dd, 1H, J=8.4 Hz, 1.9 Hz), 6.38 (br s, 1H), 4.56 (septet, 1H, J=6.8 Hz), 2.91 (s, 3H), 1.49 (d, 6H, J=6.8 Hz), 1.34 (s, 12H); MS (IS−) m/e 377 (M−1).

1-isopropyl-6-nitro-3-(3,4,5-trifluoro-phenyl)-1H-indole (5, R1=i-Pr, R3=3,4,5-trifluoro-phenyl)

Method D Combine 1-isopropyl-6-nitro-3-(4,4,5,5-tetramethyl-[1,3,2]dioxaborolan-2-yl)-1H-indole (4, R1=i-Pr) (328 mg, 0.98 mmol), lithium chloride (125 mg, 2.94 mmol), 3,4,5-trifluorobromobenzene (240 μL, 1.96 mmol), toluene (4 mL), ethanol (4 mL) and 2M aqueous sodium carbonate (1.7 mL, 3.43 mmol) in a 50 mL flask fitted with a reflux condenser. Place the flask under a nitrogen atmosphere and add tetrakis(triphenylphosphine) palladium(0) (58 mg, 0.05 mmol). Heat the reaction mixture to reflux for 4 hours, then cool to room temperature. Filter the solution through a celite pad and wash the pad with ethyl acetate (50 mL). Wash the combined filtrates with saturated aqueous sodium bicarbonate (20 mL), water (20 mL), brine (20 mL). Dry the resulting organic solution over Na-2SO$_4$ and filter. Concentrate the filtrate, and adsorb the resulting residue onto silica gel. Chromatograph the residue on a silica gel column eluting with dichloromethane in hexane (2-50 v/v %) to give 140.7 mg of the title compound (43%). LRMS (API ES+)=335.0 (M+H).

4-(1-isopropyl-6-nitro-1H-indol-3-yl)-phthalonitrile (5, R1=i-Pr, R3=phthalonitrile)

Method O Place 1-isopropyl-6-nitro-3-(4,4,5,5-tetramethyl-[1,3,2]dioxaborolan-2-yl)-1H-indole 4 (107 mg, 0.324 mmol), 4-iodophthalonitrile (246 mg, 0.968 mmol), Pd(OAc)$_2$ (11 mg, 0.049 mmol) and tricyclohexylphosphine (22 mg, 0.078 mmol) in a 50 mL under an atmosphere of nitrogen. Add acetonitrile (4 mL) and bubble nitrogen through the solution for 15 min. Add cesium fluoride (446 mg, 2.936 mmol), place the reaction vessel in an oil bath that is pre-heated to 90° C. and stir for 30 min. Cool reaction to room temperature and pour into water (15 mL) and extract the aqueous with $CH_2Cl_2$ (2×15 mL). Dry the resulting organic solution over Na$_2$SO$_4$, filter and concentrate in vacuo. Triturate the resulting residue with $CH_2Cl_2$ and hexanes to afford 102 mg of the title compound (95%) as a yellow solid. $^1$H NMR (DMSO-$d_6$) δ8.705 (s, 1H), 8.640 (d, 1H, J=2.1 Hz), 8.506 (d, 1H, J=1.8 Hz), 8.280 (dd, 1H, J=1.8, 8.5 Hz), 8.191 (d, 1H, J=9.1 Hz), 8.137 (d, 1H, J=8.5 Hz), 8.015 (dd, 1H, J=2.1, 9.1 Hz), 5.072 (quin., 1H, J=6.7 Hz), 1.511 (d, 6H, J=6.7 Hz).

4-(1-isopropyl-6-nitro-1H-indol-3-yl)-3-methyl-5-carbonitrile-thiophen-2-yl (5, R1=i-Pr, R3=3-methyl-5-carbonitrile-thiophen-2-yl)

Method AA Combine 1-isopropyl-6-nitro-3-(4,4,5,5-tetramethyl-[1,3,2]dioxaborolan-2-yl)-1H-indole (4, R1=i-Pr) (1.1 g, 1.00 equiv; 3.5 mmoles), 5-bromo-4-methyl-2-thiophene carbonitrile (0.7 g; 1.00 equiv; 3.5 mmoles), and potassium carbonate (1.0 g, 2.2 equiv; 7.6 mmoles) in THF (10 mL) and water (5 mL). Sparge the mixture with N$_2$ for 20 minutes with a constant stream of sub-surface $N_2$. Then add tris(dibenzylideneacetone)dipalladium (0) (158 mg, 0.05 equiv; 170 μmoles) and tri-t-butylphosphonium tetrafluoroborate (101 mg, 0.1 equiv, 350 μmoles) and heat the mixture to 40° C. sealed under $N_2$ Monitor the reaction using TLC (30% EtOAc/hex); when no starting material remains, cool the mixture to room temperature and add 10 mL ethyl acetate. Wash the mixture with water, then brine and dry over $MgSO_4$. Remove $MgSO_4$ by filtration, and concentrate the filtrate in vacuo to yield a solid. Recrystallize the solid from dichloromethane/hexanes. Yield 0.789 g (70%). LRMS (API ES+)=326.0 (M+H).

1-Isopropyl-3-[5-(1-methyl-1H-tetrazol-5-yl)-thiophen-2-yl]-6-nitro-1H-indole

Method CC In a 501 mL flask fitted with a reflux condenser, combine 1-isopropyl-6-nitro-3-(4,4,5,5-tetramethyl-[1,3,2]dioxaborolan-2-yl)-1H-indole (4, R1=i-Pr) (700 mg, 2.1 mmol), 5-(5-Bromo-thiophen-2-yl)-1-methyl-1H-tetrazole (466 mg, 1.9 mmol), tris-(dibenzylideneacetone) di-palladium (0) (17 mg, 0.019 mmol), and tricyclohexylphosphine (13 mg, 0.0047 mmol) in dioxane (5.5 mL). Degas under nitrogen atmosphere three times; then add 1.3M aqueous potassium phosphate (2.5 mL, 3.2 mmol) in a 50 mL flask fitted with a reflux condenser. Heat the reaction mixture to 100° C. for 4 hours. Cool the reaction mixture to room temperature and dilute with water (20 mL) and ethyl acetate (20 mL); then separate layers. Extract the aqueous layer three times with ethyl acetate (10 mL). Combine the organics; dry over $MgSO_4$; remove the solids by filtration; and concentrate the filtrate in vacuo. Purify by silica gel column chromatograph eluting with ethyl acetate in hexanes to afford 0.3 g (39%) of the title material. $^1$H NMR ($CDCl_3$) δ 8.39 (s, 1H), 8.09 (d, 1H, J=9.1 Hz), 8.02 (d, 1H, J=9.1 Hz), 7.78 (d, 1H, J=3.9 Hz), 7.75 (s, 1H), 7.28 (d, 1H, J=3.9 Hz), 4.79 (quin., 1H, J=6.5 Hz), 4.37 (s, 3H), 1.62 (d, 6H, J=6.5 Hz).

General Synthesis of Indoles for Use in the Present Invention

Scheme 2 below illustrates further synthetic strategies for preparing indoles 6 from the indole intermediates prepared above. Some of the methods listed in bold in the Scheme are described above; other methods are described below after the Scheme.

Scheme 2

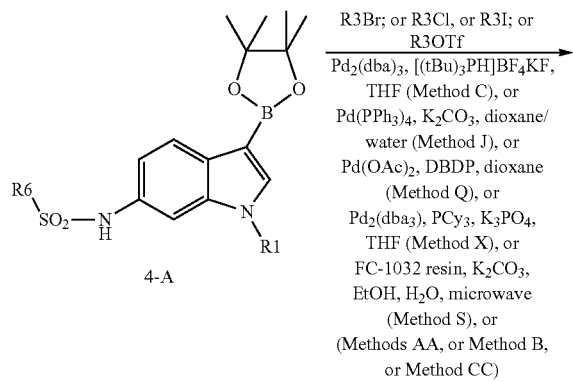

R3Br; or R3Cl, or R3I; or R3OTf
$Pd_2(dba)_3$, [(tBu)$_3$PH]BF$_4$KF, THF (Method C), or
Pd(PPh$_3$)$_4$, K$_2$CO$_3$, dioxane/water (Method J), or
Pd(OAc)$_2$, DBDP, dioxane (Method Q), or
$Pd_2(dba_3)$, PCy$_3$, K$_3$PO$_4$, THF (Method X), or
FC-1032 resin, K$_2$CO$_3$, EtOH, H$_2$O, microwave (Method S), or
(Methods AA, or Method B, or Method CC)

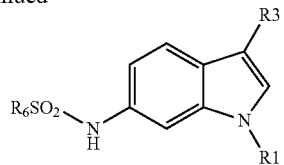

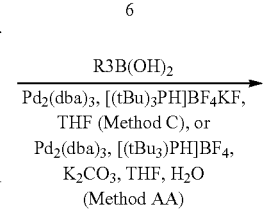

$R3B(OH)_2$
$Pd_2(dba)_3$, [(tBu)$_3$PH]BF$_4$KF, THF (Method C), or
$Pd_2(dba)_3$, [(tBu$_3$)PH]BF$_4$, $K_2CO_3$, THF, $H_2O$ (Method AA)

1. $H_2$, $PtO_2$, THF (Method E); or
1. $H_2$, 10% Pd/C, THF (Method F); or
1. $SnCl_2$—$2H_2O$, DMF, 60° C. (Method G); or
1. $NaBH_4$, Ni(OAc)$_2$, MeOH, THF (Method H)
2. R6—$SO_2Cl$, pyridine, $CH_2Cl_2$, (Method I)

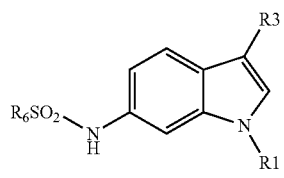

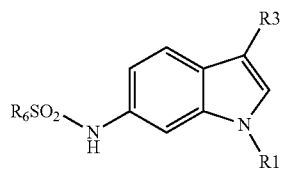

4-(6-amino-1-isopropyl-1H-indol-3-yl)-benzonitrile

Method E Place 4-(1-isopropyl-6-nitro-1H-indol-3-yl)-benzonitrile (4, R1=i-Pr, R3=4-benzonitrile) 250 mg, 0.82 mmol) in a 50 mL flask and add a suspension of platinum (II) oxide (16 mg) in tetrahydrofuran (9 mL). Place the reaction under 1 atmosphere of hydrogen and stir until the starting material is consumed. Filter through a celite pad and wash the pad with ethyl acetate (50 mL). Concentrate the combined filtrates to give 225.0 mg of the title compound (99%). LRMS (API ES+)=276.0 (M+H).

5-(6-amino-1-isopropyl-1H-indol-3-yl)-pyridine-2-carbonitrile

Method F This compound can be prepared from 5-(1-isopropyl-6-nitro-1H-indol-3-yl)-pyridine-2-carbonitrile (4, R1=i-Pr, R3=5-(2-cyanopyridine)) in a manner substantially similar to that described immediately above for 4-(6-amino-1-isopropyl-1H-indol-3-yl)-benzonitrile except Degussa type E101 NE/W 10% Palladium on activated carbon can be used instead of platinum (II) oxide in Method E. LRMS (API ES+)=277.0 (M+H).

5-(6-amino-1-isopropyl-1H-indol-3-yl)-thiophene-2-carbonitrile

Method G Add N,N-dimethylformamide (2 mL) and tin(II) dichloride dihydrate (992 mg, 4.40 mmol) to a 50 mL flask charged with 5-(1-isopropyl-6-nitro-1H-indol-3-yl)-thiophene-2-carbonitrile (4, R1=i-Pr, R3=2-cyano thiophene), (136.3 mg, 0.44 mmol) under a nitrogen atmosphere. Warm to 60° C. and stir for 45 minutes. Cool to room temperature and quench with saturated aqueous sodium bicarbonate (15 mL). Filter through a celite pad and wash pad with ethyl acetate (100 mL). Wash the combined filtrates with saturated aqueous sodium bicarbonate (20 mL), water (20 mL), brine (20 mL), dry ($Na_2SO_4$) and filter. Concentrate the filtrate to give 107.9 mg of the title compound (87%). LRMS (API ES+)=282.0 (M+H).

6-amino-1-isopropyl-3-(3,4,5-trifluoro-phenyl)-1H-indole

Method H Combine 1-isopropyl-6-nitro-3-(3,4,5-trifluoro-phenyl)-1H-indole (4, R1=i-Pr, R3=3,4,5-trifluoro-benzene) (136.1 mg, 0.41 mmol), nickel(II) acetate tetrahydrate (204 mg, 0.82 mmol), tetrahydrofuran (2.5 mL) and methanol (2.5 mL) in a 50 mL flask. Add sodium borohydride (62 mg, 1.64 mmol) in small portions. Once gas evolution is complete quench the reaction with saturated aqueous ammonium chloride (5 mL), dilute with ethyl acetate (10 mL), and separate the layers. Wash the organic layer with saturated aqueous sodium bicarbonate (5 mL), water (5 mL), brine (5 mL), dry ($Na_2SO_4$), filter and concentrate. This material may be used without further purification in the following preparation.

N-[1-Isopropyl-3-(3,4,5-trifluoro-phenyl)-1H-indol-6-yl]-methanesulfonamide (6, R1=i-Pr, R3=3,4,5-trifluoro-phenyl, R6=Me)

Method I Combine 6-amino-1-isopropyl-3-(3,4,5-trifluoro-phenyl)-1H-indole (116.6 mg, 0.38 mmol), prepared as described immediately above, dichloromethane (3.0 mL) and pyridine (62 µL, 0.76 mmol) under a nitrogen atmosphere in a 25 mL flask. Cool the reaction to 0° C. and add methane sulfonyl chloride (33 µL, 0.42 mmol). Allow the reaction to warm to RT while stirring for 3 hours. Quench reaction with saturated aqueous sodium bicarbonate (5 mL), dilute with ethyl acetate (10 mL) and separate the layers. Wash the organic layer with water (5 mL), brine (5 mL), dry ($Na_2SO_4$) and filter. Concentrate the filtrate and adsorb the crude product onto silica gel. Purify by silica gel chromatography eluting with ethyl acetate in dichloromethane (0-5 v/v %) to give 95.1 mg of the title compound (61%). LRMS (API ES+)=383.0 (M+H).

N-[3-(5-Chloro-thiophen-2-yl)-1-isopropyl-1H-indol-6-yl]-methanesulfonamide (6, R1=i-Pr, R3=5-chloro-thiophen-2-yl, and R6=methyl)

Method J Place N-[1-isopropyl-3-(4,4,5,5-tetramethyl-[1,3,2]dioxaborolan-2-yl)-1H-indol-6-yl]-methanesulfonamide (266 mg, 0.70 mmol), potassium carbonate (242 mg, 1.75 mmol), 2-bromo-5-chloro-thiophene (207 mg, 1.05 mmol), dioxane (6 mL) and water (1 mL), followed by addition of tetrakis(triphenylphosphine) palladium (0) (20 mg, 0.018 mmol) in a sealed tube under nitrogen. Heat the reaction mixture at 100° C. overnight, then cool to room temperature. Dilute the reaction mixture with ethyl acetate, and sequentially wash the resulting mixture with water and brine. Dry the organic layer over $MgSO_4$. Chromatograph the crude residue on silica gel column eluting with hexane and ethyl acetate (gradient) to give 89 mg (34%) of the title compound. $^1$H NMR ($CDCl_3$) δ 7.79 (d, 1H, J=8.8 Hz), 7.42 (d, 1H, J=1.8 Hz), 7.35 (s, 1H), 6.97 (dd, 1H, J=2.0, 8.6 Hz), 6.93 (d, 1H, J=4.0 Hz), 6.88 (d, 1H, J=4.0 Hz), 4.50-4.67 (m, 1H), 2.97 (s, 3H), 1.52 (d, 6H, J=6.6 Hz).

Alternatively the R3 substituent can be attached to the indole 3 position using Method Q described below for N-[3-(2-Cyano-phenyl)-1-isopropyl-1H-indol-6-yl]-methanesulfonamide (6, R1=i Pr, R3=2-cyano-phenyl, R6=Me).

N-[3-(2-Cyano-phenyl)-1-isopropyl-1H-indol-6-yl]-methanesulfonamide (6, R1=i Pr, R3=2-cyano-phenyl, R6=Me)

Method Q Add N-[1-isopropyl-3-(4,4,5,5-tetramethyl-[1,3,2]dioxaborolan-2-yl)-1H-indol-6-yl]-methanesulfonamide (50.0 mg, 0.132 mmoles), 4-bromo-3-methyl-benzonitrile (51.8 mg, 0.264 mmoles), $Pd(OAc)_2$ (4.25 mg, 0.018 mmoles; 4.25 mg), 2-(diphenylphosphino)-2'-(N,N-dimethylamino)biphenyl (11.5 mg, 0.030 mmoles), potassium phosphate (84.2 mg, 0.396 mmoles), and 1,4-dioxane (1.00 mL) to a 10 mL microwave vessel, equipped with a stir bar. Purge the reaction mixture with nitrogen, and then seal the vessel with a cap. Place the vessel in a microwave reactor at 150° C. for 15 min at 250 W heating. Monitor the reaction using LC/MS. Cool the reaction to ambient temperature and quench with saturated aqueous ammonium chloride. Extract the resulting mixture into ethyl acetate. Wash the combined extracts with saturated aqueous ammonium chloride, water and brine. Dry the resulting solution over sodium sulfate (granular) and concentrate in vacuo. Dissolve the resulting solid in dichloromethane and purify on a chromatotron (1MM silica gel plate) 0-2% ethyl acetate gradient in dichloromethane. A second purification may be necessary. This time purify the material with 30-40% ethyl acetate gradient in hexane to provide N-[3-(4-Cyano-2-methyl-phenyl)-1-isopropyl-1H-indol-6-yl]-methanesulfonamide, 35 mg (75%) as an off white solid. $^1$H NMR ($CDCl_3$) δ 7.58 (s, 1H), 7.45-7.52 (m, 3), 7.41 (d, 1H, J=8.4 Hz), 7.25 (s, 1H), 6.9 (dd, 1H, J=8.4, 1.7 Hz), 6.52 (s, 1H), 4.65 (septet, 1H, J=6.7 Hz), 2.98 (s, 3H), 2.34 (s, 3H), 1.55 (d, 6H, J=6.7 Hz); MS (IS−) m/e 377 (M−1).

N-[3-(2-thioamide-phenyl)-1-isopropyl-1H-indol-6-yl]-methanesulfonamide (6, R1=i Pr, R3=2-thioamide, R6=Me)

The cyano (or nitrile) substitutent of N-[3-(2-cyano-phenyl)-1-isopropyl-1H-indol-6-yl]-methanesulfonamide can be derivatized to a thioamide group using Lawesson reagent according to a modified procedure described in: Thomsen et al. *Org. Synth.* 1984, 62, 158; K. Clausen et al. *J. Chem. Soc. Perkin Trans. I.* 1984, 785; and Shabana, R.; Meyer, H. J.; and Lawesson, R.-O. *Phosphorus and Sulfur,* 1985, 25, 297.

Example 178

N-[3-(6-cyano-5-fluoro-pyridin-3-yl)-1-isopropyl-1H-indol-6-yl]-methanesulfonamide Method X Bubble $N_2$ through a mixture of N-[1-isopropyl-3-(4,4,5,5-tetramethyl-[1,3,2]dioxaborolan-2-yl)-1H-indo-6-yl]-methanesulfonamide (0.186 g, 0.493 mmol), 5-bromo-2-cyano-3-fluoropyridine (0.090 g, 0.448 mmol), $K_3PO4$ (1.3

M) (0.60 ml), and dioxane (1.2 ml) for 5 minutes. Add tricyclohexylphosphine (3.0 mg, 0.011 mmol) and $Pd_2(dba)_3$ (4.1 mg, 0.0045 mmol). Seal the tube and stir at 100° C. for 18 h. After cooling to room temperature, extract with EtOAc and wash with $NaHCO_3$. Dry the organic phase with $MgSO_4$. Purify the crude residue using silica gel chromatography to give 0.12 g (67% yield) of the title compound, MS: 373.0 (M+H)

N-[3-(3,5-Difluoro-4-hydroxymethyl-phenyl)-1-isopropyl-1H-indol-6-yl]-methanesulfonamide Method S: Weigh N-(3-Bromo-1-isopropyl-1H-indol-6-yl)-methanesulfonamide (100 mg, 0.302 mmol) and 2-fluoropyridine-4-boronic acid (42.5 mg, 0.302 mmol) into a 10 ml microwave vial. Add ethanol (4 ml) and the 1 N potassium carbonate solution (847.4 mg, 0.362 ml, 0.362 mmol). Add the FC-1032 resin (19.3 mg, 9.1 μmol, 0.47 mmol/g) and cap the vial. Microwave at 110° C. for 15 minutes. Filter the reaction, and concentrate in vacuo. Purify by Isco on silica (0-50% EtOAc/hexanes). Concentrate to afford the title compound (127 mg, 55%). $^1$H-NMR (DMSO) is consistent with product.

The syntheses of various substituents that can be attached to the indole 3 position or the N-1 position are described below.

3-Amino-5-bromo-pyridine-2-carboxylic acid amide: Add $NaBH_4$ (0.663 g, 17.5 mmol) in small portions to a methanol solution (50 mL) of 5-bromo-2-cyano-3-nitropyridine (2.00 g, 8.77 mmol) and nickel (II) acetate tetrahydrate (4.37 g, 17.5 mmol) at 0° C. After stirring at room temperature for 20 min, add water and EtOAc. Pass the mixture through a pad of celite. Extract with EtOAc. Dry the combined EtOAc extracts over MgSO4. Purify the crude product using silica gel chromatography to give 0.75 g (40% yield) of 3-amino-5-bromo-pyridine-2-carboxylic acid amide. MS 216.0/218.0 (M+H)

5-Bromo-3-fluoro-pyridine-2-carboxylic acid amide: Stir a solution of 3-Amino-5-bromo-pyridine-2-carboxylic acid amide (0.75 g, 3.47 mmol) and nitrosonium tetrafluoroborate (0.487 g, 4.16 mmol) in dichloromethane (50 ml) at 23° C. for 18 hours. Evaporate the solvent. Azeotrope the residue with toluene. Suspend the residue in toluene (20 ml) and reflux for 2 hours. Concentrate the mixture and purify the crude product by silica chromatography (10-100% EtOAc/Hexane) to afford 5-bromo-3-fluoro-pyridine-2-carboxylic acid amide (0.378 g, 50%). MS: M+H=221.0.

5-Bromo-2-cyano-3-fluoro-pyridine: Stir a mixture of 5-bromo-3-fluoro-pyridine-2-carboxylic acid amide (0.375 mg, 1.71 mmol) and NaCl (0.120 g, 2.05 mmol) in $CH_2Cl_2$ (20 ml). After 15 minutes, add $POCl_3$ (0.795 ml, 8.55 mmol) and reflux the mixture overnight. Cool the mixture to room temperature, and dilute with $CH_2Cl_2$; wash with saturated $NaHCO_3$ solution, dry over ($MgSO_4$). Purify the crude product using silica chromatography (0-50% EtOAc/Hexane) to produce 0.25 g (73% yield) of 5-bromo-2-cyano-3-fluoro-pyridine.

5-Bromo-2-cyano-3-methoxy-pyridine: Mix sodium methoxide (141 mg, 2.61 mmol) and 5-bromo-2-cyano-3-fluoropyridine (105 mg, 0.52 mmol) in THF (5 mL) and reflux for 18 h. Add pH 7 phosphate buffer solution and extract with EtOAc. Dry the EtOAc extracts over $MgSO_4$. Remove the drying agent and evaporate the filtrate. Purify the crude product using a silica gel chromatography and elute with EtOAc/hexane (0 to 30%) to give 77 mg (69% yield) of 5-bromo-2-cyano-3-methoxy-pyridine.

5-Bromo-2-cyano-3-chloro-pyridine: Add $NaNO_2$ (83.0 mg, 1.20 mmol) to a suspension of 3-amino-5-bromo-2-cyanopyridine (198 mg, 1.00 mmol) in 37% HCl (2.00 ml) and $H_2O$ (0.5 ml) at 0° C. and stir for 1 hour. Add copper powder (15 mg) and reflux the mixture for 30 minutes. Cool the mixture and, quench with ice, basify with 5N NaOH. Extract with EtOAc and wash the organic extract with brine, dry over $MgSO_4$. Purify crude product using silical gel chromatography and elute with (0-30% EtOAc/Hex) to produce 110 mg (50% yield) of 5-bromo-2-cyano-3-chloro-pyridine.

4-Bromo-naphthalene-1-carbonitrile: Sonicate a suspension of 4-bromo-naphthalen-1-ylamine (0.974 g, 4.386 mmol) in water (6 mL) and concentrated HCl (2 mL) for 10 minutes. Cool the resulting suspension to 0° C. Slowly add sodium nitrite (0.336 g, 4.869 mmol) in water (2 mL) at a rate to maintain the temperature below 5° C. Stir the resulting mixture for 30 minutes, and then neutralized with solid sodium bicarbonate. Add the resulting solution portion-wise to a solution of potassium cyanide (0.717 g, 11.010 mmol) and copper cyanide (0.464 g, 5.181 mmol) in water (10 mL). A precipitate forms. Heat the reaction mixture to 70° C. for 30 minutes, then extract the aqueous reaction mixture with ethyl acetate (3×20 mL). Combine the organics layers and wash sequentially with water (30 mL), saturated ammonium chloride (30 mL), and sodium bicarbonate (30 mL). Dry the resulting organic layers with ($Na_2SO_4$); remove the solids by filtration; and concentrate the filtrate in vacuo. Purify the resulting residue by flash chromatography with a gradient of hexanes to 20% ethyl acetate in hexanes to afford 0.864 g (85%) of 4-bromo-naphthalene-1-carbonitrile as a light brown solid. $^1$H NMR ($CDCl_3$) δ 8.314 (dd, 1H, J=2.4, 7.0 Hz), 8.235 (dd, 1H, J=2.4, 7.0 Hz), 7.836 (d, 1H, J=7.6 Hz), 7.728 (m, 3H).

4-Bromo-2-fluoro-benzamide: Charge a flask with acidic alumina ($Al_2O_3$) (3.03 g, 29.718 mmol) and methanesulfonic acid (10 mL). Heat the resulting solution to 120° C., and add 4-bromo-2-fluorobenzonitrile (2.00 g, 9.999 mmol) in one portion. Stir the resulting mixture for 30 minutes, then cool the reaction to room temperature and pour it into water (50 mL). Extract the aqueous mixture with dichloromethane (3×30 mL). Combine the organic extracts; dry over ($Na_2SO_4$); remove the solids by filtration; and concentrate the filtrate in vacuo, affording 2.14 g (98%) 4-bromo-2-fluorobenzamide as a white solid. $^1$H NMR (DMSO-ds) δ 7.706 (d, 2H, J=21.1 Hz), 7.598 (dd, 1H, J=1.9, 10.1 Hz), 7.557 (dd, 1H, J=8.0, 8.0 Hz), 7.446 (ddd, 1H, J=0.4, 1.9, 8.1 Hz).

5-(4-Bromo-2-fluoro-phenyl)-1H-tetrazole: Charge a flask with 4-bromo-2-fluoro benzonitrile (3.0 g, 15.0 mmol) and azidotributyltin (10 g, 30.0 mmol). Heat the mixture to 80° C. for 24 hours, then cool the reaction mixture and dilute it with 15 mL of diethyl ether. Pour the resulting solution into 15 mL of diethyl ether saturated with gaseous hydrochloric acid. Remove the resulting solid by filtration and wash the solids with hexanes to afford 3.1 g (85%) of the title material. LRMS (API ES+)=243.0 (M+H).

5-(4-Bromo-2-fluoro-phenyl)-1-methyl-1H-tetrazole: Add dry DMF to sodium hydride (0.2 g, 4.8 mmol), which was previously washed three times with hexanes, Cool the resulting suspension to 0° C. and add 5-(4-Bromo-2-fluoro-phenyl)-1H-tetrazole (1.0 g, 4.4 mmol) portion wise. Stir the mixture for 30 minutes then add methyl iodide (0.68 g, 4.8 mmol), and continue to stir the reaction at room temperature; monitor the reaction via TLC. When complete, quench the reaction with 10% $NaHSO_4$ (50 mL); dilute with ethyl acetate (50 mL); and separate the layers. Extract the aqueous layer three times with ethyl acetate (25 mL). Combine the organic layers; and dry over $MgSO_4$. Remove the solids by filtration and concentrate the filtrate in vacuo. Chromatograph the residue on a silica gel column eluting with 20% ethyl acetate in hexanes to afford 0.68 g (65%) of the title material. LRMS (API ES+)=239.0 (M+H).

5-Bromo-4-methyl-2-thiophene carboxamide: Combine methyl 5-bromo-4-methyl-2-thiophene carboxylate (5.0 g, 1.0 equiv, 21.2 mmol) and 7N $NH_3$ in MeOH (50 mL) in a flask. Heat the mixture in a sealed tube to 100° C. for 18 hours. Purify the residue on silica gel using 30% EtOAc/hex elution stepping to 80% EtOAc/hex elution. Isolated 0.7 g (64%). LRMS (API ES+)=221.8 (M+H).

5-Bromo-4-methyl-2-thiophene carbonitrile: Combine 5-bromo-4-methyl-2-thiophene carboxamide (1.2 g, 1.0 equiv., 5.4 mmol) and $POCl_3$ (30 mL) in a flask. Stir the mixture at room temperature for 18 hours. Purify the residue on silica gel using 30% EtOAc/hex elution to provide the title compound (0.7 g, 64%). $^1$H NMR ($CDCl_3$) δ 7.27 (s, 1H), 2.17 (s, 3H).

4-Bromo-3-methyl-2-thiophene carboxamide: Combine 4-bromo-3-methyl-2-thiophene carboxylic acid (2.0 g, 1.0 equiv, 9.0 mmol) and thionyl chloride (30 mL) in a flask. Stir the mixture at room temperature for 18 hours. Concentrate the resulting mixture in vacuo and then suspend the residue in 7N $NH_3$ in MeOH (50 mL). Stir for 1 hour. Concentrate in vacuo to afford 1.9 g (100%) of the title compound. LRMS (API ES+)=221.8 (M+H).

4-Bromo-3-methyl-2-thiophene carbonitrile: Dissolve 4-bromo-3-methyl-2-thiophene carboxamide in 30 mL of $POCl_3$ and allow the mixture to stir at room temperature for 18 hours. Then concentrate the reaction in vacuo; and purify the residue by chromatography (silica gel, 5% ethyl acetate/hexane) to give the title compound (0.9 g, 49%). $^1$H-NMR ($CDCl_3$) δ 9.44 (S, 1H), 4.40 (S, 3H).

4-Bromo-2-fluoro-6-methoxy-benzonitrile: Method DF1 Dissolve 4-bromo-2,5-difluoro-benzonitrile (1.5 g, 6.9 mmol) in THF (10 mL). Add NaOMe (1.9 g, 25% by wt solution in MeOH, (8.3 mmol). Stir the reaction mixture overnight at room temperature. Concentrate in vacuo and purify by silica gel chromatography (0-50% EtOAc/hexanes/30 min gradient). Concentrate the selected fractions in vacuo to afford the title compound (1.5 g, 94%) as a white solid. $^1$H-NMR is consistent with structure. TLC (20% EtOAc/hexanes) Rf=0.28.

4-Bromo-2-fluoro-6-methoxy-benzaldehyde: Method DF2 Dissolve 4-bromo-2-fluoro-6-methoxy-benzonitrile (1.15 g, 5.0 mmol) in dichloromethane (50 mL) and cool to 0° C. Add DIBAL (6.0 mL, 1.0 N in methylene chloride 1.2 mmol). Stir the reaction mixture for about 1 hour at 0° C. Add 5N HCl (20 mL) and stir the resulting solution for about 10 min. Extract with dichloromethane, wash with brine, dry over $Na_2SO_4$, filter and concentrate in vacuo. Purify by silica gel chromatography (0-50% EtOAc/hexanes/30 min gradient). Concentrate the selected fractions in vacuo with no heat to afford the title compound (485 mg, 44%) as a white solid. $^1$H-NMR is consistent with structure.

5-Bromo-2-difluoromethyl-1-fluoro-3-methoxy-benzene: (Method DF3) Dissolve 4-bromo-2-fluoro-6-methoxy-benzaldehyde (485 mg, 2.0 mmol) in dichloromethane (5 mL); add DAST (0.3 mL, 2.2 mmol) and reflux overnight in sealed tube. Cool to room temperature and transfer directly to silica gel chromatography loading cartridge. Purify by silica gel chromatography (0-50% EtOAc/hexanes/30 min gradient) and concentrate in vacuo to give the title compound (353 mg, 70% yield) as a colorless oil. TLC (20% EtOAc/hexanes) Rf=0.50. $^1$H-NMR is consistent with structure.

2-Bromo-5-ethynyl-trimethyl-silane-pyridine: Reflux a mixture of 2-bromo-5-iodo-pyridine (1 g, 3.5 mmol), ethynyl-trimethyl-silane (360 mg, 3.67 mmol), copper (I) iodide (20 mg, 0.1 mmol) and tetrakis (triphenylphosphine) palladium (0) (121 mg, 0.01 mmol) in triethyl amine (10 mL) under N2 in a sealed tube for 3 days. Evaporate the solvent. Purification of the crude residue using silica gel chromatography gave 800 mg (90%) of the desired product.

4-bromo-2-thiophenecarbonitrile: Reflux 4-bromo-2-thiophenecarboxylic acid (960 mg, 4.63 mmol) in $SOCl_2$ (5 mL) for 1 h. Evaporate excess $SOCl_2$. Add THF (5 mL) to the residue. Slowly drop the resulting solution to conc $NH_4OH$ (15 mL) in ice bath. Stir the mixture overnight. Concentrate the mixture, followed by addition of EtOAc, wash with brine; and dry over $MgSO_4$; filter and concentrate in vacuo. Add NaCl (307 mg, 5.26 mmol) and dichloromethane (10 mL) to the residue and reflux for 30 min. After the addition of $POCl_3$ (3.36 g, 21.9 mmol), reflux the mixture for 1 h. Dilute the mixture with dichloromethane and wash with aqueous $NaHCO_3$ solution, brine and dry over $MgSO_4$; filter and concentrate in vacuo to provide 753 mg of the desired product.

4-Bromo-2,6-dimethyl-benzonitrile: Place 4-Bromo-2,6-dimethyl-phenylamine (4.49 g, 22.4 mmol), water (25 mL) and concentrated hydrochloric acid (8.0 mL) in a three-neck flask and sonicate until a fine suspension results. Cool the suspension to 0° C. and add a solution of sodium nitrite (1.67 g, 24.2 mmol) in water (5 mL) dropwise to maintain a reaction temperature below 5° C. Stir the reaction at 0° C. for 30 minutes after the addition is complete. Carefully neutralize the reaction with solid sodium bicarbonate. Add the neutralized reaction portionwise to a round bottom flask containing copper (I) cyanide (2.42 g, 27.0 mmol), potassium cyanide (3.65 g, 56.1 mmol) and water (25 mL) at 70° C. Stir the resulting solution for 30 minutes at 70° C. Cool reaction to ambient temperature and extract with toluene (75 mL×3). Combine the organic layers and wash with water and brine. Dry over sodium sulfate and concentrate in vacuo. Purify by flash chromatography (2 to 20% ethylacetate in hexane) to give 4-Bromo-2,6-dimethyl-benzonitrile (3.36 g, 15.99 mmol, 71%). $^1$H NMR ($CDCl_3$) δ7.50 (s, H), 2.46 (s, 6H).

4-Bromo-2-chloro-6-methyl-benzonitrile: Prepare in substantially the same manner as 4-Bromo-2,6-dimethyl-benzonitrile from 4-bromo-2-chloro-6-methyl-phenyl amine. $^1$H NMR (DMSO-d6) δ 7.52 (s, 1H), 7.38 (s, 1H) 2.53 (s, 3H).

4-Bromo-2,6-dichloro-benzonitrile: Prepare in substantially the same manner as 4-Bromo-2,6-dimethyl-benzonitrile from the phenyl amine. $^1$H NMR ($CDCl_3$) δ 7.59 (s, 2H).

4-Bromo-3-methoxy-benzonitrile: Prepare in substantially the same manner as 4-Bromo-2,6-dimethyl-benzonitrile from the phenyl amine. $^1$H NMR ($CDCl_3$) δ 7.62 (d, 1H, J=7.9 Hz), 7.09 (dd, 1H, J=7.9 Hz, 1.8 Hz), 7.07 (d, 1H, J=1.8 Hz), 3.91 (s, 3H).

4-Bromo-2-fluoro-5-methyl-benzonitrile: Prepare in substantially the same manner as 4-Bromo-2,6-dimethyl-benzonitrile. $^1$H NMR ($CDCl_3$) δ 7.46 (m, 2H), 2.40 (s, 3H).

Compounds listed below in Table 1 can be prepared from compounds having the general structure of an indole core structure illustrated as intermediate 2 according the procedures listed above.

TABLE 1

Compounds Prepared From Intermediate 2

| Ex. | R1 | R3 | R6 | Name | Prep ‡ | Anal. † |
|---|---|---|---|---|---|---|
| 26 | Me | 3-cyanophenyl | Me | N-[3-(3-Cyano-phenyl)-1-methyl-1H-indol-6-yl]-methanesulfonamide | A, C, E, I | 343.0 (M + NH4) |
| 27 | cyclopentyl | 4-cyano-3-fluoro-phenyl | Me | N-[3-(4-Cyano-3-fluoro-phenyl)-1-cyclopentyl-1H-indol-6-yl]-methanesulfonamide | B, D, G, I | 415.1 (M + NH4) |
| 31 | (S)-sec-butyl | 4-cyano-3-fluoro-phenyl | Me | N-[1-((S)-sec-Butyl)-3-(4-cyano-3-fluoro-phenyl)-1H-indol-6-yl]-methanesulfonamide | BB, D, G, I | 403.3 (M + NH4) |
| 46 | (R)-sec-butyl | 4-cyano-phenyl | cyclopropyl | N-[1-((R)-sec-Butyl)-3-(4-cyano-phenyl)-1H-indol-6-yl]-cyclopropanesulfonamide | BB, C, G, I | 394.3 (M + H), 392.0 (M − H) |
| 47 | (R)-sec-butyl | 4-cyano-phenyl | Me | N-[1-((R)-sec-Butyl)-3-(4-cyano-phenyl)-1H-indol-6-yl]-methanesulfonamide | BB, C, G, I | 368.0 (M + H) |
| 49 | sec-butyl | 5-cyano-thiophen-2-yl | Me | N-[1-sec-Butyl-3-(5-cyano-thiophen-2-yl)-1H-indol-6-yl]-methanesulfonamide | BB, AA, F, I | 374.0 (M + 1) |
| 51 | sec-butyl | 5-cyano-thiophen-2-yl | Me | N-[1-sec-Butyl-3-(5-cyano-thiophen-2-yl)-1H-indol-6-yl]-methanesulfonamide | BB, AA, F, I | 374.0 (M + 1) |
| 52 | sec-butyl | 5-(hydroxyimino-methyl)-thiophen-2-yl | Me | N-{1-sec-Butyl-3-[5-(hydroxyimino-methyl)-thiophen-2-yl]-1H-indol-6-yl}-methanesulfonamide | BB, AA, F, I, Z-1*, Z-2 | 392.0 (M + H) |

TABLE 1-continued

Compounds Prepared From Intermediate 2

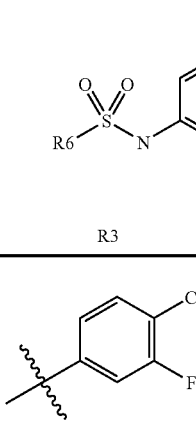

| Ex. | R1 | R3 | R6 | Name | Prep ‡ | Anal. † |
|---|---|---|---|---|---|---|
| 53 | 1-butyl | 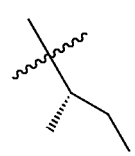 | Me | N-[1-Butyl-3-(4-cyano-3-fluoro-phenyl)-1H-indol-6-yl]-methanesulfonamide | A, AA, F, I | 384.0 (M − 1) |
| 57 | 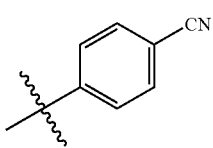 | 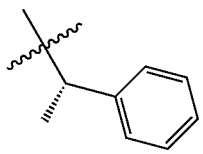 | Me | N-[1-sec-Butyl-3-(4-cyano-phenyl)-1H-indol-6-yl]-methanesulfonamide | BB, C, F, I | 385.0 (M + NH4) |
| 58 | 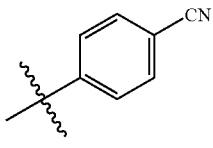 | 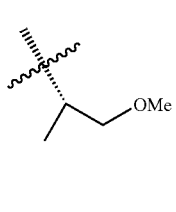 | Me | N-[3-(4-Cyano-phenyl)-1-((S)-1-phenyl-ethyl)-1H-indol-6-yl]-methanesulfonamide | BB, C, G, I | 414.13 (M − H) |
| 62 | 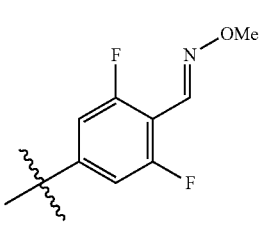 |  | Me | 2,6-Difluoro-1-(N-methoxyiminyl)-4-(1-(S-3-methoxypropan-2-yl)-6-methanesulfonylamino-1H-indol-3-yl)-benzene | LL, DD, AA, G, I, Z-1*, Z-2 | 450.0 (M − H) |
| 294 | 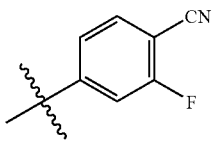 | 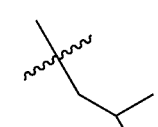 | Me | N-[3-(4-Cyano-3-fluoro-phenyl)-1-cyclopropylmethyl-1H-indol-6-yl]-methanesulfonamide | A, D, G, I | 382.1 (M − H) |
| 295 | 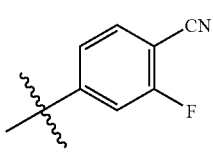 | 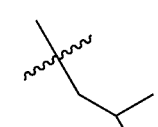 | Me | N-[3-(4-Cyano-3-fluoro-phenyl)-1-isobutyl-1H-indol-6-yl]-methanesulfonamide | A, C, F, I, | 384.0 (M − H) |

† Unless noted to the contrary the analytical data refers to the mess spectral data.
‡ Prep. Method of preparation referring to Schemes 1-6 and the accompanying experimental descriptions.

Compounds listed below in Table 2 can be prepared from compounds having the general structure of an indole core structure illustrated as Intermediate 3 according to the procedures listed above.

TABLE 2

Compounds Prepared from Intermediate 3

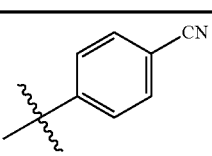

| Ex. | R1 | R3 | R6 | Name | Prep.‡ | Anal.† |
|---|---|---|---|---|---|---|
| 25 | Me | 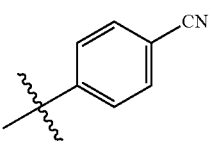 4-CN-phenyl | Me | N-[3-(4-Cyano-phenyl)-1-methyl-1H-indol-6-yl]-methanesulfonamide | C, E, I | 343.0 (M + NH₄) |
| 29 | i-Bu | 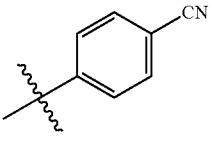 4-CN-phenyl | Me | N-[3-(4-Cyano-phenyl)-1-isobutyl-1H-indol-6-yl]-methanesulfonamide | C, E, I | 385.3 (M + NH₄) |
| 32 | Me | 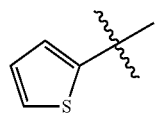 4-CN-phenyl | 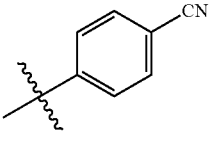 2-thienyl | Thiophene-2-sulfonic acid [3-(4-cyano-phenyl)-1-methyl-1H-indol-6-yl]-amide | C, E, I | 411.0 (M + NH4) |
| 33 | Me | 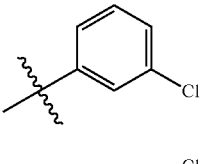 4-CN-phenyl | Et | Ethanesulfonic acid [3-(4-cyano-phenyl)-1-methyl-1H-indol-6-yl]-amide | C, E, I | 357.0 (M + NH4) |
| 34 | i-Pr | 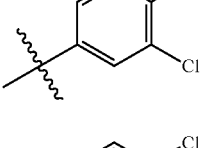 3-Cl-phenyl | Me | N-[3-(3-Chloro-phenyl)-1-isopropyl-1H-indol-6-yl]-methanesulfonamide | C, H, I | 361.0 (M − 1) |
| 35 | i-Pr | 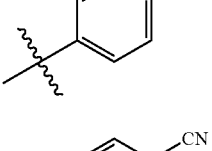 3,4-diCl-phenyl | Me | N-[3-(3,4-Dihloro-phenyl)-1-isopropyl-1H-indol-6-yl]-methanesulfonamide | C, H, I | 395.0 (M − 1) |
| 36 | i-Pr | 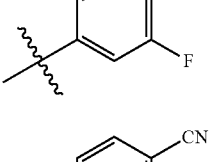 4-Cl-phenyl | Me | N-[3-(4-Chloro-phenyl)-1-isopropyl-1H-indol-6-yl]-methanesulfonamide | C, H, I | 361.0 (M − 1) |
| 38 | i-Pr | 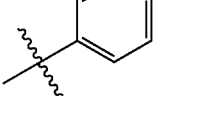 4-CN-3-F-phenyl | Me | N-[3-(4-Cyano-3-fluoro-phenyl)-1-isopropyl-1H-indol-6-yl]-methanesulfonamide | C, E, I | 389.0 (M + NH4) |
| 39 | Me | 4-CN-phenyl | cyclopropyl | Cyclopropanesulfonic acid [3-(4-cyano-phenyl)-1-methyl-1H-indol-6-yl]-amide | C, E, I | 369.0 (M + NH4) |

TABLE 2-continued

Compounds Prepared from Intermediate 3

| Ex. | R1 | R3 | R6 | Name | Prep.‡ | Anal.† |
|---|---|---|---|---|---|---|
| 40 | i-Pr | 4-cyano-3-fluoro-phenyl | thiophen-2-yl | Thiophene-2-sulfonic acid [3-(4-cyano-3-fluoro-phenyl)-1-isopropyl-1H-indol-6-yl]-amide | C, E, I | 457.0 (M + NH4) |
| 41 | i-Pr | 4-cyano-3-fluoro-phenyl | cyclopropyl | Cyclopropanesulfonic acid [3-(4-cyano-3-fluoro-phenyl)-1-isopropyl-1H-indol-6-yl]-amide | D, E, I | 415.0 (M + NH4) |
| 43 | i-Pr | 5-cyano-thiophen-2-yl | Me | N-[3-(5-Cyano-thiophen-2-yl)-1-isopropyl-1H-indol-6-yl]-methanesulfonamide | C, G, I | 360.0 (M + H) |
| 56 | isobutyl | 5-cyano-thiophen-2-yl | Me | N-[3-(5-Cyano-thiophen-2-yl)-1-isopropyl-1H-indol-6-yl]-methanesulfonamide | C, G, I | 374.0 (M + H) |
| 60 | isobutyl | 4-cyano-3-fluoro-phenyl | Me | N-[3-(4-Cyano-3-fluoro-phenyl)-1-isobutyl-1H-indol-6-yl]-methanesulfonamide | C, F, I | 403.0 (M + NH4) |
| 70 | 1-ethyl-propyl | 6-cyano-pyridin-3-yl | Me | N-[3-(6-cyano-pyridin-3-yl)-1-(1-ethyl-propyl)-1H-indol-6-yl]-methanesulfonamide hydrochloride | C, F, I | 383.0 |
| 101 | (S)-sec-butyl | 6-cyano-pyridin-3-yl | Me | (S)—N-[1-sec-butyl-3-(6-cyano-pyridin-3-yl)-1H-indol-6-yl]-methanesulfonamide hydrochloride | C, F, I | 369.0 |
| 102 | (R)-sec-butyl | 6-cyano-pyridin-3-yl | Me | (R)—N-[1-sec-butyl-3-(6-cyano-pyridin-3-yl)-1H-indol-6-yl]-methanesulfonamide hydrochloride | C, F, I | 369.0 |

TABLE 2-continued

Compounds Prepared from Intermediate 3

| Ex. | R1 | R3 | R6 | Name | Prep.‡ | Anal.† |
|---|---|---|---|---|---|---|
| 103 | cyclopentyl | 5-tert-butyl-6-cyanopyridin-3-yl | Me | N-[3-(6-cyano-pyridin-3-yl)-1-cyclopentyl-1H-indol-6-yl]-methanesulfonamide | C, F, I | 381.3 |
| 104 | Me | phenyl | Me | N-(1-Methyl-3-phenyl-1H-indol-6-yl)-methanesulfonamide | C, E, I | 301.0 (M + H) |
| 105 | Me | 4-methoxyphenyl | Me | N-[3-(4-Methoxy-phenyl)-1-methyl-1H-indol-6-yl]-methanesulfonamide | C, E, I | 331.0 (M + H) |
| 106 | i-Pr | 4-cyanophenyl | thiophen-2-yl | Thiophene-2-sulfonic acid [3-(4-cyano-phenyl)-1-isopropyl-1H-indol-6-yl]-amide | C, E, I | 422.0 (M + H) |
| 78 | i-Pr | 5-cyano-1-methyl-1H-pyrrol-2-yl | Me | N-[3-(5-Cyano-1-methyl-1H-pyrrol-2-yl)-1-isopropyl-1H-indol-6-yl]-methanesulfonamide | D, F, I | 357.0 (M + H) |
| 108 | i-Pr | m-tolyl | Me | N-(1-Isopropyl-3-m-tolyl-1H-indol-6-yl)-methanesulfonamide | R, H, I | 341.13 (M − H) |
| 109 | i-Pr | benzo[1,3]dioxol-5-yl | Me | N-(3-Benzo[1,3]dioxol-5-yl-1-isopropyl-1H-indol-6-yl)-methanesulfonamide | R, H, I | 373.0 (M + H) |
| 110 | i-Pr | 2-methoxyphenyl | Me | N-[1-Isopropyl-3-(2-methoxy-phenyl)-1H-indol-6-yl]-methanesulfonamide | R, H, I | 359.14 (M + H) |
| 111 | i-Pr | 3-acetylphenyl | Me | N-[3-(3-Acetyl-phenyl)-1-isopropyl-1H-indol-6-yl]-methanesulfonamide | R, H, I | 371.47 (M + H) |

TABLE 2-continued

Compounds Prepared from Intermediate 3

| Ex. | R1 | R3 | R6 | Name | Prep.‡ | Anal.† |
|---|---|---|---|---|---|---|
| 112 | i-Pr | 4-fluoro-2-methyl-phenyl | Me | N-[3-(4-Fluoro-2-methyl-phenyl)-1-isopropyl-1H-indol-6-yl]-methanesulfonamide | R, H, I | 361.14 (M + H) |
| 113 | i-Pr | 4-acetyl-phenyl | Me | N-[3-(4-Acetyl-phenyl)-1-isopropyl-1H-indol-6-yl]-methanesulfonamide | R, H, I | 371.14 (M + H) |
| 114 | i-Pr | naphthalen-2-yl | Me | N-(1-Isopropyl-3-naphthalen-2-yl-1H-indol-6-yl)-methanesulfonamide | R, H, I | 379.15 (M + H) |
| 115 | i-Pr | 4-(cyclopropylcarbamoyl)phenyl | Me | N-Cyclopropyl-4-(1-isopropyl-6-methanesulfonylamino-1H-indol-3-yl)-benzamide | R, H, I | 412.17 (M + H) |
| 116 | isobutyl | 3-chloro-4-cyano-phenyl | Me | N-[3-(3-Chloro-4-cyano-phenyl)-1-isobutyl-1H-indol-6-yl]-methanesulfonamide | D, G, I | 419.0 (M + NH4) |
| 93 | i-Pr | 4-hydroxy-phenyl | Me | N-[3-(4-Hydroxy-phenyl)-1-isopropyl-1H-indol-6-yl]-methanesulfonamide | R, H, I | 345.13 (M + H) |
| 117 | i-Pr | 3-cyano-phenyl | Me | N-[3-(3-Cyano-phenyl)-1-isopropyl-1H-indol-6-yl]-methanesulfonamide | C, F, I | 354.0 (M + H) |
| 118 | i-Pr | 3-chloro-5-cyano-thiophen-2-yl | Me | N-[3-(4-Chloro-5-cyano-thiophen-2-yl)-1-isopropyl-1H-indol-6-yl]-methanesulfonamide | C, G, I | 411.0 (M + NH4) |

TABLE 2-continued

Compounds Prepared from Intermediate 3

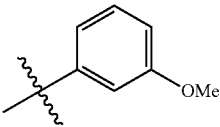

| Ex. | R1 | R3 | R6 | Name | Prep.‡ | Anal.† |
|---|---|---|---|---|---|---|
| 119 | i-Pr | 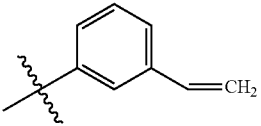 | Me | N-[1-Isopropyl-3-(3-methoxy-phenyl)-1H-indol-6-yl]-methanesulfonamide | R, H, I | 359.14 (M + H) |
| 120 | i-Pr | 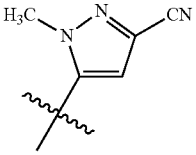 | Me | N-[1-Isopropyl-3-(3-vinyl-phenyl)-1H-indol-6-yl]-methanesulfonamide | R, H, I | 355.15 (M + H) |
| 121 | i-Pr | 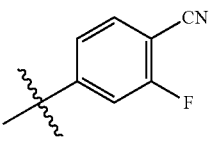 | Me | N-[3-(5-Cyano-2-methyl-2H-pyrazol-3-yl)-1-isopropyl-1H-indol-6-yl]-methanesulfonamide | *** | 358.0 (M + H) |
| 122 | i-Pr | 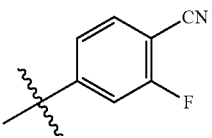 | i-Pr | Propane-2-sulfonic acid [3-(4-cyano-3-fluoro-phenyl)-1-isopropyl-1H-indol-6-yl]-amide | D, G, I | 417.0 (M + NH4) |
| 123 | i-Pr | 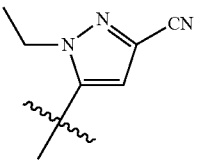 | Et | Ethanesulfonic acid [3-(4-cyano-3-fluoro-phenyl)-1-isopropyl-1H-indol-6-yl]-amide | D, G, I | 403.3 (M + NH4) |
| 124 | i-Pr | 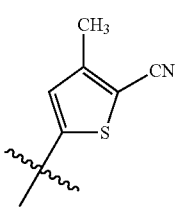 | Me | N-[3-(5-Cyano-2-ethyl-2H-pyrazol-3-yl)-1-isopropyl-1H-indol-6-yl]-methanesulfonamide | *** | 372.15 (M + H) |
| 125 | i-Pr | 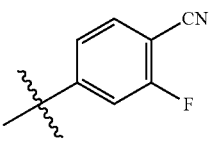 | Me | N-[3-(5-Cyano-4-methyl-thiophen-2-yl)-1-isopropyl-1H-indol-6-yl]-methanesulfonamide | AA, G, I | 374.09 (M + H) |
| 126 | i-Pr | 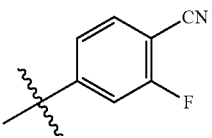 | Me | N-[3-(4-Chloro-3-fluoro-phenyl)-1-isopropyl-1H-indol-6-yl]-methanesulfonamide | AA, G, I | 379.07 (M − H) |

TABLE 2-continued

Compounds Prepared from Intermediate 3

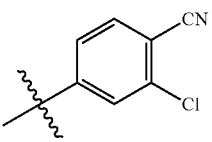

| Ex. | R1 | R3 | R6 | Name | Prep.‡ | Anal.† |
|---|---|---|---|---|---|---|
| 127 | n-Pr | 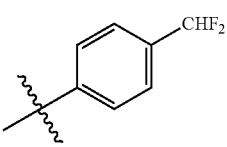 4-CN, 3-Cl phenyl | Me | N-[3-(3-Chloro-4-cyano-phenyl)-1-propyl-1H-indol-6-yl]-methanesulfonamide | C, G, I | 386.1 (M − H) |
| 128 | i-Pr | 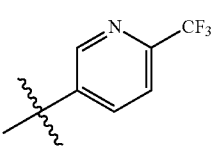 4-CHF₂ phenyl | Me | N-[3-(4-Difluoromethyl-phenyl)-1-isopropyl-1H-indol-6-yl]-methanesulfonamide | D, F, I | 377.1 (M − H) |
| 129 | i-Pr | 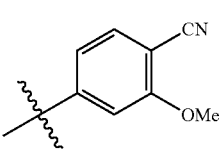 6-CF₃ pyridin-3-yl | Me | N-[1-Isopropyl-3-(5-trifluoromethyl-pyridin-3-yl)-1H-indol-6-yl]-methanesulfonamide hydrochloride | C, F, I | 396.0 (M − H) |
| 130 | (R)-sec-Bu | 4-CN, 3-OMe phenyl | Me | (R)—N-[1-sec-Butyl-3-(4-cyano-3-methoxy-phenyl)-1H-indol-6-yl]-methanesulfonamide | D, G, I | 396.2 (M − H) |
| 131 | (S)-sec-Bu | 4-CN, 3-OMe phenyl | Me | (S)—N-[1-sec-Butyl-(4-cyano-3-methoxy-phenyl-1H-indol-6-yl]-methanesulfonamide | D, G, I | 396.2 (M − H) |
| 132 | (R)-sec-Bu | 4-CN, 3-Cl phenyl | Me | (R)—N-[1-sec-Butyl-3-(3-chloro-4-cyano-phenyl)-1H-indol-6-yl]-methanesulfonamide | D, G, I | 400.2 (M − H) |
| 133 | (S)-sec-Bu | 4-CN, 3-Cl phenyl | Me | (S)—N-[1-sec-Butyl-3-(3-chloro-4-cyano-phenyl)-1H-indol-6-yl]-methanesulfonamide | D, G, I | 400.0 (M − H) |
| 134 | i-Pr | 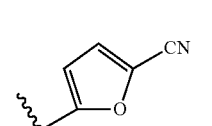 5-cyano-furan-2-yl | Me | N-[3-(5-Cyano-furan-2-yl)-1-isopropyl-1H-indol-6-yl]-methanesulfonamide | C, F, I | 342.2 (M − H) |

TABLE 2-continued

Compounds Prepared from Intermediate 3

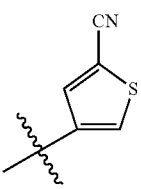

| Ex. | R1 | R3 | R6 | Name | Prep.‡ | Anal.† |
|---|---|---|---|---|---|---|
| 135 | i-Pr | 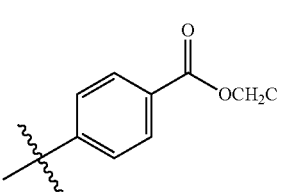 | Me | N-[3-(5-Cyano-thiophen-3-yl)-1-isopropyl-1H-indol-6-yl]-methanesulfonamide | C, F, I | 358.3 (M − H) |
| 74 | i-Pr | 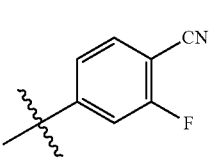 | Me | 4-(1-Isopropyl-6-methanesulfonylamino-1H-indol-3-yl)-benzoic acid ethyl ester | C, F, I | 399.3 (M − H) |
| 298 | n-Bu | 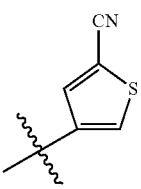 | Me | N-[3-(4-Cyano-3-fluoro-phenyl)-1-propyl-1H-indol-6-yl]-methanesulfonamide | D, G, I | 389.3 (M + NH4) |
| 297 | i-Pr | 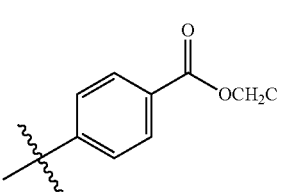 | cyclopropyl | Cyclopropylsulfonic acid-N-[3-(5-Cyano-thiophen-2-yl)-1-isopropyl-1H-indol-6-yl]-amide | AA, F, I | 356.3 (M + H) |
| 299 | 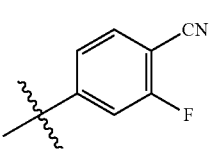 | 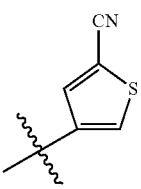 | Me | N-[1-((R)-sec-Butyl)-3-(4-cyano-3-fluoro-phenyl)-1H-indol-6-yl]-methanesulfonamide | D, G, I | 403.0 (M + NH4) |
| 300 | i-Pr | 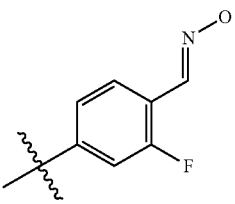 | Me | N-{3-[3-fluoro-4-(hydroxyimino-methyl)-phenyl]-1-isopropyl-1H-indol-6-yl}-methanesulfonamide | AA, G, I, Z-1*, Z-2* | |

***See Experimental Section
†Unless noted to the contrary the analytical data refers to the mass spectral data.
‡Prep. Method of preparation referring to Schemes 1-6 and the accompanying experimental descriptions.
*See Methods Z-1 and Z-2 below.

TABLE 3

Compounds Prepared From Intermediate 4

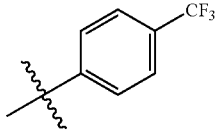

| Ex. | R1 | R3 | R6 | Name | Prep ‡ | Anal. † |
|---|---|---|---|---|---|---|
| 37 | i-Pr | 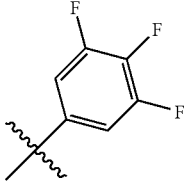 | Me | N-[3-(4-Trifluoromethyl-phenyl)-1-isopropyl-1H-indol-6-yl]-methanesulfonamide | D, H, I | 397.0 (M + H) |
| 42 | i-Pr | 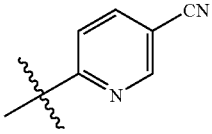 | Me | N-[3-(3,4,5-Trifluoro-phenyl)-1-isopropyl-1H-indol-6-yl]-methanesulfonamide | D, H, I | 383.0 (M + H) |
| 44 | i-Pr | 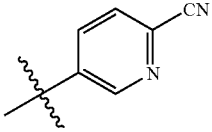 | Me | N-[3-(5-Cyano-pyridin-2-yl)-1-isopropyl-1H-indol-6-yl]-methanesulfonamide | D, E, I | 355.0 (M + H) |
| 48 | i-Pr | 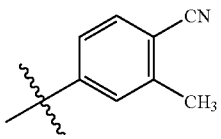 | Me | N-[3-(6-Cyano-pyridin-3-yl)-1-isopropyl-1H-indol-6-yl]-methanesulfonamide | D, H, I | 355.0 (M + H) |
| 49 | i-Pr | 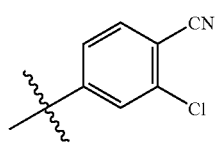 | Me | N-[3-(4-Cyano-3-methyl-phenyl)-1-isopropyl-1H-indol-6-yl]-methanesulfonamide | D, E, I | 368.0 (M + H) |
| 50 | i-Pr | 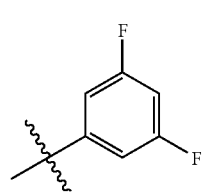 | Me | N-[3-(4-Cyano-3-chloro-phenyl)-1-isopropyl-1H-indol-6-yl]-methanesulfonamide | D, F, I | 405.0 (M + NH4) |
| 58 | i-Pr | 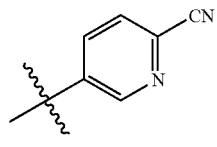 | Me | N-[3-(3,5-difluoro-phenyl)-1-isopropyl-1H-indol-6-yl]-methanesulfonamide | D, H, I | 365.0 (M + H) |
| 61 | i-Bu |  | Me | N-[3-(6-Cyano-pyridin-3-yl)-1-isobutyl-1H-indol-6-yl]-methanesulfonamide | D, H, I | 369.0 (M + H) |

TABLE 3-continued

Compounds Prepared From Intermediate 4

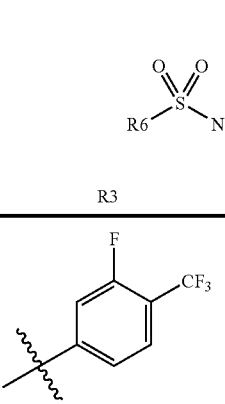

| Ex. | R1 | R3 | R6 | Name | Prep ‡ | Anal. † |
|---|---|---|---|---|---|---|
| 142 | i-Pr | 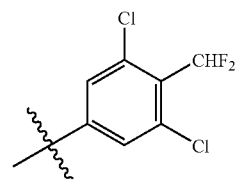 | Me | N-[3-(3-fluoro-4-trifluoromethyl-phenyl)-1-isopropyl-1H-indol-6-yl]-methanesulfonamide | D, G, I | 413.1 (M − H) |
| 143 | i-Pr | 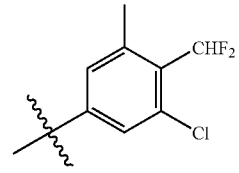 | Me | N-[3-(3,5-dichloro-4-difluoromethyl-phenyl)-1-isopropyl-1H-indol-6-yl]-methanesulfonamide | D, G, I | 445.0 (M − H) |
| 144 | i-Pr | 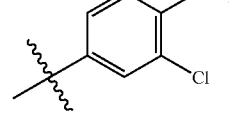 | Me | N-[3-(3-chloro-4-difluoromethyl-5-methyl-phenyl)-1-isopropyl-1H-indol-6-yl]-methanesulfonamide | D, G, I | 425.1 (M − H) |
| 145 | i-Pr | 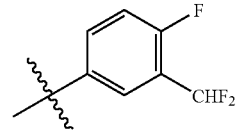 | Me | N-[3-(3-chloro-4-difluoromethyl-phenyl)-1-isopropyl-1H-indol-6-yl]-methanesulfonamide | D, G, I | 411.1 (M − H) |
| 146 | i-Pr | 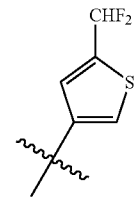 | Me | N-[3-(3-difluoromethyl-4-fluoro-phenyl)-1-isopropyl-1H-indol-6-yl]-methanesulfonamide | D, G, I | 397.0 (M + H) |
| 147 | i-Pr | 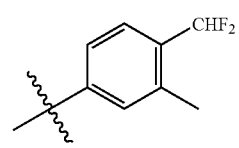 | Me | N-[3-(5-difluoromethyl-thiophen-3-yl)-1-isopropyl-1H-indol-6-yl]-methanesulfonamide | D, G, I | 385.0 (M + H) |
| 148 | i-Pr | 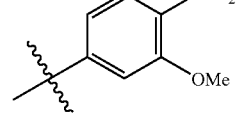 | Me | N-[3-(4-Difluoromethyl-3-methyl-phenyl)-1-isopropyl-1H-indol-6-yl]-methanesulfonamide | D, G, I | 391.1 (M + H) |
| 149 | i-Pr |  | Me | N-[3-(4-difluoromethyl-3-methyl-phenyl)-1-isopropyl-1H-indol-6-yl]-methanesulfonamide | D, G, I | 407.1 (M − H) |

TABLE 3-continued

Compounds Prepared From Intermediate 4

| Ex. | R1 | R3 | R6 | Name | Prep ‡ | Anal. † |
|---|---|---|---|---|---|---|
| 154 | i-Pr | 4-(CO₂CH₃)phenyl | Me | 4-(1-Isopropyl-6-methanesulfonylamino-1H-indol-3-yl)-benzoic acid methyl ester | C, F, I | 385.3 (M − H) |
| 87 | i-Pr | 4-(C(O)NH₂)phenyl | Me | 4-(1-Isopropyl-6-methanesulfonylamino-1H-indol-3-yl)-benzamide | C, F, I | 370.3 (M − H) |
| 155 | i-Pr | 3-fluoro-4-(1-methyl-1H-tetrazol-5-yl)phenyl | Me | N-{3-[3-Fluoro-4-(1-methyl-1H-tetrazol-5-yl)-phenyl]-1-isopropyl-1H-indol-6-yl}-methanesulfonamide | O, F, I | 429.0 (M + H), 427.0 (M − H) |
| 156 | i-Pr | 5-(1-methyl-1H-tetrazol-5-yl)thiophen-2-yl | Me | N-{1-Isopropyl-3-[5-(1-methyl-1H-tetrazol-5-yl)-thiophen-2-yl]-1H-indol-6-yl}-methanesulfonamide | O, F, I | 417.0 (M + H), 415.0 (M − H) |
| 157 | i-Pr | 5-cyano-4-methyl-thiophen-3-yl | Me | N-[3-(5-Cyano-4-methyl-thiophen-3-yl)-1-isopropyl-1H-indol-6-yl]-methanesulfonamide | O, F, I | 372.0 (M − H) |
| 158 | i-Pr | 5-cyano-3-methyl-thiophen-2-yl | Me | N-[3-(5-Cyano-3-methyl-thiophen-2-yl)-1-isopropyl-1H-indol-6-yl]-methanesulfonamide | O, F, I | 374.0 (M + H), 372.2 (M − H) |
| 159 | i-Pr | 3,5-dimethyl-isoxazol-4-yl | Me | N-[3-(3,5-Dimethyl-isoxazol-4-yl)-1-isopropyl-1H-indol-6-yl]-methanesulfonamide | O, F, I | 348 (M + H), 346.2 (M − H) |

TABLE 3-continued

Compounds Prepared From Intermediate 4

| Ex. | R1 | R3 | R6 | Name | Prep ‡ | Anal. † |
|---|---|---|---|---|---|---|
| 160 | i-Pr | 3-chloro-4-cyano-5-methyl-phenyl (CH₃, CN, Cl) | Me | N-[3-(3-Chloro-4-cyano-5-methyl-phenyl)-1-isopropyl-1H-indol-6-yl]-methanesulfonamide | O, H, I | 348 (M + H), 346.2 (M − H) |
| 161 | i-Pr | 4-cyano-3,5-dimethyl-phenyl (CH₃, CN, CH₃) | Me | N-[3-(4-Cyano-3,5-dimethyl-phenyl)-1-isopropyl-1H-indol-6-yl]-methanesulfonamide | D, F, I | 382.0 (M + H) |
| 161 | i-Pr | Benzo[b]thiophen-6-yl | Me | N-(3-Benzo[b]thiophen-6-yl-1-isopropyl-1H-indol-6-yl)-methanesulfonamide | D, G, I | 407.1 (M + Na) |
| 95 | i-Pr | Benzo[b]thiophen-5-yl | Me | N-(3-Benzo[b]thiophen-5-yl-1-isopropyl-1H-indol-6-yl)-methanesulfonamide | D, G, I | 407.1 M + Na |
| 162 | i-Pr | 3,5-dichloro-4-cyano-phenyl (Cl, CN, Cl) | Me | N-[3-(3,5-Dichloro-4-cyano-phenyl)-1-isopropyl-1H-indol-6-yl]-methanesulfonamide | O, H, I | 439.3 (M + NH4) |
| 107 | i-Pr | 1-methyl-1H-indazol-5-yl | Me | N-[1-Isopropyl-3-(1-methyl-1H-indazol-5-yl)-1H-indol-6-yl]-methanesulfonamide | D, G, I | 383.2 (M + H) |
| 167 | i-Pr | 4-cyano-5-fluoro-2-methyl-phenyl (F, CN, CH₃) | Me | N-[3-(4-Cyano-5-fluoro-2-methyl-phenyl)-1-isopropyl-1H-indol-6-yl]-methanesulfonamide | D, G, I | 384.1 (M − H) |

TABLE 3-continued

Compounds Prepared From Intermediate 4

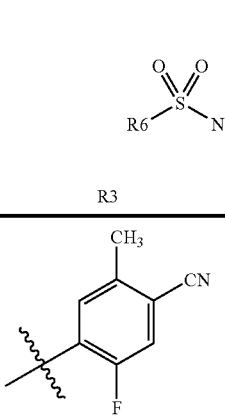

| Ex. | R1 | R3 | R6 | Name | Prep ‡ | Anal. † |
|---|---|---|---|---|---|---|
| 168 | i-Pr | 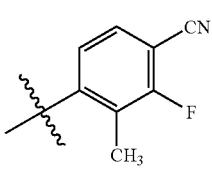 | Me | N-[3-(4-Cyano-2-fluoro-5-methyl-phenyl)-1-isopropyl-1H-indol-6-yl]-methanesulfonamide | D, G, I | 384.1 (M − H) |
| 169 | i-Pr | 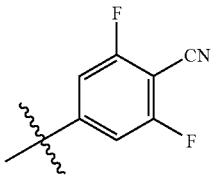 | Me | N-[3-(4-Cyano-3-fluoro-2-methyl-phenyl)-1-isopropyl-1H-indol-6-yl]-methanesulfonamide | D, G, I | 403.0 (M + NH4) |
| 170 | i-Pr | 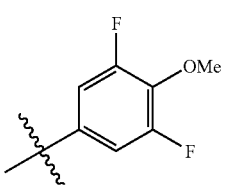 | Me | N-[3-(4-Cyano-3,5-difluoro-phenyl)-1-isopropyl-1H-indol-6-yl]-methanesulfonamide | D, G, I | 407.0 (M + NH4) |
| 179 | i-Pr | 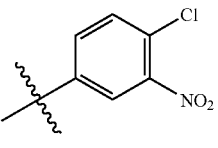 | Me | N-[3-(3,5-Difluoro-4-methoxy-phenyl)-1-isopropyl-1H-indol-6-yl]-methanesulfonamide | AA, G, I | 395.12 (M + H) |
| 180 | i-Pr | 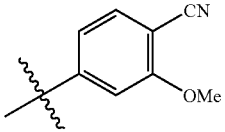 | Me | N-[3-(4-Chloro-3-nitro-phenyl)-1-isopropyl-1H-indol-6-yl]-methanesulfonamide | AA, G, I | 406.0634 (M − H) |
| 181 | i-Pr | 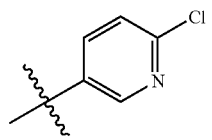 | Me | N-[3-(4-Cyano-3-methoxy-phenyl)-1-isopropyl-1H-indol-6-yl]-methanesulfonamide | D, G, I | 382.0 (M − H) |
| 182 | i-Pr | 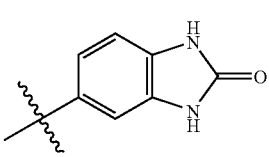 | Me | N-[3-(6-Chloro-pyridin-3-yl)-1-isopropyl-1H-indol-6-yl]-methanesulfonamide | O, G, I | 362.0 (M − H) |
| 183 | i-Pr |  | Me | N-[1-Isopropyl-3-(2-oxo-2,3-dihydro-1H-benzoimidazol-5-yl)-1H-indol-6-yl]-methanesulfonamide | O, F, I | 385.3 (M + H) |

TABLE 3-continued

Compounds Prepared From Intermediate 4

| Ex. | R1 | R3 | R6 | Name | Prep ‡ | Anal. † |
|---|---|---|---|---|---|---|
| 184 | i-Pr | (5-substituted-2-oxo-2,3-dihydro-1H-indol-5-yl) | Me | N-(1-Isopropyl-2'-oxo-2',3'-dihydro-1H,1'H-[3,5']biindolyl-6-yl)-methanesulfonamide | O, F, I | 384.3 (M + H) |

† Unless noted to the contrary the analytical data refers to the mass spectral data.
‡ Prep. Method of preparation referring to Schemes 1-6 and the accompanying experimental descriptions.

Compounds listed below in Table 3 can be prepared from compounds having the general structure of an indole core structure illustrated as Intermediate 4 according to the procedures listed above.

Compounds listed below in Table 4 can be prepared from compounds having the general structure of an indole core illustrated as Intermediate 4-A according to the procedures listed above.

TABLE 4

Compounds Prepared From Intermediate 4-A

| Ex. | R1 | R3 | R6 | Name | Prep. ‡ | Anal. † |
|---|---|---|---|---|---|---|
| 178 | i-Pr | (6-cyano-5-fluoropyridin-3-yl) | Me | N-[3-(6-Cyano-5-fluoro-pyridin-3-yl)-1-isopropyl-1H-indol-6-yl]-methanesulfonamide | X | 373.0 (M + H) |
| 186 | i-Pr | (2,2-difluorobenzo[1,3]dioxol-5-yl) | Me | N-[3-(2,2-Difluoro-benzo[1,3]dioxol-5-yl)-1-isopropyl-1H-indol-6-yl]-methanesulfonamide | X | 409.0 (M + H) |
| 187 | i-Pr | (5-difluoromethylpyridin-2-yl) | Me | N-[3-(5-Difluoromethyl-pyridin-2-yl)-1-isopropyl-1H-indol-6-yl]-methanesulfonamide | X | 380.0 (M + H) |
| 188 | i-Pr | (2,3-dihydrobenzo[1,4]dioxin-6-yl) | Me | N-[3-(2,3-Dihydro-benzo[1,4]dioxin-6-yl)-1-isopropyl-1H-indol-6-yl]-methanesulfonamide | X | 387.2 (M + H) |

TABLE 4-continued

Compounds Prepared From Intermediate 4-A

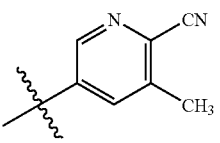

| Ex. | R1 | R3 | R6 | Name | Prep. ‡ | Anal. † |
|---|---|---|---|---|---|---|
| 189 | i-Pr | 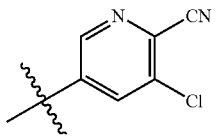 | Me | N-[3-(6-Cyano-5-methyl-pyridin-3-yl)-1-isopropyl-1H-indol-6-yl]-methanesulfonamide | C | 369.0 (M + H) |
| 190 | i-Pr | 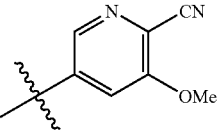 | Me | N-[3-(5-Chloro-6-cyano-pyridin-3-yl)-1-isopropyl-1H-indol-6-yl]-methanesulfonamide | C | 389.0 (M + H) |
| 191 | i-Pr | 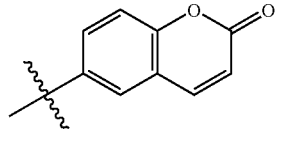 | Me | N-[3-(6-Cyano-5-methoxy-pyridin-3-yl)-1-isopropyl-1H-indol-6-yl]-methanesulfonamide | C | 385.1 (M + H) |
| 96 | i-Pr | 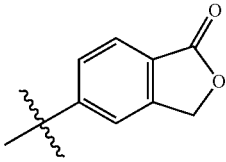 | Me | N-[1-Isopropyl-3-(2-oxo-2H-chromen-6-yl)-1H-indol-6-yl]-methanesulfonamide | O | 397.0 (M + H) |
| 97 | i-Pr | 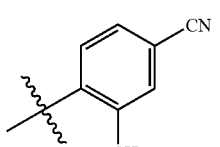 | Me | N-[1-Isopropyl-3-(1-oxo-1,3-dihydro-isobenzofuran-5-yl)-1H-indol-6-yl]-methanesulfonamide | Q ** | 385.0 (M + H) |
| 192 | i-Pr | 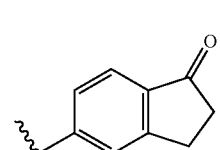 | Me | N-[3-(4-Cyano-2-methyl-phenyl)-1-isopropyl-1H-indol-6-yl]-methanesulfonamide | Q | 366.2 (M − H) |
| 193 | i-Pr | 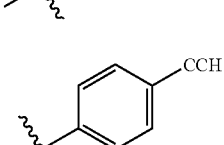 | Me | N-[1-Isopropyl-3-(1-oxo-indan-5-yl)-1H-indol-6-yl]-methanesulfonamide | AA | 383.0 (M + H) |
| 194 | i-Pr |  | Me | N-[3-(4-Ethynyl-phenyl)-1-isopropyl-1H-indol-6-yl]-methanesulfonamide | AA | 353.0 (M + H) |

TABLE 4-continued

Compounds Prepared From Intermediate 4-A

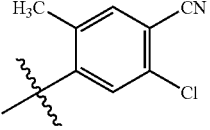

| Ex. | R1 | R3 | R6 | Name | Prep. ‡ | Anal. † |
|---|---|---|---|---|---|---|
| 195 | i-Pr | 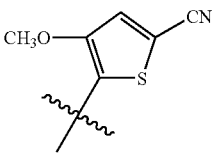 | Me | N-[3-(5-Chloro-4-cyano-2-methyl-phenyl)-1-isopropyl-1H-indol-6-yl]-methanesulfonamide | *** | 400.09 (M − H) |
| 196 | i-Pr | 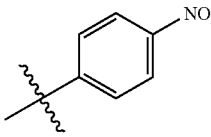 | Me | N-[3-(5-Cyano-3-methoxy-thiophen-2-yl)-1-isopropyl-1H-indol-6-yl]-methanesulfonamide | AA | 388.08 (M − H) |
| 197 | i-Pr | 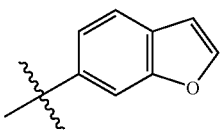 | Me | N-[1-Isopropyl-3-(4-nitro-phenyl)-1H-indol-6-yl]-methanesulfonamide | AA | 374.3 (M + H) |
| 198 | i-Pr | 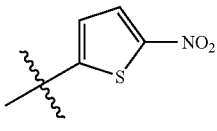 | Me | N-(3-Benzofuran-6-yl-1-isopropyl-1H-indol-6-yl)-methanesulfonamide | AA | 367.0 (M − H) |
| 199 | i-Pr | 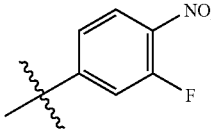 | Me | N-[1-Isopropyl-3-(5-nitro-thiophen-2-yl)-1H-indol-6-yl]-methanesulfonamide | AA | 378.0 (M − H) |
| 200 | i-Pr | 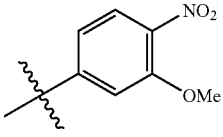 | Me | N-[3-(3-Fluoro-4-nitro-phenyl)-1-isopropyl-1H-indol-6-yl]-methanesulfonamide | AA | 390.0 (M − H) |
| 201 | i-Pr | 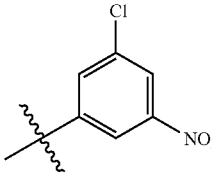 | Me | N-[1-Isopropyl-3-(3-methoxy-4-nitro-phenyl)-1H-indol-6-yl]-methanesulfonamide | AA | 402.0 (M − H) |
| 202 | i-Pr | 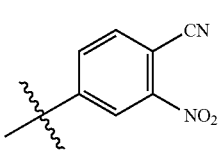 | Me | N-[3-(4-Chloro-2-nitro-phenyl)-1-isopropyl-1H-indol-6-yl]-methanesulfonamide | AA | 406.06 (M − H) |
| 203 | i-Pr |  | Me | N-[3-(4-Cyano-3-nitro-phenyl)-1-isopropyl-1H-indol-6-yl]-methanesulfonamide | AA | 397.0 (M − H) |

TABLE 4-continued

Compounds Prepared From Intermediate 4-A

| Ex. | R1 | R3 | R6 | Name | Prep. ‡ | Anal. † |
|---|---|---|---|---|---|---|
| 204 | i-Pr | (2-fluoro-4-yl benzamide with N-cyclopropyl) | Me | N-Cyclopropyl-2-fluoro-4-(1-isopropyl-6-methanesulfonylamino-1H-indol-3-yl)-benzamide | AA | 430.2 M + H |
| 205 | i-Pr | (3-chloro-4-cyano-2-methyl-phenyl) | Me | N-[3-(3-Chloro-4-cyano-2-methyl-phenyl)-1-isopropyl-1H-indol-6-yl]-methanesulfonamide | AA | 400.09 (M − H) |
| 206 | i-Pr | (2,3-dihydro-1H-indol-5-yl) | Me | N-(1-Isopropyl-2',3'-dihydro-1H,1'H-[3,5']biindolyl-6-yl)-methanesulfonylamide | S | 370.2 (M + H) |
| 207 | i-Pr | (3,5-difluoro-4-hydroxymethyl-phenyl) | Me | N-[3-(3,5-Difluoro-4-hydroxymethyl-phenyl)-1-isopropyl-1H-indol-6-yl]-methanesulfonamide | AA | 393.3 (M − H) |
| 208 | i-Pr | (1,2,3,4-tetrahydro-quinolin-6-yl) | Me | N-[1-Isopropyl-3-(1,2,3,4-tetrahydro-quinolin-6-yl)-1H-indol-6-yl]-methanesulfonamide | S | 384.0 (M + H), 382.3 (M − H) |
| 209 | i-Pr | (4-difluoromethyl-3,5-difluoro-phenyl) | Me | N-[3-(4-Difluoromethyl-3,5-difluoro-phenyl)-1-isopropyl-1H-indol-6-yl]-methanesulfonamide | Q | 413.1 (M − H) |
| 210 | i-Pr | (6-difluoromethyl-pyridin-3-yl) | Me | N-[3-(6-Difluoromethyl-pyridin-3-yl)-1-isopropyl-1H-indol-6-yl]-methanesulfonamide | Q | 380.3 (M + H) |
| 211 | i-Pr | (5-ethynyl-pyridin-2-yl) | Me | N-[3-(5-Ethynyl-pyridin-2-yl)-1-isopropyl-1H-indol-6-yl]-methanesulfonamide | *** | 354.3 (M + H) |

TABLE 4-continued

Compounds Prepared From Intermediate 4-A

| Ex. | R1 | R3 | R6 | Name | Prep. ‡ | Anal. † |
|---|---|---|---|---|---|---|
| 212 | i-Pr | 2-nitro-pyridin-5-yl (NO2 at 2-position) | Me | N-[1-Isopropyl-3-(6-nitro-pyridin-3-yl)-1H-indol-6-yl]-methanesulfonamide hydrochloride | C | 373.0 (M − H) |
| 223 | i-Pr | 5-chloro-thiophen-2-yl | Me | N-[3-(5-Chloro-thiophen-2-yl)-1-isopropyl-1H-indol-6-yl]-methanesulfonamide | J | 1H-NMR |
| 224 | i-Pr | 4-carbamoyl-2-fluoro-phenyl | Me | 2-Fluoro-4-(1-isopropyl-6-methanesulfonylamino-1H-indol-3-yl)-benzamide: | AA | 390.3 (M + H) |
| 138 | i-Pr | 5-trifluoromethyl-pyridin-3-yl | Me | N-[1-isopropyl-3-(5-trifluoromethyl-pyridin-3-yl)-1H-indol-6-yl]-methanesulfonamide hydrochloride | CC | 398.0 |
| 139 | i-Pr | 5-cyano-4-methyl-thiazol-2-yl | Me | N-[3-(5-cyano-4-methyl-thiazol-2-yl)-1-isopropyl-1H-indol-6-yl]-methanesulfonamide | CC | 375.0 (M + H) |
| 140 | i-Pr | 4-difluoromethoxy-phenyl | Me | N-[3-(4-difluoromethoxy-phenyl)-1-isopropyl-1H-indol-6-yl]-methanesulfonamide | CC | 395.0 (M + H) |
| 141 | i-Pr | 3-difluoromethyl-5-fluoro-4-methoxy-phenyl (F, CHF2, OMe) | Me | N-[3-(4-difluoromethyl-3-fluoro-5-methoxy-phenyl)-1-isopropyl-1H-indol-6-yl]-methanesulfonamide | CC | 425.3 (M − H) |
| 151 | i-Pr | 6-difluoromethyl-pyridin-3-yl | Me | N-[3-(6-difluoromethyl-pyridin-3-yl)-1-isopropyl-1H-indol-6-yl]-methanesulfonamide | CC * DF2 DF3 | 378.3 (M − H) |

TABLE 4-continued

Compounds Prepared From Intermediate 4-A

| Ex. | R1 | R3 | R6 | Name | Prep. ‡ | Anal. † |
|---|---|---|---|---|---|---|
| 152 | i-Pr | 5-CF₃-pyridin-2-yl | Me | N-[1-isopropyl-3-(5-trifluoromethyl-pyridin-2-yl)-1H-indol-6-yl]-methanesulfonamide | CC | 398.0 (M + H) |
| 153 | i-Pr | 5-CN-thiazol-2-yl | Me | N-[3-(5-cyano-thiazol-2-yl)-1-isopropyl-1H-indol-6-yl]-methanesulfonamide | CC | 361.0 (M + H) |
| 164 | i-Pr | 4-CN-2-OMe-phenyl | Me | N-[3-(4-Cyano-2-methoxy-phenyl)-1-isopropyl-1H-indol-6-yl]2-methanesulfonamide | Q | 384.3 (M + H) |
| 165 | i-Pr | 4-CN-2-Et-3-Me-phenyl | Me | N-[3-(4-Cyano-2-ethyl-phenyl)-1-isopropyl-1H-indol-6-yl]-methanesulfonamide | Q | 382.0 (M + H) |
| 166 | i-Pr | 4-CN-2-CHF₂-phenyl | Me | N-[3-(4-Cyano-2-difluoromethyl-phenyl)-1-isopropyl-1H-indol-6-yl]-methanesulfonamide | Q | 421.3 (M + NH4) |
| 177 | i-Pr | 4-CN-3-F-5-OMe-phenyl | Me | N-[3-(4-Cyano-3-fluoro-5-methoxy-phenyl)-1-isopropyl-1H-indol-6-yl]-methanesulfonamide | AA | 419.0 (M + NH4) |
| 178 | i-Pr | 6-CN-5-F-pyridin-3-yl | Me | N-[3-(6-Cyano-5-fluoro-pyridin-3-yl)-1-isopropyl-1H-indol-6-yl]-methanesulfonamide | X | 373.0 (M + H) |
| 70 | i-Pr | 5-(C(=S)NH₂)-thiophen-2-yl | Me | 5-(1-Isopropyl-6-methanesulfonylamino-1H-indol-3-yl)-thiophene-2-carbothioic acid amide | R | 394 (M + H) |

TABLE 4-continued

Compounds Prepared From Intermediate 4-A

| Ex. | R1 | R3 | R6 | Name | Prep. ‡ | Anal. † |
|---|---|---|---|---|---|---|
| 137 | i-Pr | 5-(6-amino-pyridin-3-yl) | Me | N-[3-(6-Amino-pyridin-3-yl)-1-isopropyl-1H-indol-6-yl]-methanesulfonamide | F | 343.3 (M − H) |

\* See DF1 and DF2 Methods above.
\*\* Method Q without use of the microwave.
† Unless noted to the contrary the analytical data refers to the mass spectral data.
‡ Prep. Method of preparation referring to Schemes 1-6 and the accompanying experimental descriptions.
\*\*\* See the Experimental below Compounds listed below in Table 5 can be prepared from compounds having the general structure of an indole core illustrated as Intermediate 100 according to the procedures listed above.

TABLE 5

Compounds Prepared From Intermediate 100

| Ex. | R1 | R3 | R6 | Name | Prep ‡ | Anal. † |
|---|---|---|---|---|---|---|
| 30 | Me | 4-nitrophenyl | Me | N-[1-Methyl-3-(4-nitro-phenyl)-1H-indol-6-yl]-methanesulfonamide | C | 346.0 (M + H) |
| 225 | Et | 4-cyano-3-fluorophenyl | Me | N-[3-(4-Cyano-3-fluoro-phenyl)-1-ethyl-1H-indol-6-yl]-methanesulfonamide | D | 356.2 (M − H) |
| 226 | i-Pr | 2-fluoro-pyridin-4-yl | Me | N-[3-(2-Fluoro-pyridin-4-yl)-1-isopropyl-1H-indol-6-yl]-methanesulfonamide | S | 348.0 (M + H) |
| 227 | i-Pr | 6-fluoro-pyridin-3-yl | Me | N-[3-(6-Fluoro-pyridin-3-yl)-1-isopropyl-1H-indol-6-yl]-methanesulfonamide | S | 348.0 (M + H) |

TABLE 5-continued

Compounds Prepared From Intermediate 100

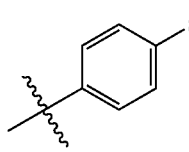

| Ex. | R1 | R3 | R6 | Name | Prep ‡ | Anal. † |
|---|---|---|---|---|---|---|
| 83 | i-Pr | 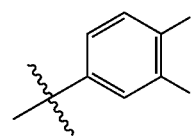 4-SCH₃-phenyl | Me | N-[1-Isopropyl-3-(4-methylsulfanyl-phenyl)-1H-indol-6-yl]-methanesulfonamide | C | 373.4 (M − H) |
| 84 | i-Pr | 3-F-4-CH₃-phenyl | Me | N-[3-(3-Fluoro-4-methyl-phenyl)-1-isopropyl-1H-indol-6-yl]-methanesulfonamide | C | 361.2 (M + H) |
| 85 | i-Pr | phenyl | Me | N-(1-Isopropyl-3-phenyl-1H-indol-6-yl)-methanesulfonamide | C | 327.2 (M − H) |
| 86 | i-Pr | 4-OMe-3-CH₃-phenyl | Me | N-[1-Isopropyl-3-(4-methoxy-3-methyl-phenyl)-1H-indol-6-yl]-methanesulfonamide | C | 371.2 (M − H) |
| 88 | i-Pr | 6-OMe-pyridin-3-yl | Me | N-[1-Isopropyl-3-(6-methoxy-pyridin-3-yl)-1H-indol-6-yl]-methanesulfonamide | C | 358.0 (M − H) |
| 228 | i-Pr | 2-Cl-pyridin-4-yl | Me | N-[3-(2-Chloro-pyridin-4-yl)-1-isopropyl-1H-indol-6-yl]-methanesulfonamide | C | 362.0 (M − H) |

† Unless noted to the contrary the analytical data refers to the mass spectral data.

‡ Prep. Method of preparation referring to Schemes 1-6 and the accompanying experimental descriptions.

Alternative synthetic schemes that be used to prepare indoles described in the present invention are illustrated below in Scheme 3, which can be accomplished using a compound having the indole core illustrated as intermediate 9, 9F, or 9C. Some of the methods listed in bold in the Scheme are described above; other methods are described below after the Scheme.

solution stir until the 3-bromo-6-nitro indole dissolves and then add benzenesulfonyl chloride (3.1 mL, 24 mmol, 1.2 eq). Let the solution stir overnight. Filter off the precipitate, which forms, wash the precipitate with $CH_2Cl_2$, and collect the filtrates to give 6.83 g of the title compound. Sequentially wash the combined filtrates with 1 M HCl, saturated sodium bicarbonate, and brine. Dry the organic layer over $Na_2SO_4$,

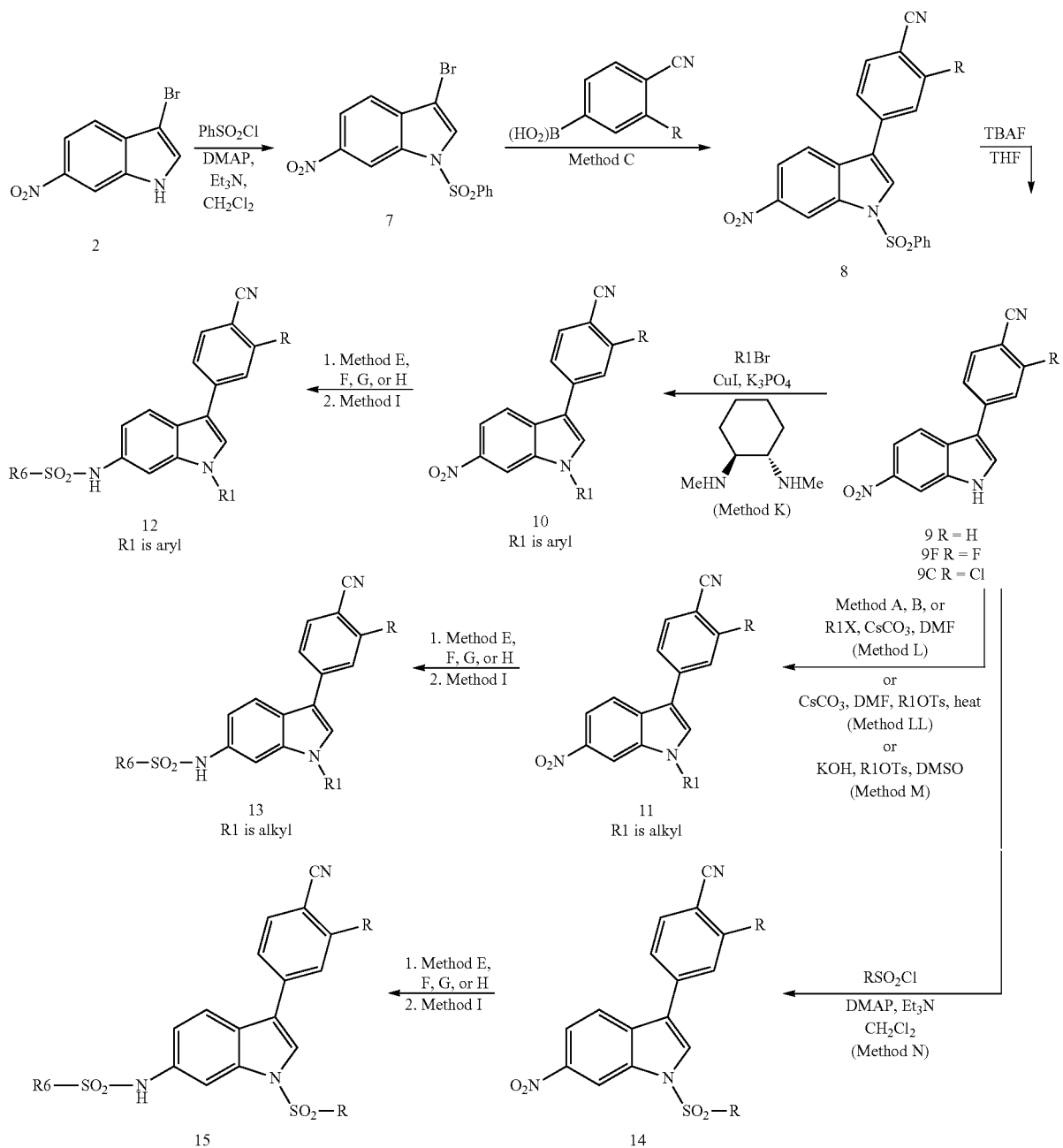

Scheme 3

1-benzenesulfonyl-3-bromo-6-nitro-1H-indole (7)

Add triethyl amine ($Et_3N$) (6.7 mL, 48 mmol, 4 eq) and DMAP (240 mg, 2.0 mmol, 0.1 eq) to a slurry of 3-bromo-6-nitro indole, 2 (4.82 g, 20 mmol) in 100 mL of $CH_2Cl_2$. Let the filter, and then concentrate the filtrate. Boil the resulting solid in ~30 mL of $CH_2Cl_2$ and a little MeOH, add 30 mL hexanes, let cool, and then filter off the precipitate to give another 1.3 g of the title compound. $^1$H NMR (DMSO-d6) δ 8.74 (d, 1H, J=2.2 Hz), 8.58 (s, 1H), 8.19 (dd, 1H, J=2.2, 8.8 Hz), 8.08-8.05 (m, 2H), 7.75-7.68 (m, 2H), 7.63-7.59 (m, 2H)—.

4-(1-benzenesulfonyl-6-nitro-1H-indol-3-yl)-benzonitrile (8)

Prepare this compound from 1-benzenesulfonyl-3-bromo-6-nitro-1H-indole, 7, and 4-cyanophenylboronic acid using Method C described above for 4-(1-isopropyl-6-nitro-1H-indol-3-yl)-benzonitrile 5. Purify by precipitation from EtOAc/hexanes. $^1$H NMR (DMSO-d6) δ 8.78 (d, 1H, J=1.8 Hz), 8.73 (s, 1H), 8.17 (dd, 1H, J=2.2, 8.8 Hz), 8.14-8.11 (m, 2H), 8.07 (d, 1H, J=8.8 Hz), 7.97-7.92 (m, 4H), 7.72 (tt, 1H, J=1.3, 7.5 Hz), 7.63-7.59 (m, 2H).

4-(6-nitro-1H-indol-3-yl)-benzonitrile (9)

Add 100 mL of 1 M TBAF in THF to a slurry of 4-(1-benzenesulfonyl-6-nitro-1H-indol-3-yl)-benzonitrile 8 (14.3 g, 35 mmol) in 50 mL of THF. Monitor the reaction by TLC. If starting material remains add more 1 M TBAF in THF until the reaction is complete. Pour reaction mixture into 200 mL of saturated aqueous sodium bicarbonate and then extract the resulting solution 3× with EtOAc. Combine the organic extracts and wash the extracts with saturated aqueous bicarbonate, water (2×), brine. Dry the resulting organic solution over $Na_2SO_4$, filter, and then remove the organic solvent to provide a solid. Redissolve the solid in ~400 mL of acetone with heating and then add ~100 mL hexanes until a precipitate forms. Let the solution cool and then collect the precipitate. Concentrate the filtrates and redissolve in ~300 mL of 50% acetone/hexanes with heating. Let the solution cool and then place in a freezer at −20° C. overnight. Collect the crystals that form. The combined yield of the title compound is 6.71 g, 25.5 mmol, 72%. LRMS (API ES−)=262.0 (M−1).

2-Fluoro-4-(6-nitro-1H-indol-3-yl)-benzonitrile (9F)

A. Dissolve 2-Fluoro-4-bromobenzonitrile (200 g, 990 mmol, 1.00 eq.) and triisopropyl borate (228 g, 1188 mmol, 1.2 eq.) in 700 mL of THF and 1400 mL of toluene. Cool the mixture with a dry ice/acetone bath to an internal temperature of −75° C. Slowly add n-BuLi (396 mL of a 2.5 M solution in hexanes) over a period of 2 hours. After addition is complete, a light-red, thin slurry occurs. Let the solution stir at −74° C. for 15 minutes, allow the solution to warm to −20° C. and then quench with 1500 mL of 2.5 M HCl. Let the solution warm to RT. Separate layers, extract the aqueous layer with EtOAc, dry the combined organic phases with $Na_2SO_4$, filter and concentrate in vacuo to yield a light-brown solid. Triturate the solid with hexane and transfer to a scintered glass funnel. Rinse with hexane one more time to obtain a pale-yellow filtrate. Stir the light-brown solid with cold $CH_2Cl_2$ and filter. Rinse with a small volume of $CH_2Cl_2$ to yield an off-white solid and a brown filtrate. Dry the solid in a vacuum oven at 40° C. and dried to yield 112 g (679 mmol, 69%) of 3-fluoro-4-cyanophenylboronic acid as an off-white solid.

B. 4-(1-Benzenesulfonyl-6-nitro-1H-indol-3-yl)-2-fluoro-benzonitrile from 1-benzenesulfonyl-3-bromo-6-nitro-1H-indole, 7, and 3-fluoro-4-cyanophenylboronic acid using Method AA: $Pd_2(dba)_3$, [(t-$Bu_3$)PH]$BF_4$, $K_2CO_3$, THF, $H_2O$. Purify by precipitation from EtOAc/hexanes. Remove the benzenesulfonyl protecting group using TBAF and THF as described for 4-(6-nitro-1H-indol-3-yl)-benzonitrile (9) above. LRMS (API ES−)=280.0 (M−1).

4-(6-Nitro-1-pyridin-3-yl-1H-indol-3-yl)-benzonitrile (10, R1=pyridine)

Method K Combine 4-(6-nitro-1H-indol-3-yl)-benzonitrile, 9 (265 mg, 1.0 mmol), potassium phosphate tribasic (513 mg, 2.4 mmol), copper (I) iodide (38 mg, 0.2 mmol), and 2 mL of DMF in a 4 mL vial. Add 3-bromopyridine (120 μL, 1.2 mmol) and rac-trans-N,N'-dimethylcyclohexane-1,2-diamine (127 μL, 0.8 mmol). Warm the solution to 110° C. Let the solution stir overnight. Let the solution cool to RT, isolate the yellow precipitate by filtration, and wash the precipitate sequentially with DMF, 1:1 DMF:$H_2O$, $H_2O$, DMF, EtOAc, and then hexanes. Dry the precipitate under vacuum to yield 301 mg, 0.88 mmol, 88% of the title compound. LRMS (API ES+)=341.0 (M+H).

4-[1-(3-Methyl-butyl)-6-nitro-1H-indol-3-yl]-benzonitrile (11, R1=i-Pr)

Method L Add $Cs_2CO_3$ (1.0 g, 1.88 mmol) to a solution of 4-(6-Nitro-1H-indol-3-yl)-benzonitrile, 9, (100 mg, 0.37 mmol) and isopentyl bromide (0.1 mL, 0.75 mmol) in DMF (10 mL). Stir overnight at ambient temperature. Remove the DMF solvent to provide a solid and partition the solid between EtOAc and $H_2O$, Sequentially wash the organic layer with $H_2O$ and brine then dry the organic layer over $MgSO_4$. Filter and remove the solvent leaving a solid. Purify by silica gel column chromatography (0-100% EtOAc/hexanes gradient) and concentrated to dryness to afford 180 mg (95%) of the title compound. LRMS (API ES+)=334.3 (M+H).

4-[1-(Cyano-methyl-methyl)-6-nitro-1H-indol-3-yl]-2-fluoro-benzonitrile

Method LL Add 2-Fluoro-4-(6-nitro-1H-indol-3-yl)-benzonitrile (1.24 mmoles; 350 mg), cesium carbonate (3.61 mmoles; 1.18 g) and dimethylformamide (10 mL) to a reaction vessel equipped with a stir bar. Stir this mixture for 10 minutes at room temperature then add toluene-4-sulfonic acid cyano-methyl-methyl ester (3.11 mmoles; 701 mg). Stir the resulting mixture for 5 hours at 55° C. Dilute this material with water (25 mL), brine (50 mL) and ethyl acetate (50 mL). Separate the organics and extract the resulting aqueous mixture with ethyl acetate (2×) and dichloromethane containing 10% methanol (2×). Combine the organics and concentrate in vacuo to about ½ volume. Wash the resulting mixture with water and evaporate the solvent in vacuo. Triturate the resulting yellow solids with hot dichloromethane. Collect the solids by vacuum filtration and rinse them with 50% dichloromethane/hexane to give the title compound (196 mg, 47%) yellow amorphous solid. MS (IS−) m/e 333.0 (M−1), 393.0 (M−1+OAc).

4-(1-cyclopentyl-6-nitro-1H-indol-3-yl)-benzonitrile (11, R1=cyclopentyl)

Method M Add KOH pellets (200 mg, 3.42 mmol) to a solution of 4-(6-nitro-1H-indol-3-yl)-benzonitrile, 9, (150 mg, 0.57 mmol) in DMSO (10 mL). After the KOH pellets dissolve, add cyclopenyl tosylate (210 mg, 0.85 mmol) in DMSO (3 mL). Allow the reaction mixture to stir overnight at ambient temperature. Add additional cyclopentyl tosylate (210 mg, 0.85) and allow the reaction mixture to stir for another 6 h. Add still more cyclopentyl tosylate (210 mg, 0.85 mmol) and allow the reaction mixture to stir overnight at ambient temperature. Quench the resulting reaction mixture with 5N HCl/ice. Extract the quenched reaction mixture with EtOAc. Wash the EtOAc extracts with brine. Dry the organic layer over $MgSO_4$, filter, and remove the solvent from the filtrate to provide a solid. Purify by silica gel column chromatography (0-100% EtOAc/hexanes gradient) and collect the fractions and remove the solvent to afford 110 mg (58%) of the title compound. LRMS (API ES+)=332.2 (M+H).

4-[6-Nitro-1-(pyridine-3-sulfonyl)-1H-indol-3-yl]-benzonitrile (14 R1=3-pyridinyl sulfonate)

Method N Combine 4-(6-nitro-1H-indol-3-yl)-benzonitrile, 9, (290 mg, 1.1 mmol), 4-dimethylaminopyridine (14 mg, 0.11 mmol), triethyl amine (740 μL, 5.3 mmol), methylene chloride (7.0 mL) and dimethylformamide (2.5 mL) in a 25 mL flask. Add 3-pyridine sulfonyl chloride hydrochloride (283 mg, 1.32 mmol). Let the solution stir overnight. Isolate the precipitate by filtration and wash the precipitate 3× with methylene chloride to yield 251 mg, 0.62 mmol, 56% of the title compound. LRMS (API ES+)=405.0 (M+H).

Once the desired functionalized intermediates 10, 11, and 14 are obtained using the general routes described above, the 6-nitro substituent can be reduced to the amine using the general procedures listed above for Scheme 1, i.e., Methods E-H, and then the amine can be converted to the alkyl sulfonamide using an appropriately selected alkyl sulfonyl chloride as described in Method I above to provide desired 6-alkyl sulfonamides 12, 13, and 15.

The compounds illustrated below in Table 6 can be prepared according to the above procedures starting from intermediates 9, 9F, or 9C in Scheme 2.

TABLE 6

Compound Prepared From Intermediates 9, 9C or 9F

| Ex. | R1 | R3 | R6 | Name | Prep ‡ | Anal. † |
|---|---|---|---|---|---|---|
| 26 | n-Pr | 4-cyanophenyl | Me | N-[3-(4-Cyano-phenyl)-1-propyl-1H-indol-6-yl]-methanesulfonamide | A, E, I | 371.0 (M + NH$_4$) |
| 27 | Et | 4-cyanophenyl | Me | N-[3-(4-Cyano-phenyl)-1-ethyl-1H-indol-6-yl]-methanesulfonamide | A, G, I | 357.2 (M + NH4) |
| 28 | i-Pr | 4-cyanophenyl | Me | N-[3-(4-Cyano-phenyl)-1-isopropyl-1H-indol-6-yl]-methanesulfonamide | A, E, I | 354.0 (M + H) |
| 46 | MeSO$_2$— | 4-cyanophenyl | Me | N-[3-(4-Cyano-phenyl)-1-methanesulfonyl-1H-6-yl]-methanesulfonamide | N, F, I | 388.0 (M − H) |
| 54 | isopropylsulfonyl | 4-cyanophenyl | Me | N-[3-(4-Cyano-phenyl)-1-isopropanesulfonyl-1H-indol-6-yl]-methanesulfonamide | N, F, I | 416.3 (M − 1) |
| 55 | pyridin-3-ylsulfonyl | 4-cyanophenyl | Me | N-[3-(4-Cyano-phenyl)-1-(pyridine-3-sulfonyl)-6-yl]-methanesulfonamide | N, F, I | 451.2 (M − 1) |

TABLE 6-continued

Compound Prepared From Intermediates 9, 9C or 9F

| Ex. | R1 | R3 | R6 | Name | Prep ‡ | Anal. † |
|---|---|---|---|---|---|---|
| 57 | 3-methyl-butyl | 4-cyanophenyl | Me | N-[3-(4-Cyano-phenyl)-1-(3-methyl-butyl)-1H-indol-6-yl]-methanesulfonamide | L, F, I | 382.3 (M − H) |
| 63 | cyclopentyl | 4-cyanophenyl | Me | N-[3-(4-Cyano-phenyl)-1-cyclopentyl-1H-indol-6-yl]-methanesulfonamide | M, F, I | 380.2 (M − H) |
| 64 | CH2C(O)OMe | 4-cyanophenyl | Me | [3-(4-Cyano-phenyl)-6-methanesulfonylamino-indol-1-yl]-acetic acid methyl ester | A, F, I | 382.0 (M − H) |
| 136 | (R)-tetrahydrofuran-3-yl | 4-cyano-3-fluorophenyl | Me | N-[(R)-3-(4-cyano-3-fluorophenyl)-1-tetrahydro-furan-3-yl-1H-indol-6-yl]-methanesulfonamide | LL, G, I | 417.0 (M + NH4) |
| 77 | cyclohexylmethyl | 4-cyanophenyl | Me | N-[3-(4-Cyano-phenyl)-1-cyclohexylmethyl-1H-indol-6-yl]-methanesulfonamide | L, F, I | 406.0 (M − H) |
| 229 | 2-methoxyethyl | 4-cyanophenyl | Me | 4-(1-(2-methoxyethyl)-6-methanesulfonylamino-1H-indol-3-yl)-benzonitrile | LL ‡, F, I | 368.3 (M − H) |
| 230 | 3-methoxypropan-2-yl | 4-cyanophenyl | Me | 4-(1-(3-methoxypropan-2-yl)-6-methanesulfonylamino-1H-indol-3-yl)-benzonitrile | LL, ‡ F, I | 384.1 (M + H) |
| 231 | (S)-3-methoxypropan-2-yl | 4-cyanophenyl | Me | 4-(1-(S-3-methoxypropan-2-yl)-6-methanesulfonylamino-1H-indol-3-yl)-benzonitrile | LL ‡, F, I * HPLC-A; 8.67 m | 406.1 (M + Na) |
| 232 | (R)-3-methoxypropan-2-yl | 4-cyanophenyl | Me | 4-(1-(R-3-methoxypropan-2-yl)-6-methanesulfonylamino-1H-indol-3-yl)-benzonitrile | LL ‡ F, I * HPLC-A; 9.63 m | 406.1 (M + Na) |

TABLE 6-continued

Compound Prepared From Intermediates 9, 9C or 9F

| Ex. | R1 | R3 | R6 | Name | Prep ‡ | Anal. † |
|---|---|---|---|---|---|---|
| 234 | (2-tetrahydrofuranylmethyl) | 4-CN-phenyl | Me | 4-(1-(2-tetrahydrofuranylmethyl)-6-methanesulfonylamino-1H-indol-3-yl)-benzonitrile | L, G, I * HPLC-B; Rt = 2.87 m | 368.3 (M − H) |
| 235 | (S)-2-methyl-3-methoxypropyl | 3-fluoro-4-CN-phenyl | Me | 2-fluoro-4-(1-(S-3-methoxypropan-2-yl)-6-methanesulfonylamino-1H-indol-3-yl)-benzonitrile | LL ‡, G, I | 400.0 (M − H) |
| 236 | (3-tetrahydrofuranylmethyl) | 4-CN-phenyl | Me | 4-(1-(3-tetrahydrofuranylmethyl)-6-methanesulfonylamino-1H-indol-3-yl)-benzonitrile | LL ‡, G, I, * HPLC-C; Rt = 10.68 m | 394.0 (M − H) |
| 239 | methylmercaptylmethyl | 3-fluoro-4-CN-phenyl | Me | 2-fluoro-4-(1-(methylmercaptylmethyl)-6-methanesulfonylamino-1H-indol-3-yl)-benzonitrile | L, G, I | 388.0 (M − H) |
| 240 | iPr | 3-fluoro-4-(N-methoxyimino)methyl-phenyl | Me | E-(1-(N-Methoxyimino))-2-fluoro-4-(1-isopropyl)-6-methanesulfonylamino-1H-indol-3-yl)-benzonitrile | Q, ** Z-1, Z-2 | 402.0 (M − H) |
| 241 | (S)-3-methylbutan-2-yl | 4-CN-phenyl | Me | 4-(1-(S-(3-methylbutan-2-yl)-6-methanesulfonylamino-1H-indol-3-yl)-benzonitrile | LL‡, G, I | 380.0 (M − H) |
| 242 | (R)-3-methylbutan-2-yl | 4-CN-phenyl | Me | 4-(1-(R-(3-methylbutan-2-yl)-6-methanesulfonylamino-1H-indol-3-yl)-benzonitrile | LL‡, G, I | 380.0 (M − H) |
| 244 | (R)-3-methylbutan-2-yl | 3-fluoro-4-CN-phenyl | Me | 3-Fluoro-4-(1-(R-3-methylbutan-2-yl)-6-methanesulfonylamino-1H-indol-3-yl)-benzonitrile | *** | 398.2 (M − H) |

TABLE 6-continued

Compound Prepared From Intermediates 9, 9C or 9F

| Ex. | R1 | R3 | R6 | Name | Prep ‡ | Anal. † |
|---|---|---|---|---|---|---|
| 245 | (R)-sec-butyl with isopropyl (3-methylbutan-2-yl) | 4-CN, 2-F phenyl | Me | 3-Fluoro-4-(1-(R-3-methylbutan-2-yl)-6-methanesulfonylamino-1H-indol-3-yl)-benzonitrile | LL‡, G, I HPLC-D Rt = 2.894 m | 398.2 (M − H) |
| 247 | 4-tetrahydropyranyl | 4-CN phenyl | Me | 4-(1-(4-tetrahydropyranyl)-6-methanesulfonylamino-1H-indol-3-yl)-benzonitrile | *** | 394.0 (M − H) |
| 68 | CH(Me)C(O)OMe | 4-CN phenyl | Me | 3-(4-Cyano-phenyl)-6-methanesulfonylamino-indole-1-carboxylic acid methyl ester | *** | 387.0 (M + NH4) |
| 29 | isobutyl | 4-CN phenyl | Me | N-[3-(4-Cyano-phenyl)-1-isobutyl-1H-indol-6-yl]-methanesulfonamide | A, E, I | 366.3 (M − H) |
| 248 | isopropylsulfonyl | 4-CN phenyl | Me | N-[3-(4-Cyano-phenyl)-1-(propane-2-sulfonyl)-1H-indol-6-yl]-methanesulfonamide | N, F, I | 416.3 (M − H) |
| 249 | 3-methoxyphenyl | 4-CN phenyl | Me | N-[3-(4-Cyano-phenyl)-1-(3-methoxy-phenyl)-1H-indol-6-yl]-methanesulfonamide | K, F, I | 435.0 M + NH4 |
| 72 | benzyl | 4-CN, 2-Cl phenyl | Me | N-[1-Benzyl-3-(4-cyano-phenyl)-1H-indol-6-yl]-methanesulfonamide | A, G, I | 419.0 (M + NH4) |
| 250 | pyridin-3-yl | 4-CN phenyl | Me | N-[3-(4-Cyano-phenyl)-1-pyridin-3-yl-1H-indol-6-yl]-methanesulfonamide | K, F, I | 389.0 (M + H) |
| 255 | 1-ethyl-propyl | 4-CN phenyl | Me | N-[3-(4-Cyano-phenyl)-1-(1-ethyl-propyl)-1H-indol-6-yl]-methanesulfonamide | L, F, I | 382.1 (M + H) |

TABLE 6-continued

Compound Prepared From Intermediates 9, 9C or 9F

| Ex. | R1 | R3 | R6 | Name | Prep ‡ | Anal. † |
|---|---|---|---|---|---|---|
| 256 | pyridin-3-ylmethyl | 4-cyanophenyl | Me | N-[3-(4-Cyano-phenyl)-1-pyridin-3-ylmethyl-1H-indol-6-yl]-methanesulfonamide | B, F, I | 403.0 (M + H) |
| 257 | cyclopropanesulfonyl | 4-cyanophenyl | Me | N-[3-(4-Cyano-phenyl)-1-cyclopropanesulfonyl-1H-indol-6-yl]-methanesulfonamide | N, F, I | 433.3 M + NH4 |
| 258 | 4-methoxybenzenesulfonyl | 4-cyanophenyl | Me | N-[3-(4-Cyano-phenyl)-1-(4-methoxy-benzenesulfonyl)-1H-indol-6-yl]-methanesulfonamide | N, F, I | 499.0 (M + NH4) |
| 259 | 3-methoxybenzenesulfonyl | 4-cyanophenyl | Me | N-[3-(4-Cyano-phenyl)-1-(3-methoxy-benzenesulfonyl)-1H-indol-6-yl]-methanesulfonamide | N, F, I | 499.0 (M + NH4) |
| 260 | (R)-1-pyridin-2-yl-ethyl | 4-cyano-3-fluorophenyl | Me | N-[3-(4-Cyano-3-fluoro-phenyl)-1-((R)-1-pyridin-2-yl-ethyl)-1H-indol-6-yl]-methanesulfonamide | BB, F, I | 435.0 (M + H) |
| 261 | cyano-methyl-methyl | 4-cyano-3-fluorophenyl | Me | N-[3-(4-Cyano-3-fluoro-phenyl)-1-(cyano-methyl-methyl)-1H-indol-6-yl]-methanesulfonamide | LL, F, I, | 381.2 (M − H) |
| 262 | 1-methyl-but-2-ynyl | 4-cyano-3-fluorophenyl | Me | N-[3-(4-Cyano-3-fluoro-phenyl)-1-(1-methyl-but-2-ynyl)-1H-indol-6-yl]-methanesulfonamide | BB, G, I | 394.2 (M − H) |
| 263 | 1-cyclopropyl-ethyl | 4-cyanophenyl | Me | N-[3-(4-Cyano-phenyl)-1-(1-cyclopropyl-ethyl)-1H-indol-6-yl]-methanesulfonamide | BB, F, I | 378.0 (M − H) |

TABLE 6-continued

Compound Prepared From Intermediates 9, 9C or 9F

| Ex. | R1 | R3 | R6 | Name | Prep ‡ | Anal. † |
|---|---|---|---|---|---|---|
| 264 | 1-cyclopropyl-ethyl | 4-cyanophenyl | Me | N-[3-(4-Cyano-phenyl)-1-(1-cyclopropyl-ethyl)-1H-indol-6-yl]-methanesulfonamide | BB, F, I | 378.0 (M − H) |
| 265 | dicyclopropylmethyl | 4-cyanophenyl | Me | N-[3-(4-Cyano-phenyl)-1-dicyclopropylmethyl-1H-indol-6-yl]-methanesulfonamide | BB, F, I | 404.0 (M − H) |
| 266 | tetrahydrofuran-3-yl | 4-cyanophenyl | Me | N-[(R)-3-(4-Cyano-phenyl)-1-tetrahydro-furan-3-yl-1H-indol-6-yl]-methanesulfonamide | LL, G, I | 380.11 (M − H) |
| 267 | 1-cyclopentyl-ethyl | 4-cyanophenyl | Me | N-[3-(4-Cyano-phenyl)-1-(1-cyclopentyl-ethyl)-1H-indol-6-yl]-methanesulfonamide | BB, F, I | 406.0 (M − H) |
| 98 | i-Pr | 4-cyanophenyl | CF$_3$ | N-[3-(4-Cyano-phenyl)-1-isopropyl-1H-indol-6-yl]-C,C,C-trifluoro-methanesulfonamide | (A, B or L) F, I | 406.2 (M − H) |
| 100 | i-Pr | 4-cyanophenyl | morpholin-4-yl | Morpholine-4-sulfonic acid [3-(4-cyano-phenyl)-1-isopropyl-1H-indol-6-yl]-amide | (A, B or L) F, I | 423.0 (M − H) |
| 301 | (S)-1-methyl-butyl | 4-cyanophenyl | Me | N-[3-(4-Cyano-3-fluoro-phenyl)-1-((S)-1-methyl-butyl)-1H-indol-6-yl]-methanesulfonamide | BB, F, I | 398.0 (M − 1) |

† Unless noted to the contrary the analytical data refers to the mass spectral data.
‡ Prep. Method of preparation referring to Shemes 1-6 and the accompanying experimental descriptions. Prepare the tosylate reagent according to the procedure for 3-Methyl-2-(4-methylphenylsulfonyloxy)butane below in Ex 224.
* HPLC-A: Chiralcel OJ-H; 30% IPA/CO2; 10 ml/m
HPLC-B: Chiralcel AD-H; 30% MeOH/CO2; 5 ml/m
HPLC-C: Chiralcel AD-H; 0.2% DMEA/3A EtOH; 0.6 ml/m
HPLC-D: Chiralcel AD-H; 0.2% DMEA/3A EtOH; 1 ml/m
** See Methods Z-1 and Z-2 below
*** See Experimental Description below.

In addition to the compounds prepared according the general procedures described above using the Methods and routes in Schemes 1-4, the following examples can be prepared by the procedures described herein.

Example 289

N-[3-(5-cyano-4-fluoro-thiophen-2-yl)-1-isopropyl-1H-indol-6-yl]-methanesulfonamide Heat a mixture of N-[3-(4-Chloro-5-cyano-thiophen-2-yl)-1-isopropyl-1H-indol-6-yl]-methanesulfonamide (Example 118) (0.15 g, 0.381 mmol) and CsF (0.324 g, 2.13 mmol) in DMSO (5 ml) at 150° C. for 6 hours under $N_2$. Cool the mixture to 21° C. and dilute with EtOAc. Wash the mixture with water, brine, and dried over $MgSO_4$. Filter the material and concentrate to dryness. Purify the crude product by reverse phase chromatography to yield 5 mg of the title compound. MS: 378.0 (MH+)

Example 290

2-Fluoro-4-(1-isopropyl-6-methanesulfonylamino-1H-indol-3-yl)-thiobenzamide

Add a drop of di-isopropylethylamine and a drop of water to N-[3-(4-Cyano-3-fluoro-phenyl)-1-isopropyl-1H-indol-6-yl]-methanesulfonamide (100 mg, 0.27 mmol) in 10 mL of dimethoxy ether. Heat to reflux, followed by addition of dithiophosphoric acid O,O'-diethyl ester (151 mg, 0.81 mmol), and reflux in a sealed tube overnight. Evaporate the solvent. Purification of the residue using silica gel chromatography eluted with EtOAc and hexane gradient to give 99 mg (91%) of the desired product.

Example 211

N-[1-isopropyl-3-(5-ethynyl-pyridin-2-yl)-1H-indol-6-yl]-methanesulfonamide

A. N-[1-isopropyl-3-(5-trimethylsilanylethynyl-pyridin-2-yl)-1H-indol-6-yl]-methanesulfonamide can be prepared using Method CC described above from 2-bromo-5-ethynyl trimethyl silane pyridine and N-[1-Isopropyl-3-(4,4,5,5-tetramethyl-[1,3,2]dioxaborolan-2-yl)-1H-indol-6-yl]-methanesulfonamide.

B. Add potassium carbonate (208 mg, 1.5 mmol) to N-[1-isopropyl-3-(5-trimethylsilanylethynyl-pyridin-2-yl)-1H-indol-6-yl]-methanesulfonamide (63 mg, 0.15 mmol) in MeOH (5 mL) and stir at room temperature for an hour. Evaporate the solvent. Purification of the crude residue using silica gel chromatography gave 14 mg (27% yield) of the desired product.

Example 194

N-[3-(4-Ethynyl-phenyl)-1-isopropyl-1H-indol-6-yl]-methanesulfonamide

Add N-[1-isopropyl-3-(4-trimethylsilanylethynyl-phenyl)-1H-indol-6-yl]-methanesulfonamide (0.223 mmoles; 95.0 mg, prepared similarly to N-[1-isopropyl-3-(5-trimethylsilanylethynyl-pyridin-2-yl)-1H-indol-6-yl]-methanesulfonamide), dichloromethane (4.0 mL), methanol (4.0 mL); followed by Potassium Carbonate (1.119 mmoles; 154.6 mg) to a round bottom flask equipped with a stir bar. Stir the resulting material for 2 hours at room temperature.

Dilute the reaction with water and acidify to pH of 6-7 with 1N HCl. Dilute the resulting aqueous mixture with brine and extract with dichloromethane. Concentrated the resulting mixture in vacuo and then purify the resulting material on a chromatotron (2MM silica gel plate; load $CH_2Cl_2$; run 30%-50% ethyl acetate gradient in hexanes) to obtain the desired product as a light-yellow crystalline solid, 50 mg (63%). MS (IS+) m/e 353.0 (M+1)

Example 243

N-[3-(4-Cyano-phenyl)-6-metanesulfonylamino-indol-1-yl]-N-methyl-acetamide

A. Add NaH (98 mg, 2.47 mmol) to 4-(6-nitro-1H-indol-3-yl)-benzonitrile (500 mg, 1.9 mmol) in DMF (10 mL) at 0° C. under $N_2$ and stir for additional 30 min at room temperature. Add excess $NH_2Cl$ ether solution prepared according to the procedure described in J. Org. Chem. 2004, 69 (4), 1369, and stir for an hour. Add 10% sodium bisulfite and extract with EtOAc. Wash the EtOAc extracts with 10% sodium bisulfite twice and dry over $MgSO_4$. Evaporate the solvent to give 4-(1-amino-6-nitro-1H-indol-3-yl)-benzonitrile.

B. Add acetic anhydride (214 mg, 2.1 mmol) to a mixture of 4-(1-Amino-6-nitro-1H-indol-3-yl)-benzonitrile (400 mg, 1.4 mmol) and di-isopropylethylamine (194 mg, 2.1 mmol) and N,N-dimethylaminopyridine (2 mg) in DMF (20 mL) and stir for 3 h. Add additional acetic anhydride (214 mg, 2.1 mmol) and di-isopropylethylamine (194 mg, 2.1 mmol) and stir overnight. Dilute the mixture with water and extract with EtOAc. Wash the combined extracts with water and brine, and dry over $MgSO_4$. Purify the crude residue using silica gel chromatography to give 170 mg (38% yield) of N-[3-(4-Cyano-phenyl)-6-nitro-indol-1-yl]-acetamide.

C. Add NaH (26 mg, 0.64 mmol) to a solution of N-[3-(4-Cyano-phenyl)-6-nitro-indol-1-yl]-acetamide (170 mg, 0.53 mmol) in DMF (30 mL) at 0° C. After stirring for 30 min, add MeI (170 mg, 0.64 mmol). Add additional NaH (26 mg, 0.64 mmol) stir for 30 min, then add MeI (170 mg, 0.64 mmol) and stir for 1 h. Add water and extract with EtOAc. Wash the extracts with water and brine, and dry over MgSO4. Purification of the crude residue using silica gel chromatography gave 108 mg (61% yield) of the desired product.

D. Use of the general procedure of catalytic reduction (Method F) and mesylation (Method I) described above provides N-[3-(4-cyano-phenyl)-6-methanesulfonylamino-indol-1-yl]-N-methyl-acetamide.

Example 68

3-(4-Cyano-phenyl)-6-methanesulfonylamino-indole-1-carboxylic acid methyl ester

Combine 4-(6-nitro-1H-indol-3-yl)-benzonitrile, 9,4-dimethylaminopyridine, triethyl amine, methylene chloride and dimethylformamide. Add methyl chloroformate. Let the solution stir until the starting material is consumed overnight. Isolate the precipitate by filtration and wash the precipitate with 10% DMF in methylene chloride and then methylene chloride to yield the title compound. Once the desired functionalized nitro intermediate is obtained Method F can be used to reduce to the amine and then the amine can be converted to the methyl sulfonamide using methyl sulfonyl chloride as described in Method I above to provide desired 6-methyl sulfonamides

Example 247

4-(1-(4-tetrahydropyranyl)-6-methanesulfonylamino-1H-indol-3-yl)-benzonitrile

A. 4-(4-methylphenylsulfonyloxy)tetrahydropyran: Add TsCl (22.33 g, 117.1 mmol) and DMAP (0.55 g, 4.5 mmol) to a mixture of 4-hydroxytetrahydropyran (9.2 g, 90.08 mmol), pyridine (10.93 ml, 135.12 mmol), and methylene chloride (180 ml). Stir the mixture for 7 days, then add hexanes (360 ml), and filter. Collect the filtrate and wash it sequentially with 5N HCl, and brine. Dry over $MgSO_4$, remove the solids by filtration and concentrate the filtrate Purify by silica gel chromatography (5-30% methylene chloride/hex) to give the product as an oil (20.75 90%). $^1$HNMR ($CDCl_3$): δ 1.70-1.91 (m, 4H), 2.47 (s, 3H), 3.48 (m, 2H), 3.86 (m, 2R), 4.65 (m, 1H), 7.35 (d, 2H, 8.8 Hz), 7.80 (d, 2H, 8.8 Hz).

B. 4-(1-(4-tetrahydropyranyl)-6-nitro-1H-indol-3-yl)-benzonitrile: Add $Cs_2CO_3$ (2.54 g, 7.8 mmol) to a mixture of 4-(6-nitro-1H-indol-3-yl)-benzonitrile (1.591 g, 6 mmol), 4-(4-methylphenylsulfonyloxy)tetrahydropyran (2 g, 7.8 mmol) in DMF (25 ml) and under $N_2$ atmosphere; heat the resulting mixture to 60° C. for 14 hours. After cooling, the reaction is poured into ice/water (200 ml) and 5N HCl (6 ml), sonicated, and filtered with $Et_2O$ wash to give 1:1 mixture of the title compound:starting material as a brownish red solid (1.202 g).

C. Using the general Methods G and I described above provides the title compound.

Example 244

3-Fluoro-4-(1-(R-3-methylbutan-2-yl)-6-methanesulfonylamino-1H-indol-3-yl)-benzonitrile and

Example 245

3-Fluoro-4-(1-(S-3-methylbutan-2-yl)-6-methanesulfonylamino-1H-indol-3-yl)-benzonitrile

A. 3-Methyl-2-(4-methylphenylsulfonyloxy)butane. Sequentially add TsCl (12.405 g, 65.07 mmol) and DMAP (0.305 g, 2.503 mmol) to a mixture of 3-methyl-2-butanol (4.412 g, 50 mmol), pyridine (8.1 ml, 100.19 mmol), and methylene chloride (40 ml). Stir the mixture for 20 h, add hex (40 ml), and filter with methylene chloride wash. Wash the combined filtrate with 5N HCl (15 ml) and brine; then dry over $MgSO_4$. Concentrate the filtrate and purify by chromatography (50-70% methylene chloride/hex) to give the title compound as an oil (9.15 g, 75%). LC: Rt=4.182 m (C18 capilliary, 80:20 MeOH/$H_2O$; 0.5 g/L $NH_4OAc$, 300 nm, 1 ml/m). $^1$HNMR (DMSO-d6): δ 0.75 (m, 61H), 1.10 (d, 3H, 7.8 Hz), 1.70 (m, 1H), 2.40 (s, 3H), 4.39 (m, 1H), 7.46 (d, 2H, 8.8 Hz), 7.77 (d, 2H, 8.8 Hz).

B. 4-(1-(3-methylbutan-2-yl)-6-nitro-1H-indol-3-yl)-benzonitrile: A mixture of 3-methyl-2-(4-methylphenylsulfonyloxy)butane (15.08 g, 62.226 mmol) and DMF (50 ml) is added via a syringe pump at 20 mL/h rate for a total of 2.5 h addition time to a 50° C. mixture of Intermediate 9,3-bromo-6-nitro-1H-indole, (10.00 g, 41.485 mmol), $Cs_2CO_3$ (27.04 g, 82.991 mmol, 2.0 eq), and DMF (100 ml), under $N_2$, The reaction is stirred for 24 hours at 50° C. After cooling, dilute the reaction with EtOAc and 1N HCl, then wash it with water (3×), brine, and then dry over $MgSO_4$. Remove the solids by filtration and concentrate the filtrate. Purify by chromatography to give the title compound as a yellow paste (9.83 g, 76%). LC-MS: 352.0 (M+M.)

C. Follow the general Methods G and I described above to provide the title compound. The isomers can be separated by chiral column: HPLC-D: Chiralcel AD-H, 0.2% DMEA/3A EtOH; 1 ml/m.

Example 121

[3-(5-Cyano-2-methyl-2H-pyrazol-3-yl)-1-isopropyl-1H-indol-6-yl]-methanesulfonamide

A. 5-(1-Isopropyl-6-nitro-1H-indol-3-yl)-2H-pyrazole-3-carboxylic acid ethyl ester: Sparge a stirring solution of 5-Tributylstannanyl-2H-pyrazole-3-carboxylic acid ethyl ester (47.7 g, 111 mmol), 3-Bromo-1-isopropyl-6-nitro-1H-indole (30.0 g, 106 mmol) and dichlorobis(triphenylphosphine) palladium(II) (3.72 g, 5.30 mmol) in DMF (400 mL) with argon for 20 minutes. After this time, stir the mixture at 150° C. for 1.25 h. Cool the resulting mixture to room temperature, dilute with ethyl acetate (2 L), filter through diatomaceous earth and wash the filter pad with ethyl acetate (1 L). Wash the filtrate with water (3×3 L) then brine (3 L); dry over sodium sulfate; filter and concentrate the filtrate under reduced pressure. Purify the residue obtained by column chromatography (silica, 9:11 ethyl acetate/heptane to 1:1 ethyl acetate/heptane) to afford 5-(1-Isopropyl-6-nitro-1H-indol-3-yl)-2H-pyrazole-3-carboxylic acid ethyl ester (17.4 g, 48%) as an orange solid: $^1$H NMR (300 MHz, $CDCl_3$) δ 11.25 (br s, 1H), 8.41 (m, 1H), 8.14 (d, J=9.0 Hz, 1H), 8.09 (dd, J=9.0, 1.8 Hz, 1), 7.91 (s, 1H), 7.12 (s, 1H), 4.82 (m, 1H), 4.44 (q, J=7.2 Hz, 2H), 1.63 (d, J=6.6 Hz, 6H), 1.44 (t, J=6.9 Hz, 3H).

B. 5-(1-Isopropyl-6-nitro-1H-indol-3-yl)-2H-pyrazole-3-carboxylic acid amide: Treat 5-(1-Isopropyl-6-nitro-1H-indol-3-yl)-2H-pyrazole-3-carboxylic acid ethyl ester (18.5 g, 54.0 mmol) with a 7 M solution of ammonia in methanol at 125° C. for 20 h (5 batches, 3.18 g-5.30 g, 200 mL of ammonia solution each). Combine all batches and concentrate under reduced pressure. Dissolve the residue obtained in boiling THF (700 mL), treat with 1,2-dichloroethane (300 mL) and concentrate under reduced pressure to afford 5-(1-Isopropyl-6-nitro-1H-indol-3-yl)-2H-pyrazole-3-carboxylic acid amide (18.0, >100%) as an orange solid: $^1$H NMR (500 MHz, DMSO-$d_6$, observed as a mixture of rotamers at ambient temperature) δ 13.46 (m, 1H), 8.65-8.60 (m, 1H), 8.40 (m, 0.5H, rotamer), 8.29 (s, 0.5H, rotamer), 8.25 (d, J=8.5 Hz, 0.5H, rotamer), 8.06-8.01 (m, 1.5H, rotamer), 7.92 (br s, 0.5H, rotamer), 7.56-7.53 (m, 1H), 7.22 (s, 1H), 7.03 (s, 0.5H, rotamer), 5.08 (m, 1H), 1.54 (d, J=6.5 Hz, 6H).

C. 5-(1-Isopropyl-6-nitro-1H-indol-3-yl)-2H-pyrazole-3-carbonitrile: React a mixture of 5-(1-Isopropyl-6-nitro-1H-indol-3-yl)-2H-pyrazole-3-carboxylic acid amide (18.0 g, 54.0 mmol) and phosphorous oxychloride (1 Kg) at 100° C. for 30 min. After this time, concentrate the reaction under reduced pressure, dilute with ethyl acetate (500 mL) and quench carefully with an aqueous saturated sodium bicarbonate solution (1.5 L). Pour the mixture over ethyl acetate (1 L), filter through diatomaceous earth and rinse the pad with ethyl acetate (500 mL). Dry the organic layer of the filtrate over sodium sulfate, filter and concentrate the filtrate under reduced pressure to afford 5-(1-Isopropyl-6-nitro-1H-indol-3-yl)-2H-pyrazole-3-carbonitrile (16.0 g, 100%) as a yellow solid: $^1$HNMR (300 MHz, DMSO-$d_6$) δ 14.19 (s, 1H), 8.67 (m, 1H), 8.46 (s, 1H), 8.09 (d, J=9.0 Hz, 1H), 8.02 (dd, J=9.0, 2.1 Hz, 1H), 7.42 (s, 1H), 5.11 (m, 1H), 1.54 (d, J=6.6 Hz, 6H).

D. 5-(1-Isopropyl-6-nitro-1H-indol-3-yl)-2H-pyrazole-3-carbonitrile and 5-(1-Isopropyl-6-nitro-1H-indol-3-yl)-1- methyl-1H-pyrazole-3-carbonitrile: Treat a stirring solution of 5-(1-isopropyl-6-nitro-1H-indol-3-yl)-2H-pyrazole-3-carbonitrile (16.0 g, 54.0 mmol) in THF (500 mL) at 0° C. with a 1 M solution of lithium bis(trimethylsilyl)amide in THF (81.0 mL, 81.0 mmol) and stir the resulting mixture at 0° C. for 10 min. After this time, treat the reaction with iodomethane (15.3 g, 108 mmol) and stir the resulting mixture at ambient temperature for 2 d. After this time, quench the reaction with water (100 mL), dilute with ethyl acetate (1.5 L) and wash with brine (1.5 L). Extract the aqueous layer with ethyl acetate (500 mL) and dry the combined organic layers over sodium sulfate, filter and concentrate the filtrate under reduced pressure. Purify by column chromatography (silica, 1:3 ethyl acetate/hexanes to 1:1 ethyl acetate/hexanes, then again, silica, 7:3, methylene chloride/hexane to methylene chloride) to afford 5-(1-Isopropyl-6-nitro-1H-indol-3-yl)-2H-pyrazole-3-carbonitrile (2.77 g, 17%) as an orange solid: mp 244-246° C.; $^1$HNMR (300 MHz, CDCl$_3$) δ 8.41 (d, J=1.8 Hz, 1H), 8.17 (d, J=9.0 Hz, 1H), 8.10 (dd, J=9.0, 2.1 Hz, 1H), 7.83 (s, 1H), 7.01 (s, 1H), 4.81 (m, 1H), 4.14 (s, 3H), 1.63 (d, J=6.6 Hz, 6H); m/z 310 [M+H]$^+$ and 5-(1-Isopropyl-6-nitro-1H-indol-3-yl)-1-methyl-1H-pyrazole-3-carbonitrile (9.92 g, 59%) as a yellow solid: $^1$HNMR (500 MHz, CDCl$_3$) δ 8.47 (d, J=2.0 Hz, 1H), 8.12 (dd, J=9.0, 2.0 Hz, 1H), 7.61 (s, 1H), 7.57 (d, J=8.5 Hz, 1H), 6.78 (s, 1H), 4.87 (m, 1H), 3.92 (s, 3H), 1.66 (d, J=7.0 Hz, 6H).

E. 5-(6-Amino-1-isopropyl-1H-indol-3-yl)-1-methyl-1H-pyrazole-3-carbonitrile: Prepare using Method G Purify by pouring the reaction carefully into a stirring solution of saturated aqueous sodium bicarbonate (1 L), diluted with ethyl acetate (1 L) and stir for 15 min. Filter the resulting mixture through diatomaceous earth. Separate the organic layer of the filtrate and wash with water (3×1 L) then brine (1 L). Dry the resulting solution over sodium sulfate, filter and concentrate the filtrate under reduced pressure to afford 5-(6-Amino-1-isopropyl-1H-indol-3-yl)-1-methyl-1H-pyrazole-3-carbonitrile (2.03 g, quant.) as a yellow foam: $^1$H NMR (300 MHz, CDCl$_3$) δ 7.30 (d, J=8.1 Hz, H), 7.12 (s, 1H), 6.72 (m, 2H), 6.66 (dd, J=8.4, 1.8 Hz, 1H), 4.58 (m, 1H), 3.93 (s, 3), 3.75 (br s, 2H), 1.55 (d, J=6.9 Hz, 6H).

D. [3-(5-Cyano-2-methyl-2H-pyrazol-3-yl)-1-isopropyl-1H-indol-6-yl]-methanesulfonamide Prepare using Method I Purify by chromatography (silica, 1:1 ethyl acetate/hexanes to ethyl acetate) then crystallize from methylene chloride/hexanes (×2) to afford N-[3-(5-cyano-2-methyl-2H-pyrazol-3-yl)-1-isopropyl-1H-indol-6-yl]-methanesulfonamide (1.96 g, 79%) as a white solid: mp 189-191° C.; $^1$H NMR (500 MHz, DMSO-d$_{0.6}$) δ 9.60 (s, 1H), 7.92 (s, 1H), 7.59 (d, J=8.5 Hz, 1H), 7.45 (d, J=1.5 Hz, 1H), 7.16 (s, 1H), 7.06 (dd, J=8.0, 1.5 Hz, 1H), 4.73 (m, 1H), 3.99 (s, 3H), 2.96 (s, 3H), 1.52 (d, J=7.0 Hz, 6H); m/z 358 [M+H]$^+$.

Example 124

N-[3-(5-Cyano-2-ethyl-2H-pyrazol-3-yl)-1-isopropyl-1H-indol-6-yl]-methanesulfonamide A. 2-Ethyl-5-(1-isopropyl-6-nitro-1H-indol-3-yl)-2H-pyrazole-3-carbonitrile 1-Ethyl-5-(1-isopropyl-6-nitro-1H-indol-3-yl)-1H-pyrazole-3-carbonitrile Treat a stirring solution of 5-(1-Isopropyl-6-nitro-1H-indol-3-yl)-2H-pyrazole-3-carbonitrile (0.400 g, 1.35 mmol) in DMF (10 mL) with a 60% dispersion of sodium hydride in mineral oil (0.065 g, 1.62 mmol) and stir the resulting mixture at ambient temperature for 5 min. After this time, treat the reaction with iodoethane (0.295 g, 1.89 mmol) and stir the resulting mixture at ambient temperature for 3 h. After this time, quench the reaction carefully with water (5 mL), dilute with ethyl acetate (100 mL) and wash with, water (3×100 mL) then brine (100 mL). Dry the combined organic layers over sodium sulfate and concentrate under reduced pressure. Purify the residue obtained by column chromatography (silica, 1:9 ethyl acetate/hexanes to 1:4 ethyl acetate/hexanes) to afford 2-Ethyl-5-(1-isopropyl-6-nitro-1H-indol-3-yl)-2H-pyrazole-3-carbonitrile (0.195 g, 45%) as an orange solid: $^1$H NMR (300 MHz, CDCl$_3$) δ 8.41 (d, J=2.1 Hz, 1H), 8.17 (d, J=8.7 Hz, 1H), 8.10 (dd, J=9.0, 2.1 Hz, 1H), 7.83 (s, 1H), 7.01 (s, 1H), 4.82 (m, 1H), 4.44 (q, J=7.2 Hz, 2H), 1.63 (m, 9H) and 1-Ethyl-5-(1-isopropyl-6-nitro-1H-indol-3-yl)-1H-pyrazole-3-carbonitrile (0.129 g, 30%) as a yellow solid: $^1$HNMR (300 MHz, CDCl$_3$) □ 8.47 (d, J=1.8 Hz, 1H), 8.11 (dd, J=9.0, 2.1 Hz, 1H), 7.58 (s, 1H), 7.53 (d, J=8.7 Hz, 1H), 6.74 (s, 1H), 4.86 (m, 1H), 4.18 (q, J=7.2 Hz, 2H), 1.66 (d, J=6.9 Hz, 6H), 1.44 (t, J=7.2 Hz, 3H).

B. 5-(6-Amino-1-isopropyl-1H-indol-3-yl)-1-ethyl-1H-pyrazole-3-carbonitrile

Stir a solution of 1-Ethyl-5-(1-isopropyl-6-nitro-1H-indol-3-yl)-1H-pyrazole-3-carbonitrile (0.127 g, 0.393 mmol) and tin(II) chloride dihydrate (0.887 g, 3.93 mmol) in DMF (2.5 mL) at 70° C. for 1 h. After this time, Pour the reaction carefully into a stirring solution of saturated aqueous sodium bicarbonate (50 mL), diluted with ethyl acetate (50 mL) and stir for 15 min. Filter the resulting mixture through diatomaceous earth. Separate the organic layer of the filtrate and wash with water (3×50 mL) then brine (50 mL). Dry the resulting solution over sodium sulfate, filtered and concentrate the filtrate under reduced pressure to afford 5-(6-Amino-1-isopropyl-1H-indol-3-yl)-1-ethyl-1H-pyrazole-3-carbonitrile (0.126 g, quant.) as a yellow foam. Use the foam without further purification.

C. N-[3-(5-Cyano-2-ethyl-2H-pyrazol-3-yl)-1-isopropyl-1H-indol-6-yl]-methanesulfonamide Stir a solution of 5-(6-Amino-1-isopropyl-1H-indol-3-yl)-1-ethyl-1H-pyrazole-3-carbonitrile (0.126 g, 0.393 mmol), pyridine (0.062 g, 0.786 mmol) and methanesulfonyl chloride (0.068 g, 0.590 mmol) in methylene chloride (3 mL) at room temperature for 2.5 h. After this time, Purify the reaction directly by chromatography (silica, methylene chloride to 1:9 ethyl acetate/methylene chloride) then freeze-dried from acetonitrile/water to afford N-[3-(5-Cyano-2-ethyl-2H-pyrazol-3-yl)-1-isopropyl-1H-indol-6-yl]-methanesulfonamide (0.132 g, 90%) as alight purple solid: mp 144-145° C.; $^1$H NMR (500 MHz, DMSO-d$_{0.6}$ δ0.60 (s, 1H), 7.84 (s, 1H), 7.50 (d, J=9.0 Hz, 1H), 7.45 (d, J=2.0 Hz, 1H), 7.11 (s, 1H), 7.04 (dd, J=8.5, 1.5 Hz, 1H), 4.73 (m, 1H), 4.27 (q, J=7.0 Hz, 21H), 2.96 (s, 3H), 1.52 (d, J=6.5 Hz, 6H), 1.35 (t, J=7.0 Hz, 3H) LCMS (Method 4)>99%, 6.96 min, m/z 372 [M+H]$^+$.

Example 270

N-[3-(4-Formyl-phenyl)-1-isopropyl-1H-indol-6-yl]-methanesulfonamide

Method Z-1 Place N-[3-(4-Cyano-phenyl)-1-isopropyl-1H-indol-6-yl]-methanesulfonamide (500 mg, 1.41 mmol), sodium hyposulfite hydrate (311 mg, 3.53 mmol) and Raney nickel (50% soln in water, 700 μL, 2.96 mmol) in a round bottom flask then add water (6 mL), glacial acetic acid (12 mL) and pyridine (12 mL). Warm to 50° C., and stir for 1.5 hours. Cool to ambient temperature; dilute with water (10 mL); and extract with ethyl acetate (10 mL×3). Combine organic layers, and wash with saturated sodium bicarbonate, water (×3) and brine. Dry over sodium sulfate, and concentrate in vacuo. Purify residue by flash chromatography on silica (2-50% ethyl acetate in hexanes) to give N-[3-(4-formyl-phenyl)-1-isopropyl-1H-indol-6-yl]-methanesulfonamide (413.1 mg, 82%). LRMS (API ES–)=355.0 (M–H).

Example 94

N-{3-[4-(Hydroxyimino-methyl)-phenyl]-1-isopropyl-1H-indol-6-yl}-methanesulfonamide Method Z-2 Place N-[3-(4-formyl-phenyl)-1-isopropyl-1H-indol-6-yl]-methanesulfonamide and hydroxylamine hydrochloride into a round bottom flask under nitrogen. Add ethanol (10 mL), tetrahydrofuran (10 mL) and pyridine. Warm to 60° C., and stir for 2 hours. Dilute with ethyl acetate (20 mL), and wash with 1N hydrochloric acid. Dry the organic layer over sodium sulfate, and concentrate in vacuo. Purify the residue by flash chromatography on silica (5-40% ethyl acetate in dichloromethane) to give N-{3-[4-(Hydroxy-imino-methyl)-phenyl]-1-isopropyl-1H-indol-6-yl}-methanesulfonamide (241.1 mg, 69%). LRMS (API ES+)=372.0 (M+H).

Example 271

N-[3-(3-Formyl-phenyl)-1-isopropyl-1H-indol-6-yl]-methanesulfonamide

Prepare according to Method Z-1 in substantially the same manner as N-[3-(4-formyl-phenyl)-1-isopropyl-1H-indol-6-yl]-methanesulfonamide. $^1$H NMR (DMSO-d6) δ 10.05 (s, 1H), 9.51 (s, 1H) 8.17 (s, 1H), 7.99 (d, 1H, 7.5 Hz), 7.95 (s, 1H), 7.84 (d, 1H, 8.4 Hz), 7.72 (d, 1H, 7.5 Hz), 7.59-7.63 (m, 1H), 7.38 (s, 1H), 7.03 (d, 1H, J=8.8 Hz), 4.62-4.69 (m, 1H), 3.27 (s, 3H), 2.92 (s, 3H), 1.48 (d, 6H, J=6.6 Hz).

Example 272

N-{3-[3-(Hydroxyimino-methyl)-phenyl]-1-isopropyl-1H-indol-6-yl}-methanesulfonamide Prepare according to method Z-2 in substantially the same manner as N-{3-[4-(hydroxyimino-methyl)-phenyl]-1-isopropyl-1H-indol-6-yl}-methanesulfonamide. LRMS (API ES+)=372.0 (M+H).

Example 300

1-N-hydroxyiminyl-2-fluoro-4-(1-(isopropyl)-6-methanesulfonylamino-1H-indol-3-yl)-benzene A. 1-formyl-2-fluoro-4-(1-(isopropyl)-6-metanesulfonylamino-1H-indol-3-yl)-benzene: Prepare according to Method Z-1 starting from 2-fluoro-4-(1 (isopropyl)-6-methanesulfonylamino-1H-indol-3-yl)-benzonitrile. Purify using chromatograph (methylene chloride to 5% EtOAc/methylene chloride) the residue to give the title compound as a yellow solid (156 mg, 78%). LC-MS: 375.1 (M+D).

B Prepare according the Method Z-2 starting from 1-formyl-2-fluoro-4-(1-(isopropyl)-6-methanesulfonylamino-1H-indol-3-yl)-benzene Purify by crystallized from hex/MeOH/methylene chloride to give the title compound as a light yellow solid (106 mg, 71%).

Example 52

(S)—N-[1-sec-Butyl-3-(5-formyl-thiophen-2-yl)-1H-indol-6-yl]-methanesulfonamide

Prepare according to the procedure for 1-N-hydroxyiminyl-2-fluoro-4-(1-(isopropyl)-6-methanesulfonylamino-1H-indol-3-yl)-benzene using the appropriate reagents to provide the title compound as a off-white solid (95%).

Example 275

Propane-2-sulfinic acid [3-(4-cyano-3-fluoro-phenyl)-1-isopropyl-1H-indole-6-y]-amide A Cool a mixture of isopropyl disulfide (3.77 g, 25.1 mmol) in acetic acid (2.90 mL) with brine/ice bath in a 50 mL round-bottom flask fitted with a 5 M sodium hydroxide trap, and add dropwise over a period of 30 min sulfuryl chloride (10.5 g, 77.8 mmol). Allow the resulting mixture to stir for 3 h. Remove the cooling bath and stir the reaction at ambient temperature for 2 hours then at 35° C. for an additional 1 hour. Purge the system with argon for 25 min and concentrate under reduced pressure at 45° C. to afford isopropyl sulfinyl chloride (6.37 g, 100%) as a yellow oil: $^1$H NMR (500 MHz, CDCl$_3$) δd 3.30 (m, 1H), 1.46 (d, J=7.0 Hz, 3), 1.44 (d, J=7.0 Hz, 3H).

B. Cool a mixture of 1-Isopropyl-3-(4-cyano-3-fluoro-phenyl)-1H-indol-6-ylamine (0.442 g, 1.51 mmol) and triethylamine (0.306 g, 3.02 mmol) in methylene chloride (10 mL) in a brine/ice bath under argon and treated with a solution of isopropyl sulfonyl chloride (0.210 g, 1.66 mmol) in methylene chloride and the resulting mixture was stirred in the cooling bath for 30 min. After this time dilute the reaction with methylene chloride (40 mL); wash with a saturated aqueous sodium bicarbonate solution (50 mL), then water (50 mL), then brine (50 mL); and dry over sodium sulfate. Remove the solids by filtration; concentrate the filtrate under reduced pressure. Triturate the residue with boiling methylene chloride (×3) then boiling acetonitrile to afford the title compound (0.212 g, 37%) as a white solid: mp 173-175° C. dec;

$^1$H NMR (500 MHz, DMSO-d6) δ 8.48 (s, 1H), 8.15 (s, 1H), 7.88 (m, 2H), 7.81 (d, J=12.0 Hz, 1H), 7.77 (d, J=8.0 Hz, 1H), 7.22 (d, J=1.5 Hz, 1H), 6.98 (dd, J=8.5, 1.5 Hz, 1H), 4.70 (m, 1H), 3.09 (m, 1H), 1.50 (d, J=6.5 Hz, 6H), 1.28 (d, J=7.0 Hz, 3H), 1.26 (d, J=7.0 Hz, 3); ESI MS m/z 382 [M+H]$^+$; m/z 294 [M+H—C$_3$H$_6$OS]+; HPLC (Method 2)>99% (AUC), tR=17.1 min.

Example 276

2-Fluoro-6-methyl-4-(1-(isopropyl)-6-methanesulfonylamino-1H-indol-3-yl)-benzonitrile A. 2-hydroxy-3-fluoro-5-bromobenzyl alcohol Add NaBH$_4$ (4.042 g, 106.84 mmol) over a 30 minutes to a mixture of 2-hydroxy-3-fluoro-5-bromobenzaldehyde (19.5 g, 89.037 mmol) and MeOH (445 ml) maintained at 0° C. Warm the reaction to RT, and stir for 14 h. Partially remove the solvent and dilute with EtOAc (500 ml). Acidify the resulting mixture with 1N HCl, and partition. Wash the organic layer with brine; dry over MgSO$_4$ remove the solids by filtration; and concentrate the filtrate to provide a white solid. Recrystallize the solid from Et₂O/methylene chloride/hexanes to give the title compound as a white solid (15.0 g, 76.2%). MS-ES: 218.9 (A+H), 220.9 (A+2+H).

B. 2-hydroxy-3-fluoro-5-bromotoluene. Add BF₃—OEt₂ (7.54 ml, 60 mmol) to a mixture of 2-hydroxy-3-fluoro-5-bromobenzyl alcohol (6.63 g, 30 mmol), Et₃SiH (23.96 ml, 150 mmol), and methylene chloride (120 ml) maintained at 0° C. Stir the reaction for 10 min, then warm to room temperature and stir for and additional 6 hours. Add Et₃SiH (11.98 ml, 75 mmol) and BF₃—OEt₂ (1.88 ml, 15 mmol) and stir for another 8 hours. Repeat if necessary. When the reaction is complete pour it into ice/water. Add a minimum of Et₂O to dissolve the solid and partition. Wash the organic layer with brine; dry over Na₂SO₄; remove the solids by filtration; and concentrate the filtrate. Crystallize from methylene chloride/hexanes at −20° C., then chromatograph (120 SiO₂, hexanes 30% methylene chloride/hex) to give the title compound as a white solid (3.71 g, 50.5%; Rf=0.2 [30%/hex]).

C. Treat 2-hydroxy-3-fluoro-5-bromotoluene using Method D above to give the title compound. Rf=0.43 (methylene chloride). MS-AP+: 328.1246 (M+H).

The following Scheme 4 illustrates a general synthetic route to provide desired functionalization at the indole C2 position. It will be understood that those skilled in the art can use alternative synthetic routes to provide the same or similar compounds.

rate the mixture with propyne gas, then add triethyl amine (3.6 mL, 25.90 mmol), seal the vessel, and stir at ambient temperature 14 hours. Concentrate the mixture in vacuo, suspend in 100 mL diethylether, add celite, and filter. Concentrate the filtrate in vacuo and chromatograph the residue over silica gel, eluting with hexanes/ethyl acetate (9:1 v/v) to afford the title compound, 1.75 g (76%). LRMS (API ES+)=177.0 (M+H).

2-Methyl-6-nitro-1H-indole (18, R2=CH₃)

Cool a mixture of sodium hydride (60% dispersion in oil, 0.33 g, 8.19 mmol) in anhydrous DMF to 0° C. under inert atmosphere. Add 5-nitro-2-prop-1-ynyl-phenylamine 17 (1.31 g, 7.44 mmol) in 10 mL DMF and stir 5 minutes. Add ethyl chloroformate (0.78 mL, 8.19 mmol), warm to ambient temperature, and stir 2 hours. Quench the reaction with saturated aqueous sodium bicarbonate, add ethyl acetate, and wash with saturated aqueous sodium bicarbonate followed by saturated aqueous brine. Dry the organic layer over sodium sulfate, filter, and concentrate in vacuo. Add to the residue a solution of sodium ethoxide in ethanol (0.6 M, 50 mL, 0.30 mmol) and reflux 14 hours. Cool to ambient temperature and concentrate in vacuo. Redissolve the residue in diethyl ether

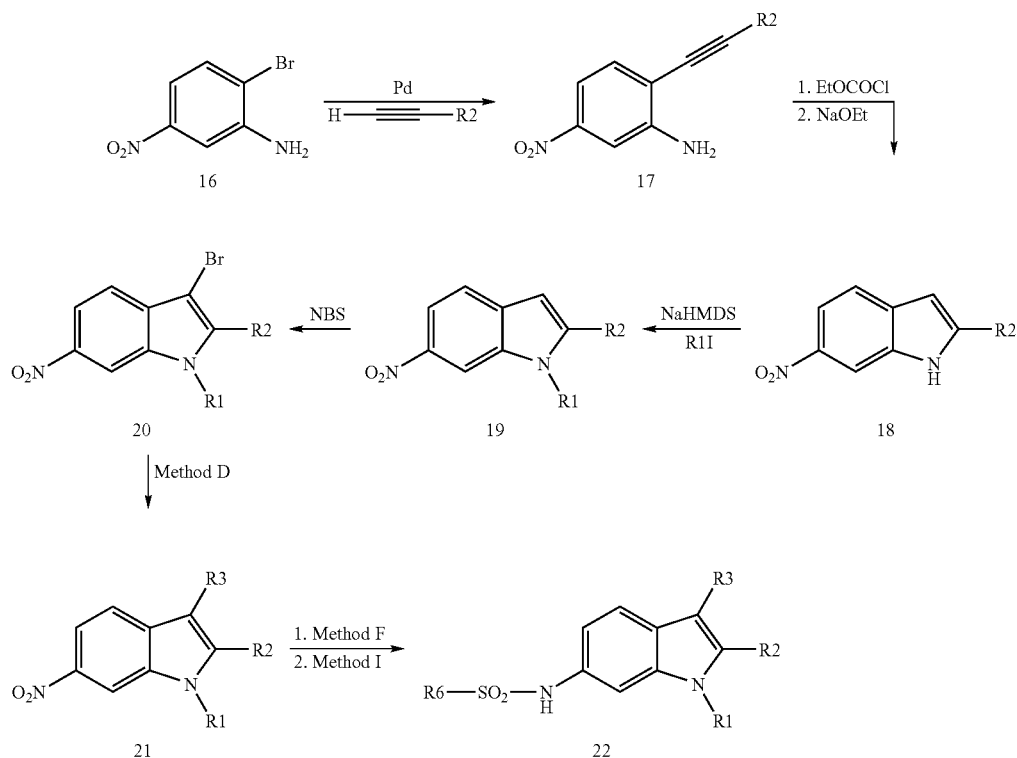

Scheme 4

5-nitro-2-prop-1-ynyl-phenylamine (17, R2=Me)

Stir a mixture of 2-bromo-5-nitroaniline 16 (2.81 g, 12.95 mmol), dichlorobis(triphenylphospine) palladium (II) (0.45 g, 0.65 mmol), and copper (I) iodide (0.12 g, 0.65 mmol) in anhydrous acetonitrile (10 mL) under inert atmosphere. Satuand wash with saturated aqueous sodium bicarbonate followed by saturated aqueous brine. Dry the organic layer over sodium sulfate, filter, concentrate in vacuo, and chromatograph the residue over silica gel, eluting with hexanes/ethyl acetate (9:1) to afford the title compound, 0.79 g (60%). LRMS (API ES−)=175.0 (M−H).

1-Ethyl-2-methyl-6-nitro-1H-indole (19, R1=CH$_2$CH$_3$, R2=CH$_3$)

Cool a solution of 2-methyl-6-nitro-1H-indole, 18 (0.31 g, 1.76 mmol) in anhydrous DMF (5 mL) under inert atmosphere at 0° C. Add sodium hexamethyldisilazide (1.0M in THF, 1.9 mL, 1.9 mmol) and stir 5 minutes. Add iodoethane (filtered through basic alumina) (0.43 mL, 5.28 mmol), warm to ambient temperature, and stir 2 hours. Quench the reaction with saturated aqueous sodium bicarbonate, add ethyl acetate, and wash with saturated aqueous sodium bicarbonate followed by saturated aqueous brine. Dry the organic layer over sodium sulfate, filter, and concentrate in vacuo. Chromatograph over silica gel using hexanes/ethyl acetate (9:1) to afford the title compound, (0.36 g, 100%). $^1$H NMR (CDCl$_3$, 300 MHz) δ 2.47 (s, 31), 4.18 (q, J=7.1 Hz, 2), 6.23 (s, 3H), 7.48 (d, J=8.8 Hz, 1H), 7.95 (dd, J=1.9, 8.6 Hz, 1H), 8.23 (d, J=1.9 Hz, 1H).

3-Bromo-1-ethyl-2-methyl-6-nitro-1H-indole (20, R1=CH$_2$CH$_3$, R2=CH$_3$)

Stir a solution of 1-ethyl-2-methyl-6-nitro-1H-indole, 19 (0.36 g, 1.76 mmol) and N-bromosuccinamide (0.31 g, 1.76 mmol) in anhydrous THF (10 mL) under inert atmosphere at ambient temperature for 14 hours. Quench the reaction with saturated aqueous sodium bicarbonate, add ethyl acetate, and wash with saturated aqueous sodium bicarbonate followed by saturated aqueous brine. Dry the organic layer over sodium sulfate, filter, and concentrate in vacuo. Chromatograph over silica gel using hexanes/ethyl acetate (9:1) to afford the title compound and unreacted 1-ethyl-2-methyl-6-nitro-1H-indole (0.37 g) in a 4:1 mixture which can be used in the subsequent step without further purification. LRMS (API ES+)=: 283, 285 (M, M+2M).

Alternatively desired indoles functionalized at the C2 position can be prepared according to the general procedures in the following Scheme 5 It will be understood that those skilled in the art can use alternative synthetic routes to provide the same or similar compounds.

Ethyl-3-iodo-6-nitro-1H-indole (R24)(R2=Et)

Add to a solution of 2-but-ynyl-5-nitro-phenylamine (2.98 g, 15.68 mmol) in anhydrous THF (100 mL) 2,6-di-t-butyl-4-methylpyridine followed by trifluoroacetic anhydride (2.7 mL, 19.61 mmol) and stir at room temperature for 18 hours. Quench the reaction with 1N HCl and add ethyl acetate. Extract the organic layer 2×1N HCl, 1× brine. Dry the organic layer over sodium sulfate, concentrate in vacuo, and redissolve in anhydrous acetonitrile (150 mL). Add to the solution potassium carbonate (6.49 g, 47.04 mmol) and cool to 0° C. Add iodine (11.94 g, 47.04 mmol) and stir at 0° C. for 30 min. Quench the reaction with 1M sodium thiosulfate (100 mL) and add water (250 mL). Stir the mixture 30 min., then filter and rinse with water to afford 3.94 g (80%) of the title compound.

1,2-Diethyl-3-iodo-6-nitro-1H-indole (25) (R1, R2=Et)

Add to a solution of 2-ethyl-3-iodo-6-nitro-1H-indole (0.30 g, 00.95 mmol) in anhydrous DMF (5 mL) sodium hexamethyldisilylamide (1.0M in THF, 1.0 mL, 1.00 mmol) dropwise followed by ethyl iodide (0.23 mL, 2.85 mmol) and stir 3 hours at ambient temperature. Quench the reaction with 1N HCl and add ethyl acetate. Wash the organic layer 2×1N HCl, 1× brine. Dry the organic layer over sodium sulfate, concentrate in vacuo, and flash chromatograph with 20% ethyl acetate hexane to afford 0.28 g (86%) of the title compound.

Compounds listed below in Table 7 can be prepared from compounds having the general structure of an indole core illustrated as Intermediate 17 according to the procedures listed above.

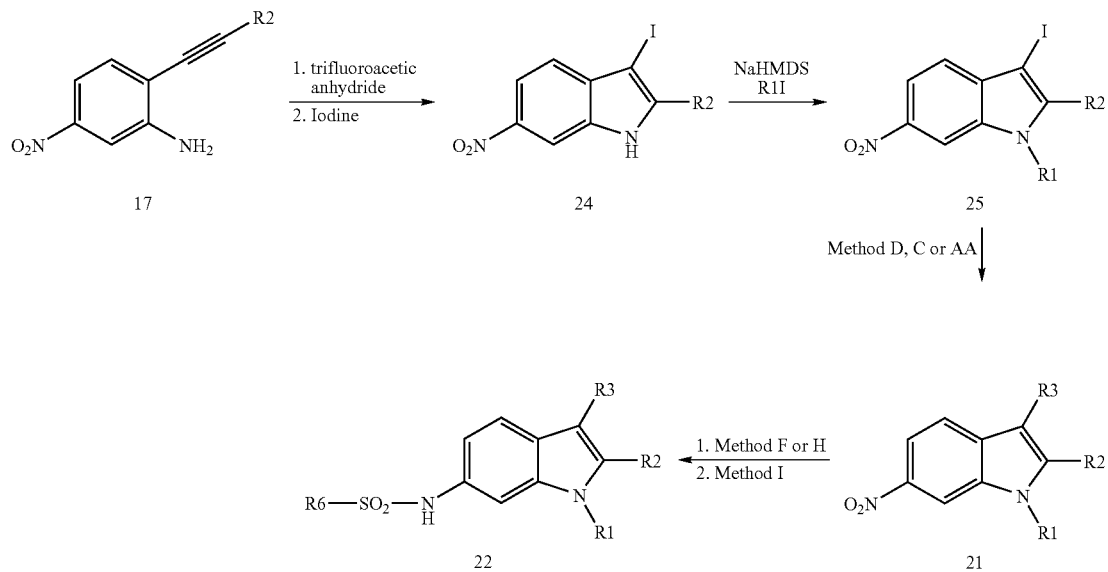

Scheme 5

TABLE 7

Compounds Prepared From Intermediate 17

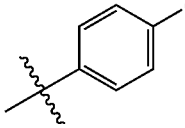

| Ex | R1 | R2 | R3 | Name | Prep ‡ | Anal. † |
|----|----|----|----|------|--------|---------|
| 280 | Et | Me | 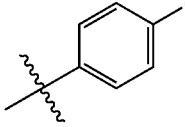 | N-[3-(4-Cyano-phenyl)-1-ethyl-2-methyl-1H-indol-6-yl]-methanesulfonamide | C, H, I | 354.0 |
| 281 | Et | i-Pr | 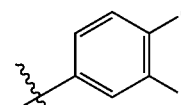 | N-[3-(4-Cyano-phenyl)-1-ethyl-2-isopropyl-1H-indol-6-yl]-methanesulfonamide | D, F, I | 382.0 (M + H) |
| 282 | Et | Me | 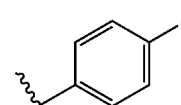 | N-[3-(4-Cyano-3-fluoro-phenyl)-1-ethyl-2-methyl-1H-indol-6-yl]-methanesulfonamide | D, F, I | 372.0 (M + H) |
| 283 | n-Pr | Me | 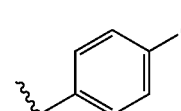 | N-[3-(4-Cyano-phenyl)-2-methyl-1-propyl-1H-indol-6-yl]-methanesulfonamide | C, F, I | 368.0 (M + H) |
| 284 | Me | Me | 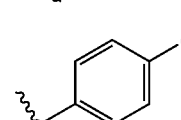 | N-[3-(4-Cyano-phenyl)-1,2-dimethyl-1H-indol-6-yl]-methanesulfonamide | C, F, I | 340.0 (M + H) |
| 285 | i-Bu | Me | 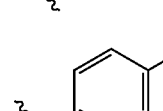 | N-[3-(4-Cyano-phenyl)-1-isobutyl-2-methyl-1H-indol-6-yl]-methanesulfonamide | AA, F, I | 382.0 (M + H) |
| 286 | i-Pr | Me |  | N-[3-(4-Cyano-phenyl)-1-isopropyl-2-methyl-1H-indol-6-yl]-methanesulfonamide | AA, F, I | 368.0 (M + H) |
| 287 | Et | n-Pr | 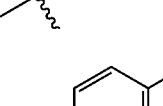 | N-[3-(4-Cyano-phenyl)-1-ethyl-2-propyl-1H-indol-6-yl]-methanesulfonamide | AA, F, I | 382.0 (M + H) |
| 288 | Et | Et | | N-[3-(4-Cyano-phenyl)-1,2-diethyl-1H-indol-6-yl]-methanesulfonamide | AA, F, I | 368.0 (M + H) |

† Unless noted to the contrary the analytical data refers to the mass spectral data.

Assays

The following assay protocol and result(s) thereof further demonstrating the utility and efficacy of the compounds and/or methods of the current invention are given for the purpose of illustration and are not meant to be limiting in any way. To demonstrate that compounds included within the present invention exhibit affinity for progesterone receptors binding assays are performed. Functional assays provide support that the compounds of the present invention exhibit the ability to modulate the progesterone receptor activity. All ligands, radiolabels, solvents, and reagents employed in the following assays are readily available from commercial sources, or can be readily synthesized by one skilled in the art.

Binding Assays

Cell lysates from HEK293 cells overexpressing human GR (glucocorticoid receptor), AR (androgen receptor), MR (mineralocorticoid receptor) or PR (progesterone receptor) are used for competition binding assays to determine $K_i$ values for compounds of interest. Briefly, competition binding assays are run in a buffer containing 20 mM HEPES, pH 7.6, 0.2 mM EDTA, 75 mM NaCl, 1.5 mM $MgCl_2$, 20% glycerol, 20 mM sodium molybdate, 0.2 mM DTT, 20 ug/ml aprotinin, and 20 ug/ml leupeptin, using either 0.3 nM $^3$H-dexamethasone for GR binding, 0.36 nM $^3$H-methyltrienolone for AR binding, 0.25 nM $^3$H-aldosterone for MR binding, or 0.29 nM $^3$H-methyltrienolone for PR binding, and either 20 ug 293-GR lysate, 22 ug 293-AR lysate, 20 ug 293-MR lysate or 40 ug 293-PR lysate per well. Competing compounds are added at various concentrations in half-log increments. Non-specific binding is determined in the presence of 500 nM dexamethasone for GR binding, 500 nM aldosterone for MR binding, or 500 nM methyltrienolone for AR and PR binding. The binding reaction (140 µl) is incubated overnight at 4° C., then 70 µl of cold charcoal-dextran buffer (containing per 50 ml of assay buffer, 0.75 g of charcoal and 0.25 g of dextran) is added to each reaction. Plates are mixed 8 minutes on an orbital shaker at 4° C. Plates are then centrifuged at 3,000 rpm at 4° C. for 10 minutes. An aliquot of 120 µl of the mixture is transferred to another 96-well plate and 175 µl of Wallac Optiphase "Hisafe 3" scintillation fluid is added to each well. Plates are sealed and shaken vigorously on an orbital shaker. After an incubation of 2 hrs, plates are read in a Wallac Microbeta counter. The data is used to calculate an $IC_{50}$ and % inhibition at 10 µM. The $K_d$ for $^3$H-dexamethasone for GR binding, $^3$H-methyltrienolone for AR binding, $^3$H-aldosterone for MR binding, or $^3$H-methyltrienolone for PR binding, is determined by saturation binding. The $IC_{50}$ values for compounds are converted to $K_i$ using Cheng-Prusoff equation and the $K_d$ determined by saturation binding assay.

Preferred compounds of the present invention have PR binding value $K_i$ of 100 nM. More preferably the compounds of the present invention have PR binding value $K_i$ of <10 nM. Particularly preferred compounds of the present invention exhibit a PR binding selectivity of greater than or equal to about 10 times that for each of MR, GR, and AR as determined by comparing the $IC_{50}$ values or the $K_i$ values for the respective receptors.

TABLE 8†

Receptor Binding Assay Results

| # | PR Ki | MR Ki | AR Ki | GR Ki |
|---|-------|-------|-------|-------|
| 25 | ++++ | 0 | 0 | 0 |
| 28 | ++++ | 0 | 0 | 0 |
| 29 | ++++ | + | ++ | ++ |
| 30 | ++++ | 0 | 0 | 0 |
| 32 | ++++ | 0 | 0 | 0 |
| 36 | ++++ | 0 | + | 0 |
| 38 | ++++ | + | + | 0 |
| 43 | ++++ | ++ | ++ | 0 |
| 59 | ++++ | 0 | + | 0 |
| 63 | ++++ | 0 | 0 | 0 |
| 72 | ++++ | ++++ | 0 | +++ |
| 74 | ++++ | ++ | 0 | 0 |
| 77 | ++++ | ++ | ++ | ++ |
| 78 | ++++ | ++ | +++ | ++ |
| 83 | ++++ | + | 0 | 0 |
| 84 | ++++ | + | + | 0 |
| 85 | ++++ | + | ++ | 0 |
| 86 | ++++ | 0 | 0 | 0 |
| 87 | ++++ | 0 | 0 | 0 |
| 88 | ++++ | 0 | 0 | 0 |
| 89 | +++ | 0 | 0 | 0 |
| 93 | ++++ | ++ | ++ | 0 |
| 94 | ++++ | + | ++ | 0 |
| 95 | ++++ | + | + | 0 |
| 96 | ++++ | 0 | 0 | 0 |
| 97 | ++++ | 0 | 0 | 0 |
| 98 | ++++ | 0 | 0 | 0 |
| 100 | +++ | 0 | 0 | 0 |
| 107 | +++ | 0 | 0 | 0 |

Example number;
†++++: Ki < 50 nM;
+++: 50 nM < Ki < 100 nM;
++: 100 nM < Ki < 500 nM
+: 500 nM < Ki < 1000 nM
0: >1000 nM Functional Assays PR CTF Assay:

Human embryonic kidney HEK293 cells are co-transfected using Fugene. Briefly, the reporter plasmid pGL3 containing two copies of GRE (glucocorticoid response element $^5$'TGTACAGGATGTTCT$^3$') and TK promoter upstream of the luciferase reporter cDNA is transfected with a plasmid constitutively expressing human progesterone receptor (PR), using viral CMV promoter. Cells are transfected in T225 $cm^2$ flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 h and then exposed to various concentrations of test compounds in 1:4 dilution increments. In the antagonist assays low concentrations of agonist (0.05-0.08 nM of R5020) is also added to the media. After 24 h of incubation with compounds, cells are lysed and luciferase activity is determined. Data is fit to a 4 parameter-fit logistics curve to determine EC50 and IC50 values. The % efficacy is determined versus maximum stimulation obtained with 30 nM R5020. In the antagonist mode the % inhibition is determined verses the effects of 30 nM R5020 alone. Selected compounds in the present application exhibit an $IC_{50}$ of less than 200 nM. Example 48 exhibits in $IC_{50}$ of about 11.7 nM.

C3 Rat Uterine Assay:

This assay measures the PR antagonist potential of compounds in rats by measuring an mRNA endpoint of estrogenic stimulation in the uterus (increased complement 3 or C3), which is effectively blocked by a PR agonist (R5020, 17 alpha, 21-dimethyl-19-nor-pregn-4,9-diene-3,20-dione). Addition of a potential PR antagonist can then neutralize the blocking effect of the PR agonist, resulting in a measurable increase in uterine C3 expression.

Immature Sprague Dawley female rats (21 days old, each approximately 50 g in weight) are first administered the R5020 progestin subcutaneously in sesame oil vehicle at 0.1 mg/kg. The rats are then treated with ethynyl estradiol at a dose of 50 ug/kg plus a compound of interest at doses ranging from 1-30 mg/kg made up in 20% β-hydroxycyclodextran in water for an oral gavage volume of 0.3 ml. This dosing is done 3 times at 24 hour intervals. The control groups include rats treated with one of the following (administered and dosed as described above): 1) estrogen (E2) vehicle+R5020 vehicle, 2) E2+R5020 vehicle, 3) E2+R5020, and 4) E2+R5020+asoprisnil (comparator compound, 5 mg/kg). The rats are sacrificed by decapitation 2 hours after the final dose (50 hours total dosing time). Uteri are removed and cleaned of adipose tissue, and ½ (1 uterine horn) is flash-frozen in liquid nitrogen. The tissue is homogenized in TRIzol reagent using lysing matrix beads.

The RNA is isolated by chloroform extraction of the homogenized tissue, followed by isopropanol precipitation of the aqueous layer. The RNA is further purified by binding to a silica-gel based membrane or magnetic bead with a nucleic acid binding surface, and then eluted off with water. The RNA is converted to single strand cDNA via reverse transcriptase. These cDNA templates are analyzed by quantitative real-time PCR which multiplexes the C3 primer/probe set to an endogenous control gene. The resulting C3 data is normalized to the internal control. (Adapted from Lundeen, S. G. et al. *J. Steroid Biochemistry and Molecular Biology,* 2001, 78, 137-143.) Table 9 below provides data for representative compounds prepared according to the present invention.

McPhail Assay:

The effects of progesterone receptor modulators on uterine endometrial transformation are evaluated in New Zealand White Rabbits (Harlan, 800-900 g) using the McPhail assay adapted from McPhail, MK. *J Physiol,* 1934:145-156. To evaluate antagonistic effects of compounds, the rabbits are treated sc with cyclodextrin-encapsulated 17-β-estradiol (Sigma, 10.52 ug/kg/day in 1 ml of saline) on days 1-6. The rabbits are then treated sc with progesterone (Sigma, 1.0 mg/kd/day in 1 ml of corn oil) in combination with compound of the present invention (in 15% Povidone K12, 10% Pluronic F68 (poloxamer 188) in deionized water (DIW): probe sonicated to mean<2 micron, 3 ml dose volume) on days 7-12. To evaluate agonist effects of compound, the rabbits are treated with either a compound of interest or progesterone alone on days 7-12. On day 13 the animals are sacrificed, uteri removed and fixed in zinc formalin (Richard-Allan Scientific). The fixed uteri are sectioned into 2-3 mm transverse slices and stained with haematoxylin and eosin. A total of six slices (a proximal, medial and distal section from each uterine horn) are evaluated histologically and the progestational effect is scored using the McPhail index. The McPhail test can be used to identify SPRMs. Table 9 below provides data for representative compounds prepared according the present invention.

TABLE 9

| Ex | C3 ED50* (mg/kg) | McPhail Index** @ 10 mpk (Antagonist Mode) | McPhail Index** @ 30 mpk (Agonist Mode) |
|---|---|---|---|
| 50 | +++ | + | + |
| 48 | +++ | + | + |
| 197 | +++ | ++ | + |
| 53 | + | +++ | ++ |
| 170 | +++ | +++ | +++ |
| 49 | +++ | +++ | +++ |

C3 Assay
+++ <5
++ 5-10
+ >10

McPhail Index
+++ ≧3
++ 2-3
+ <2

Method of Treatment

As used herein, the term "effective amount" means an amount of compound of the present invention, i.e., Formula I, which is capable of or effective for treating or alleviating the symptoms of the various pathological conditions herein described. A specific dose of a compound administered according to this invention will, of course, be determined by the particular circumstances surrounding the case including, for example, but not limited to: the compound administered, the route of administration, the state of being of the patient, and the pathological condition being treated. A typical daily dose will contain a nontoxic dosage level of from about 0.01 mg to about 1000 mg/day of a compound of the present invention. Preferred daily doses generally will be from about 1 mg to about 250 mg/day.

The compounds of this invention may be administered by a variety of routes including oral, rectal, intravaginal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, solvate, prodrug, enantiomer or prodrug thereof, and a pharmaceutically acceptable carrier, diluent, or excipient. The total active ingredients in such formulations comprises from 0.1% to 99.9% by weight of the formulation.

The term "pharmaceutically acceptable" as used herein means that the carrier, diluent, excipients and salt are compatible with the other ingredients of the formulation and not deleterious to the recipient thereof.

Pharmaceutical formulations of the present invention may be prepared by procedures known in the art using well-known and readily available ingredients. For example, the compounds of Formula I can be formulated with common excipients, diluents, or carriers, and formed into tablets, capsules, suspensions, powders, and the like. Non limiting examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium, and magnesium stearate, and solid polyethyl glycols.

The compounds also may be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes. Compounds of Formula I, generally, will be administered in a convenient formulation as determined by the attending physician.

Compounds of the present invention can be administered with another active agent such as one or more of: SERMs, estrogen, ER agonists, ER antagonists, SARMs, GnRH agonist or antgonist, $P_4$ (progestrone), progestins, and other PR agonists or modulators. When used in combination with another active agent, a compound of the present invention and the active agent can be administered concurrently or sequentially. For example, a compound of the present invention can be administered concurrently with a SERM or a progestin to control fertility. When administered concurrently, it is understood that the two or more active agents can be administered in a single formulation i.e., a single tablet, elixir, injection, or patch, or in separate formulations i.e., in separately prepared tablets, elixirs, patches, or injections.

Alternatively, a compound of the present invention and another active agent can be administered sequentially. For example, a compound of the present invention can be administered sequentially to treat one or more gynecological disorders. A compound of the present invention can be administered during a first dosing period. Thereafter, another active agent such as a $P_4$, a progestin, or other PR agonists can be administered in a second dosing period. A non-treatment period may or may not be instituted between the first and second dosing periods. It will be understood that order of administration can be reversed, i.e., a compound of the present invention can be administered during the second dosing period after the other active agent has been administered during the first dosing period.

In yet another alternative treatment regime, a compound of the present invention and another active agent can be administered intermittently. For example, a first agent, such as a compound of the present invention, can be administered for a dosing period, i.e., via a tablet, injection, elixir taken twice daily, daily, or weekly (or via a patch) while a second agent, such as one of the active agents listed above, is administered at one or more selected times or intervals during the dosing period. The times or intervals for administering the second agent can be selected by a physician and can be based upon menstrual cycle, related physical indications, hormonal levels, or disease state as deemed medically prudent or necessary. As noted above for the sequential administration regime, the administration of a compound of the present invention as the first agent and the other active agent as the second agent can be reversed.

As described herein the compounds of the present invention provide advantageous use to treat and or ameliorate one or more of the following: tumors; neoplasms; myomas; leiomyomas (uterine fibroids); endometriosis (adenomyosis); postoperative peritoneal adhesions; endometrial hyperplasia; polycystic ovary syndrome; carcinomas and adenocarcinomas of the uterus, ovary, breast, colon, and prostate; infertility; fertility control; female sexual dysfunction, and other gynecological or menstrual syndromes, such as, abnormal or dysfunctional bleeding, amenorrhea, menorrhagia, hypermenorrhoea, and dysmenorrheal; or pathological sequelae due to the above disorders/syndromes.

What is claimed is:

1. A compound which is 2-fluoro-4-(1-(S-3-methoxypropan-2-yl)-6-methanesulfonylamino-1H-indol-3-yl)-benzonitrile, or a pharmaceutically acceptable salt thereof.

2. A pharmaceutical composition comprising a compound according to claim 1, or a pharmaceutically acceptable salts thereof, and at least one of: a carrier, a diluent, and an excipient.

3. A method of treating leiomyomas comprising administering a therapeutically effective composition comprising a compound according to claim 1, or a pharmaceutically acceptable salt thereof, to a patient.

4. A method of treating endometriosis, comprising administering a therapeutically effective composition comprising a compound according to claim 1, or a pharmaceutically acceptable salt, thereof to a patient.

5. A method of treating gynecological or menstrual disorders in a mammal comprising administering a therapeutically effective dose of a compound according to claim 1, pharmaceutically acceptable salt, thereof to said mammal.

* * * * *